(12) United States Patent
Cropper et al.

(10) Patent No.: US 12,390,504 B2
(45) Date of Patent: Aug. 19, 2025

(54) POLYPHENOL BLEND OF CURCUMIN EXTRACT AND POMEGRANATE EXTRACT AND METHODS OF IMPROVING IMMUNE RESPONSE

(71) Applicant: Verdure Sciences, Inc., Noblesville, IN (US)

(72) Inventors: Sonya Cropper, Noblesville, IN (US); Nikeeta Kheradia, Noblesville, IN (US)

(73) Assignee: Verdure Sciences, Inc., Noblesville, IN (US)

( * ) Notice: Subject to any disclaimer, the term of this patent is extended or adjusted under 35 U.S.C. 154(b) by 0 days.

(21) Appl. No.: 17/214,339

(22) Filed: Mar. 26, 2021

(65) Prior Publication Data

US 2021/0299201 A1 Sep. 30, 2021

Related U.S. Application Data

(60) Provisional application No. 63/000,263, filed on Mar. 26, 2020.

(51) Int. Cl.
*A61K 36/185* (2006.01)
*A61K 9/107* (2006.01)
*A61K 31/12* (2006.01)
*A61P 37/06* (2006.01)

(52) U.S. Cl.
CPC .......... *A61K 36/185* (2013.01); *A61K 9/1075* (2013.01); *A61K 31/12* (2013.01); *A61P 37/06* (2018.01)

(58) Field of Classification Search
None
See application file for complete search history.

(56) References Cited

U.S. PATENT DOCUMENTS

| | | | |
|---|---|---|---|
| 7,638,640 B2 | 12/2009 | Seeram et al. | |
| 7,897,791 B2 | 3/2011 | Seeram et al. | |
| 7,919,636 B2 | 4/2011 | Seeram et al. | |
| 8,535,738 B2 * | 9/2013 | Collins | A61K 36/575 424/735 |
| 9,192,644 B2 | 11/2015 | Frautschy et al. | |
| 10,588,866 B2 | 3/2020 | Tingorani et al. | |
| 2004/0156920 A1 * | 8/2004 | Kane | A01N 63/10 424/754 |
| 2008/0268095 A1 * | 10/2008 | Herzog | A61P 3/02 426/2 |
| 2009/0110789 A1 * | 4/2009 | Mower | A23L 33/105 426/330.5 |

FOREIGN PATENT DOCUMENTS

| | | | |
|---|---|---|---|
| EP | 1993365 | * | 5/2013 |
| EP | 1993365 B1 | | 5/2013 |

OTHER PUBLICATIONS

ProHealth (https://www.amazon.com/ProHealth-Optimized-Curcumin-Longvida-Pomegranate/dp/B06XHSTRWP) (Year: 2017).*
Eidenberger, T. et al. "Investigation of the Lymphatic Transport of Solid-lipid Curcumin Particles (Longvida®) in Comparison to Curcumin Extract in Rats," in 252nd ACS National Meeting, Philadelphia, PA. 55: (2016) (4 pages).
Nahar et al., "Anti-Inflammatory Effects of Novel Standardized Solid Lipid Curcumin Formulations" J. Med. Food, 18(7): 786-792 (2015).
Pfohl et al., "Hepatoprotective and anti-inflammatory effects of a standardized pomegranate (punica granatum) fruit extract in high fat diet-induced obese C57BL/6 mice" Int. J. Food Sci. Nutr., 72(4): 499-510 (2021).
Machida et al., "Effects of solid, lipid curcumin particles on alcohol metabolism—an exploratory and a randomized, double-blind, placebo-controlled, parallel-group crossover study" Pharmacology and Treatment (JPT), 48(5): 867-73 (2020) [Abstract Only].
Eidenberger, "Investigation of the Lymphatic transport of solid-lipid curcumin particles (Longvida®) in comparison to curcumin extract in rats" in 252nd ACS National Meeting, Philadelphia, PA. 55: (2016) (2 pages).
McFarlin et al., "Reduced inflammatory and muscle damage biomarkers following oral supplementation with bioavailable curcumin" BBA Clin., 18(5):72-8 (2016).
Nicol et al., "Curcumin supplementation likely attenuates delayed onset muscle soreness (DOMS)" Eur J Appl Physiol., 115(8): 1769-77 (2015).
Gary et al,. "Combined bead-based multiplex detection of RNA and protein biomarkers: Implications for understanding the time course of skeletal muscle injury and repair" Methods, 158: 92-96 (2019).
Tanner et al., "Combining single molecule counting with bead-based multiplexing to quantify biological inflammation time course following skeletal muscle injury" Methods, 158: 77-80 (2019).
McFarlin et al., "Does acute improvement in muscle recovery with curcumin supplementation translate to Long-term Training?" Journal of Science in Sport and Exercise, 1:203-207 (2019), pp. 1-5.
Sciberras et al., "The effect of turmeric (Curcumin) supplementation on cytokine and inflammatory marker responses following 2 hours of endurance cycling" J. Int. Soc. Sports. Nutr., 12(1): 5 (2015) (10 pages).
Davis et al., "Curcumin effects on inflammation and performance recovery following eccentric exercise-induced muscle damage" Am. J. Physiol. Regul. Integr. Comp. Physiol., 292(6): R2168-73 (2007).

(Continued)

*Primary Examiner* — Terry A McKelvey
*Assistant Examiner* — Jacob A Boeckelman
(74) *Attorney, Agent, or Firm* — Amin Wasserman Gurnani LLP; Valerie Neymeyer-Tynkov; George M. Carrera, Jr.

(57) ABSTRACT

This invention is directed to compositions comprising curcumin extract and pomegranate extract, and methods of improving immune response with the compositions. The compositions may be administered as a prebiotic and/or a dietary supplement.

19 Claims, 11 Drawing Sheets

(56) References Cited

OTHER PUBLICATIONS

Drobnic et al., "Reduction of delayed onset muscle soreness by a novel curcumin delivery system (Meriva(R)): a randomized, placebo-controlled trial" J. Int. Soc. Sports. Nutr., 11:31 (2014) (10 pages).
Bernecker et al., "Evidence for an exercise induced increase of TNF-alpha and IL-6 in marathon runners" Scand J. Med. Sci. Sports, 23(2): 207-14 (2013).
Suzuki et al., "Changes in markers of muscle damage, inflammation and HSP70 after an Ironman Triathlon race" Eur. J. Appl. Physiol., 98(6): 525-34 (2006).
McFarlin et al., "Baker's yeast beta glucan supplementation increases salivary IgA and decreases cold/flu symptomatic days after intense exercise" J. Diet Suppl., 10(3):171-83 (2013).
Bergendiova et al., "Pleuran (beta-glucan from Pleurotus osreatus) supplementation, cellular immune response and respiratory tract infections in athletes" Eur. J. Appl. Physiol., 111(9): 2033-40 (2011).
Gleeson et al., "Respiratory infection risk in athletes: association with antigen-stimulated IL-10 production and salivary IgA secretion" Scand J. Med. Sci. Sports., 22(3):410-17 (2012).
Bell et al., "Recovery facilitation with Montmorency cherries following high-intensity, metabolically challenging exercise" Appl. Physiol. Nutr. Metab., 40(4): 414-23 (2015).
McLeay et al., "Effect of New Zealand blueberry consumption on recovery from eccentric exercise-induced muscle damage" J. Int. Soc. Sports Nutr., 9(1): 19 (2012) (12 pages).
Michailidis et al., "Thiol-based antioxidant supplementation alters human skeletal muscle signaling and attenuates its inflammatory response and recovery after intense eccentric exercise" Am. J. Clin. Nutr., 98(1): 233-45 (2013).
Liu et al., "Liquid chromatography coupled with time-of-flight tandem mass spectrometry for comprehensive phenolic characterization of pomegranate fruit and flower extracts used as ingredients in botanical dietary supplements" J. Sep. Sci., 41(15): 3022-33 (2018).
Gleeson et al., "Influence of training load on upper respiratory tract infection incidence and antigen-stimulated cytokine production" Scand. J. Med. Sci. Sports, 23(4):451-57 (2013).
Gleeson, "Immune function in sport and exercise" J. Appl. Physiol., 103: 693-99 (2007).
Walsh et al., "Position statement part one: Immune function and exercise" Exercise Immunology Review, 17: 6-63 (2011).
Walsh et al., "Position statement part two: Maintaining immune health" Exercise Immunology Review, 17: 64-103 (2011).
Gleeson et al., "Sex differences in immune variables and respiratory infection incidence in an athletic population" Exercise Immunology Review, 17: 122-135 (2011).
Ogawa et al., "Plasma adenosine triphosphate and heat shock protein 72 concentrations after aerobic and eccentric exercise" Exercise Immunology Review, 17: 136-149 (2011).
Maltseva et al., "Killer cell immunoglobulin-like receptors and exercise" Exercise Immunology Review, 17: 150-163 (2011).
Gillum et al., "A review of sex differences in immune function after aerobic exercise" Exercise Immunol. Rev. 17: 104-121 (2011).
Genetic Engineering & Biotechnology News, "Gut Microbiome—Pomegranate Partnership Reduces Colitis", https://www.genengnews.com/news/gut-microbiome-pomegranate-partnership-reduces-colitis-in-mice/ (Jan. 10, 2019) (5 pages) [Version available online as of Jun. 17, 2022].
Li et al., "Pomegranate ellagitannins stimulate growth of gut bacteria in vitro: Implications for prebiotic and metabolic effects", Anaerobe, Aug. 2015;34:164-168 [Abstract Only].
Paddock, "Gut bacteria unleash anti-aging power of pomegranates", Medical News Today https://www.medicalnewstoday.com/articles/311572# Urolithin-A-is-the-only-molecule-that-can-relaunch-mitophagy, (3 pages) [Version available online as of Jun. 17, 2022].

\* cited by examiner

POLYPHENOL BLEND OF CURCUMIN EXTRACT AND POMEGRANATE EXTRACT AND METHODS OF IMPROVING IMMUNE RESPONSE

CROSS-REFERENCE TO RELATED APPLICATIONS

This application claims priority from U.S. Provisional Application No. 63/000,263, filed Mar. 26, 2020, which is incorporated by reference herein in its entirety.

FIELD OF THE INVENTION

The present invention relates to compositions comprising curcumin and pomegranate extracts, and methods of improving immune response. The compositions may be administered as a prebiotic and/or a dietary supplement.

BACKGROUND

Maintaining a physically active lifestyle is important to overall health and wellness. Endurance running training can lead to the gradual accumulation of inflammation and soreness ultimately resulting in overuse injuries. Management of soreness and inflammation with pharmaceuticals (e.g. NSAIDs) during a long-term training regime is not a suitable solution due to known side effects (e.g. liver damage).

Curcumin (diferuloylmethane), extracted from ground rhizomes of the turmeric plant (*Curcuma longa* L. plant), is a yellow-colored, lipophilic, water-insoluble, low molecular weight polyphenol. Curcumin acts as an antioxidant and anti-inflammatory agent by enhancing activities of endogenous antioxidants (i.e. superoxide dismutase, catalase, glutathione peroxidase), blunting the action of cyclooxygenase-2 (COX-2), and blocking the activation of nuclear factor kappa beta (NF-κb). The delivery system Longvida®, formulating curcumin with SLCP (Solid Lipid Curcumin Particle) technology, improves the bioavailability of curcumin, delivering curcumin to blood and tissues and even allowing curcumin to cross the blood-brain-barrier. U.S. Pat. No. 9,192,644 and European Patent No. 1993 365 further describe Longvida®. The improved effects are thought to be due, at least in part, to an exponential increase in bioavailability and water solubility of curcumin formulated with the SLCP technology as opposed to regular unformulated curcumin. See Nahar et al., "*Anti-Inflammatory Effects of Novel Standardized Solid Lipid Curcumin Formulations*" *J. Med. Food* 18(7):786-792 (2015), showing up to a 760,000-fold increase in water solubility of curcumin when formulated with SLCP technology (Nahar Table 1).

Pomegranates (*Punica granatum*) are rich in polyphenolic compounds such as ellagitannins, including characteristic punicalagins and punicalins. Ellagitannins are hydrolysable tannins having antioxidant activity. [Liu et al., "*Liquid Chromatography Coupled with Time-of-flight Tandem Mass Spectrometry for Comprehensive Phenolic Characterization of Pomegranate Fruit and Flower Extracts Used as Ingredients in Botanical Dietary Supplements*" *J. Sep. Sci.* 41(15): 3022-33 (2018)]. U.S. Pat. Nos. 7,638,640; 7,897,791; and 7,919,636 describe some pomegranate extracts. Punicalagins and other components of pomegranate extracts may be metabolized in the gut to urolithins. Pomegranate and methylsulfonylmethane (MSM) have been shown to reduce oxidative stress and improve markers of systemic inflammation through downregulation of COX-2, NF-κb, and tumor necrosis factor alpha (TNFα). Pomegranate fruit extract has been shown to suppress high-fat diet-induced hepatic and neurological disease. [Pfohl et al. "*Hepatoprotective and Anti-Inflammatory Effects of a Standardized Pomegranate (Punica granatum) Fruit Extract in High Fat Diet-Induced Obese C57BL/6 Mice*" *Int. J. Food Sci. Nutr.* 1-12 (2020)].

A composition that supports or improves the immune system, under everyday circumstances or for instance after strenuous exercise, would be beneficial.

SUMMARY OF THE INVENTION

The present invention is directed to compositions comprising a combination of a curcumin extract and a pomegranate extract, and their use in methods for supporting and/or improving immune health, supporting and/or improving gut health, reducing feelings of stress and/or effects of stress, reducing risk of infection, and/or treating and/or preventing diseases and/or disorders of the immune system. The present invention is directed to a composition comprising a combination of a curcumin extract and a pomegranate extract; in an embodiment, a synergistic composition and/or combination providing a synergistic effect. In an embodiment, the composition and/or combination comprises 5-30% by weight curcuminoids and 3-50% by weight punicalagins; in an embodiment, said composition and/or combination comprises not less than 10% w/w total curcuminoids, not less than 5% w/w punicalagins, and 20-30% w/w total pomegranate polyphenols. In an embodiment, the combination is a ratio of curcumin extract:pomegranate extract in the range of about 5:1 to about 1:5 (w/w). In an embodiment, the above embodiments or other specific compositions of this invention are synergistic. In an embodiment, the curcumin extract is an optimized curcumin extract, in an embodiment Longvida®. In an embodiment, the pomegranate extract is the proprietary pomegranate extract, Pomella®.

The present invention is also directed to a method of supporting and/or improving immune health in a subject, including a healthy subject or a subject having an infection, comprising the steps of providing a composition comprising an effective amount of a combination of a curcumin extract, such as an optimized curcumin extract, and a pomegranate extract, and administering the composition to a subject in need thereof to support the immune system of the subject, such as the innate immune system and/or the adaptive immune system. In an embodiment, the method and combination of extracts of this invention are synergistic and/or provide significant results.

The present invention is also directed to a method of treating and/or preventing an immune-related disease or disorder in a subject, and/or treating or preventing a symptom thereof, comprising the steps of providing a composition comprising an effective amount of a combination of a curcumin extract and a pomegranate extract, in an embodiment in the range of about 5:1 to about 1:5 (w/w), in an embodiment where the curcumin extract is an optimized curcumin extract, in an embodiment Longvida®, and said pomegranate extract is Pomella®; and then administering the composition to the subject. In an embodiment, the method and combination of extracts are synergistic and/or provide significant results. In an embodiment, the disease treated is a viral or bacterial or other infection, such as COVID 19, a viral infection, or such as bronchitis, a bacterial or viral infection.

The present invention is also directed to a method of supporting and/or improving gut health in a subject, comprising the steps of providing a composition comprising an effective amount of a combination of a curcumin extract and a pomegranate extract, and then orally administering the composition to a subject in need thereof. In an embodiment, the method and combination of extracts are synergistic and/or provide significant results.

The present invention is also directed to a method of reducing feelings of stress or effects of stress in a subject, comprising the steps of providing a composition comprising an effective amount of a combination of a curcumin extract and a pomegranate extract, and administering the composition to a subject in need thereof. In an embodiment, the method and combination of extracts are synergistic and/or provide significant results.

The present invention is also directed to a method of reducing infection risk in a subject, comprising the steps of providing a composition comprising an effective amount of a combination of a curcumin extract and a pomegranate extract, and then administering the composition to a subject in need thereof. In an embodiment, the method and combination of extracts are synergistic and/or provide significant results.

DETAILED DESCRIPTION

Figure 1:
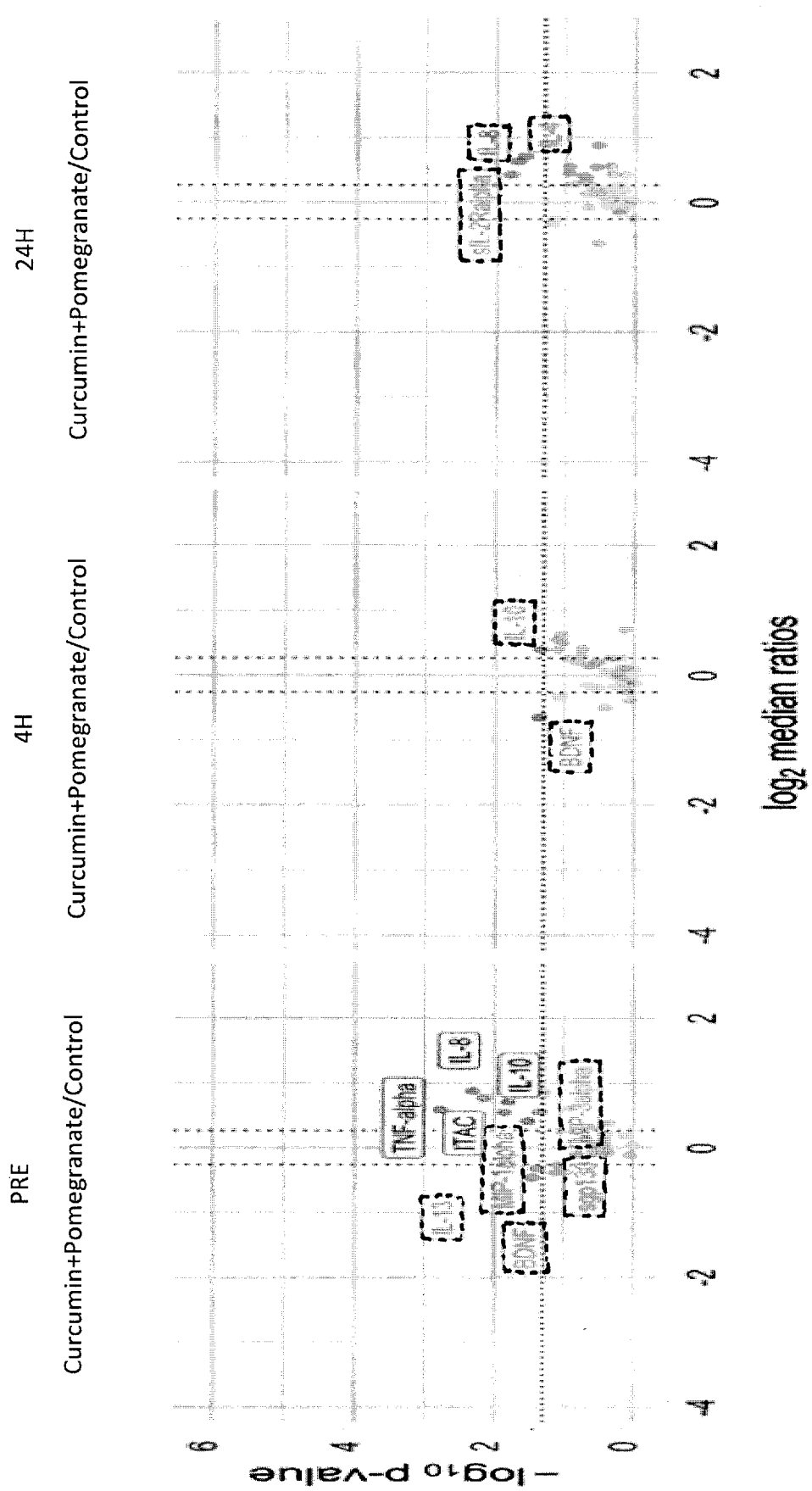
FIG. 1 shows a volcano plot showing protein biomarkers for inflammation that significantly increased or decreased in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

The present invention is directed to a composition comprising a curcumin extract and a pomegranate extract. The extracts, taken together, synergistically support and/or improve immune health, support and/or improve gut health, reduce feelings of stress and/or effects of stress, reduce risk of infection, and/or treat and/or prevent diseases and/or disorders of the immune system. Methods of using a combination of a curcumin extract and a pomegranate extract of the present invention also improve immune health, support and/or improve gut health, reduce feelings of stress and/or effects of stress, reduce risk of infection, and/or treat and/or prevent diseases and/or disorders of the immune system. A composition of the present invention may also include components and/or metabolites of curcumin extract and pomegranate extract. Isolated, purified, and/or synthetic curcuminoids, punicalagins, punicalins, urolithins, and other components of their metabolic pathway as available may be added to a composition of the present invention, or added in place of another component. Methylsulfonylmethane may be included in a composition of the present invention, or may be omitted.

In an embodiment, a composition of the present invention reduces the risk of infection and/or injury and promotes recovery from exercise-induced infection or injury, such as from strenuous exercise such as a half-marathon or training for a half-marathon, by increasing, modulating, and/or strengthening a subject's immune response, for instance in response to a cytokine storm. Over time, repeated exercise and physical training can increase the time needed for bodily tissues to recover. When that time is not taken, minor injuries can lead to major injuries, particularly during an exercise event. Administration of a composition of the present invention stimulates the immune response to reduce infection risk during times of stress and minor injury in the body, reducing the risk for further infection or injury, and reducing the risk for major infection or injury. Common ailments associated with endurance athletes in heavy training is their susceptibility to virus and bacterial infections such as bronchitis and flu (lung inflammation). Administration of compositions of the present invention afforded 15% more training sessions, 10% greater training volume, 6% improvement in Post-Half Marathon 10 k time trials. In an embodiment, infection and injury risk is reduced and recovery is promoted by the administration of the present compositions, without strenuous exercise, via the administration of a composition of this invention.

The present invention is also directed to a method of immunomodulating the immune system such as its pathways in a subject, comprising the steps of providing a composition of this invention and administering an effective among to a subject to reach the blood stream and bodily tissues and cells of the subject, and up regulate or down regulate mRNA expression related to immune pathways including Th17 Differentiation pathway, Toll-like receptor signaling pathway, Cytokine Signaling pathway, NF-κB Signaling pathway, NLR Signaling pathway, T cell receptor signaling pathway/Lymphocyte Activation pathway, TNF Family Signaling, in the subject. In an embodiment, administration according to this method is oral. The present invention is also directed to a method of immunomodulating immune system pathways in a subject via up regulation or down regulation of protein expression related to immune response, in a subject, comprising the steps of providing a composition comprising an effective amount of a combination of a curcumin extract and a pomegranate extract, and then orally administering the composition to a subject in need thereof, to immunomodulate the subject's immune system. Immunomodulating the immune system promotes immune health in a subject, restoring a balanced immune response to those in need, or maintaining balance, for instance allowing proinflammation in areas of healing while minimizing/modulating responses such as a cytokine storm response, and thus avoiding additional immune weaknesses, and strengthening the immune response and overall immune health of the subject. Immunomodulation may for instance promote immune health in a subject, adjust the immune system and its responses and/or help it self-regulate as needed by the subject.

The below definitions and discussion are intended to guide understanding but are not intended to be limiting with regard to other disclosures in this application. References to percentage (%) and ratios in compositions of the present invention refers to the % by weight of a given component to the total weight of the composition being discussed or ratios of the weight of specified substances, also signified by "w/w" or "wt/wt", unless stated otherwise.

A "curcumin extract" according to the present invention is an extract of turmeric root containing curcumin (diferuloylmethane). In an embodiment, a curcumin extract of the present invention includes at least 1-100% curcumin (wt/wt); 2-95% curcumin (wt/wt); 10-95% curcumin (wt/wt); 20-95% curcumin (wt/wt); 40-50% curcumin (wt/wt); 50-60% curcumin (wt/wt); 60-70% curcumin (wt/wt); 70-80% curcumin (wt/wt) including for instance 75-78% curcumin (wt/wt); 80-97% curcumin (wt/wt); 90-100% curcumin (wt/wt), including for instance 93-97% curcumin (wt/wt); 95% curcumin (wt/wt). A curcumin extract may include a variety of curcuminoids, including for instance curcumin, tetrahydrocurcumin, demethoxycurcumin, bisdemethoxycurcumin, curcumin esters (which may function as prodrugs), and mixtures thereof. In an embodiment, a composition of the present invention may include a combination of curcumin and a metabolite of curcumin, tetrahydrocurcumin. In an embodiment, the curcumin extract is standardized. In an embodiment, a curcumin extract of this invention is in solid form such as a powder, or in a liquid or semi-liquid form. See for instance Tables 1 and 2 for examples of a curcumin extract used in the present invention.

According to an embodiment of this invention, a curcumin extract is formulated and delivered to the bloodstream and tissues of the body by a delivery system such as solid lipid curcumin particle (SLCP) technology. In an embodiment, curcumin optimized for delivery by SLCP technology is Longvida®. In an embodiment, curcumin optimized for delivery, by SLCP or another technology, is not Longvida®. Optimized curcumin according to the present invention delivers non-glucuronidated curcumin (and in an embodiment non-sulfated curcumin) to the tissues and blood of the body, including for instance via lymphatic transport and by allowing the curcumin to cross the blood-brain-barrier. [See for instance Eidenberger et al., "*Investigation of the Lymphatic Transport of Solid-Lipid Curcumin Particles (Longvida®) in Comparison to Curcumin Extract in Rats*" in $252^{nd}$ ACS National Meeting, Philadelphia, Pa.: 55 (2016)]. U.S. Pat. No. 9,192,644 is incorporated by reference into this application for the purpose of describing optimized curcumin and its preparation.

For instance, optimized curcumin may be prepared with mole fractions of stearic acid (0.710), lecithin (0.210), taurocholate (0.069), curcumin (0.011), with surfactants stirred into 75° C. water and then the water-surfactant solution added to the melted lipid at 75° C. and then homogenized into an emulsion, typically 18,000 to 30,000 rpm for 70-150 seconds. The dispersed lipid phase of the emulsion is solidified by dispersing 1 mL emulsion aliquots through a narrow gauge needle into near ice cold water (about 2° C.), at a ratio of 1:20 warm micro-emulsion:cold water, to produce solid lipid nanoparticles. The solid lipid nanoparticles are washed three times with distilled water and sterilized and stored sterile at 4° C.

Solid Lipid Nanoparticles (SLN) Preparation
Starting Formula.

Stearic Acid mole fraction 0.710; lecithin mole fraction 0.210; taurocholate mole fraction 0.069; curcumin or other curcuminoid varies stepwise around mole fraction 0.011. Stearic acid lipid is maintained at ~75° C. to melt completely. Separately, double distilled water is heated to 75° C. Typically, surfactants are added to the water under magnetic stirring and allowed to equilibrate at 75° C. The water-surfactant solution is added to the melted lipid and allowed to equilibrate at 75° C. The IKA Ultra-Turrax T 18 rotor-stator homogenizer is then used to achieve adequate mixing, typically 18,000-30,000 rpm for 70-150 sec. Once mixed, the dispersed lipid phase of the emulsion is solidified in order to produce the solid lipid nanoparticles by dispersing through a narrow gauge needle 1 ml emulsion aliquots into continuously stirred near ice cold water (~2° C.) at a ratio of 1:20 (warm micro-emulsion:cold water). The final product is washed three times with distilled water and filter sterilized with an Amicon Diaflo apparatus with YM100 membranes (cut off 100 000 Dalton) and stored sterile at 4° C. until delivery by gavage. Multiple lipid nanoparticle samples can be prepared from one micro-emulsion batch.

In an embodiment, optimized curcumin may be administered orally. Optimized curcumin has improved oral bioavailability over regular curcumin. In an embodiment, optimized curcumin may be administered parenterally. Optimized curcumin for parenteral administration may be particles sized approximately 100 nm, for instance in the range of 50-150 nm; for oral administration, optimized curcumin particles may be sized larger, for instance approximately 50-500 nm. In an embodiment, for parenteral administration, the polydispersity of optimized curcumin is about 0.10.

A "pomegranate extract" according to the present invention is prepared by extracting chemicals from a pomegranate. In an embodiment, the pomegranate extract is standardized. The pomegranate extract comprises at least 2% (w/w) punicalagins, up to 100% punicalagins. The pomegranate extract also comprises free ellagic acid. In an embodiment, the content of the free ellagic acid is such that the ratio of punicalagins:free ellagic acid (w/w) is in the range of 10:1 to 35:1. In an embodiment, the total phenol content of a pomegranate extract of the invention is at least 5% (w/w) (expressed as gallic acid equivalent). The solubility of a pomegranate extract in water is at least 3% (w/w), for instance, 30 g pomegranate extract/liter. In an embodiment, the pomegranate extract contains minimal or no traces of organic solvents such as methanol, ethanol, isopropanol, which are commonly employed in purification steps to prepare a pomegranate extract. In an embodiment, said minimal or no traces of organic solvents are 1 ppb or less. An example of a pomegranate extract according to this invention is Pomella®. A formulation of proprietary pomegranate extract according to the present invention may be designed to provide high levels (e.g. at least 20%) of ellagitannins, in particular punicalagins. In an embodiment, a pomegranate extract of this invention is in solid form such as a powder, or in a liquid or semi-liquid form. See for instance Tables 1 and 2 for examples of a pomegranate extract used in the present invention.

In an embodiment, a pomegranate extract of this invention comprises at least 5% (w/w) punicalagins, for instance in the range of 5-50% (w/w) punicalagins, including for instance 30-50% (w/w) punicalagins, 35-45% (w/w) punicalagins, 40-50% (w/w) punicalagins, 40-45% (w/w) punicalagins, and other ranges as provided throughout this application; and the total phenol content is at least 10%-50% (w/w) (expressed as gallic acid equivalent), including for instance 20% or 30%, and other values within the range. The solubility of the extract in water is at least 3%, as described above, and in an embodiment, the extract has a content of residual organic solvents of 0-1 ppb.

In an embodiment, an enzyme capable of hydrolyzing punicalagins and/or punicalins to ellagic acid is used in a pomegranate extract of this invention. In an embodiment, a pomegranate extract of this invention has a ratio of punicalagins:ellagic acid (% w/w) in the range of 10:1 to 35:1. In an embodiment, a pomegranate extract of this invention includes 20-50% (w/w) ellagic acid, in an embodiment 30-45% (w/w) ellagic acid, in an embodiment, 40% (w/w) ellagic acid.

In an embodiment, a pomegranate extract of the present invention comprises polyphenolic compounds. In an embodiment, the polyphenolic compounds include or are punicalagins (PA), ellagic acid (EA), urolithins such as urolithin A (UA), or a combination thereof. In an embodiment, a composition of the present invention comprises pomegranate extract, which comprises a combination of PA and EA and optionally Urolithins, such that the extract and/or composition comprises a combination of PA and EA in amount of about 3% to about 95% by weight. In an embodiment, the combination of PA and EA is from about 10% to about 90% PA and up to 10% EA by weight. In an embodiment, the combination of EA and PA is from about 10% to about 90% EA and up to 10% PA by weight. In an embodiment, the combination of PA and EA is from about 20% to about 50% PA and about 0.5% to about 5% EA by weight. In an embodiment, the combination of EA and PA is from about 20% to about 50% EA and about 0.5% to about 5% PA by weight. In an embodiment, the combination of PA and EA is from about 10% to about 50% PA and about 2.0-3.0% EA by weight. In an embodiment, the combination of EA and PA is from about 10% to about 50% EA and about 2.0-3.0% PA by weight. In an embodiment, the combination of PA, EA, and Urolithin(s) is about 3% to about 95% by weight. Also in an embodiment, the combination of PA, EA, and Urolithin(s) is from about 10 to about 50% PA, about 0.5% to about 5% EA, and 0.5 to 20% Urolithin by weight. As urolithins such as Urolithin A are gut microbial metabolites of Pomella punicalagins, and their metabolites, urolithins may not be present in Pomella®.

A pomegranate extract according to the present invention may be prepared for instance by blending all or part of a pomegranate fruit in water or aqueous solution, and removing remaining solids. In an embodiment, after removing solids, the blended solution is poured over a resin such as a polymeric resin such as XAD-16 resin so that ellagitannins such as punicalagins and punicalins adsorb to the resin, and then are eluted from the resin for instance by methanol or ethanol, and the methanol or ethanol then removed for instance by evaporation. In an embodiment, the pH before, during, or after blending is about 1-2.5.

U.S. Pat. Nos. 7,638,640; 7,897,791; and 7,919,636 describe examples of pomegranate extracts and their preparation according to the present invention, and are each incorporated by reference herein for the purpose of describing preparation methods and products.

A "composition" according to the present invention comprises, consists essentially of, or consists of a combination of curcumin extract and pomegranate extract. In an embodiment, a combination of curcumin extract and pomegranate extract of this invention is a blend of the two extracts. In an embodiment, a composition of this invention comprises a synergistic combination of curcumin extract and pomegranate extract. Such a composition may be referred to as a synergistic composition of this invention. In an embodiment, and as needed without being bound by theory, the synergies of the bioactive compounds of the curcumin extract and pomegranate extract provide a synergistically improved immune response as compared with curcumin extract or pomegranate extract alone. In an embodiment, a composition of the present invention comprises 5-30% curcuminoids and 3-50% punicalagins.

In an embodiment, a composition of this invention is a solutions dispersible complex of (i) lipid coated curcumin or curcumin micelles, and (2) pomegranate polyphenols. In an embodiment, a pomegranate extract of this invention is soluble in water, and lipid-coated curcumin or curcumin micelles are partly soluble in water. In an embodiment, when the curcumin and pomegranate extracts are combined, for instance blended, together, the lipid coated curcumin or curcumin micelles do not change if they undergo grinding, mixing, milling, encapsulation, and/or granulation/regranulation. In an embodiment, a composition of the present invention may be prepared combining the curcumin extract and pomegranate together for instance by grinding, mixing, milling, encapsulation, and/or granulation/regranulation, for instance per known techniques. In an embodiment, the particle size of a composition of this invention may be the particle size resulting from grinding, mixing, and/or granulating curcumin and pomegranate extracts, or may be reduced for instance by further grinding. Without being bound by theory, reducing particle size according to this invention may improve dispersion and solubility. In an embodiment, a composition and/or combination of this invention is in powdered or other solid form. In an embodiment, a composition and/or combination of this invention is in liquid or semi-liquid form.

Without being bound by theory, a blend of the two extracts into a composition of this invention appears to enhance solubility. Both curcumin and punicalagins are polyphenolic, however, the combination of polyphenols does not mean they will work together. Research has shown that many times polyphenols will cancel each other out. However, in a composition of the present invention, such as a blend of the two extracts, punicalagin and curcumin both have anti-inflammatory potential, however, it appears that when combined synergy from the combination of the extracts occurs, with actions further down the cellular pathway and mRNA's with impact on several immune system pathways, including improving those associated with responding to cytokine storm, stimulating innate immune pathways, and stimulating host-pathogen pathways, whether the immune system is impacted from stress from exercise or from pathogens.

In an embodiment, a combination of curcumin extract and pomegranate extract of the present invention comprises not less than 10% w/w total curcuminoids, not less than 5% punicalagins, and not less than 20% total pomegranate polyphenols. In an embodiment, a combination of the present invention comprises not less than 11.5% w/w total curcuminoids, not less than 15% punicalagins, and not less than 25% total pomegranate polyphenols. In an embodiment, a composition of the present invention comprises 20-30% total pomegranate polyphenols, 3-5% bis and dimethoxy curcumin, 12-13% curcumin, 9-30% punicalagins, 15-20% stearic and palmitic acid, 2% ascorbyl palmitate, 12-18% dextrin, 20% polysaccharides, and 7-8% phosphatidylcholine (PC). In an embodiment, a composition of the present invention is Restoridyn®, comprising 20-32% total pomegranate polyphenols, 3-5% bis and dimethoxy curcumin, 12-13% curcumin, 9-30% punicalagins, 10-16% stearic and palmitic acid, 1-2% ascorbyl palmitate, 10-16% dextrin, 15-20% polysaccharides, and 1-3% lecithin (phosphatidylcholine (PC)). In another embodiment, a composition of this invention comprises 24-30% total pomegranate polyphenols, 3-5% bis and dimethoxy curcumin, 12-13% curcumin, 9-30% punicalagins, 15-20% stearic and palmitic acid, 2% ascorbyl palmitate, 12-18% dextrin, 20% polysaccharides, and 7-8% phosphatidylcholine (PC). In another embodiment, a composition of the present invention, for instance in powdered form, comprises 13.52% curcuminoids, 1.01% ascorbyl palmitate, 2.16% phosphatidylcholine (lecithin), 16.31% dextrin, 1.15% silica, 15.85% stearic acid and palmitic acid, 15% punicalagin, 20% total pomegranate polyphenols (or total polyphenols overall), 15% polysaccharides and carbohydrates.

In an embodiment, a composition of the present invention comprises equal parts (50% w/w) of the curcumin and pomegranate extracts in Table 1, in powdered form, blended together:

TABLE 1

| Composition | |
|---|---|
| Curcumin Extract | Pomegranate Extract |
| 25-35% *Curcuma longa* extract | 100% *Punica granatum* extract of fruit |
| 10-20% lecithin | Standardization: not less than 30% punicalagins and not less than 50% total polyphenols |
| 19-35% stearic acid or salts of stearic acid | |
| 19-27% maltodextrin | |
| 1-3% ascorbyl palmitate | |
| 0.3-3% silicon dioxide | |
| Standardization: Not less than 23.00% total curcuminoids | |

In an embodiment, the Curcumin Extract above is Longvida® and the Pomegranate Extract above is Pomella®. In an embodiment, the composition above has a bio-marker specification of not less than 10% total curcuminoids and not less than 10% punicalagins. Composition component lecithin may be for instance sunflower or soy lecithin. Compositions of the present invention include compositions comprising the standards described above.

In an embodiment, a composition of the present invention comprises equal parts of the curcumin and pomegranate extracts of Table 2, a solution dispersible formulation in powdered form, blended together:

TABLE 2

| Composition | |
|---|---|
| Curcumin Extract | Pomegranate Extract |
| 20-35% *Curcuma longa* extract | 100% *Punica granatum* extract of fruit |
| 19-35% maltodextrin | Standardization: not less than 10% punicalagins and not less than 40% total polyphenols |
| 1-35% stearic acid, DHA, or calcium stearate | |
| 10-20% lecithin | |
| 1-4% ascorbyl palmitate | |
| 0.3-3% silicon dioxide | |
| Standardization: Not less than 21.00% total curcuminoids | |

In an embodiment, the Curcumin Extract above is Longvida® and the Pomegranate Extract above is Pomella®. In an embodiment, the composition above has a bio-marker specification of not less than 10% total curcuminoids, not less than 3% punicalagins, and not less than 20% total polyphenols. Composition component lecithin may be for instance sunflower or soy lecithin. Compositions of the present invention include compositions comprising the standards described above.

In an embodiment, a composition of the present invention is in solid form and includes a particle size of NLT 95% through 20 mesh and NMT 45% thru 100 mesh or NLT 98% through 100 mesh.

A composition according to the present invention may be administered in a daily dose of a combination of a curcumin extract and a pomegranate extract. In an embodiment, a daily dose includes at least 50 mg of a pomegranate extract of the present invention and at least 50 mg of a curcumin extract of the present invention. In an embodiment, in a human, the daily dose includes at least 50 mg to 20 g of a curcumin extract, including for instance 80 mg, 100 mg, 200 mg, 400 mg, 500 mg, 800 mg, 1000 mg, 1500 mg, 2000 mg, and 4000 mg of curcumin extract, and any intervening amounts or ranges therein, daily; and includes at least 50 mg to 5 g of a pomegranate extract, including for instance 150 mg, 200 mg, 300 mg, 400 mg, 500 mg, 600 mg, 800 mg, 1000 mg, 1500 mg, 2000 mg, and 4000 mg of pomegranate extract, and any intervening amounts or ranges therein, daily.

Combinations of a pomegranate extract and a curcumin extract of the present invention may include amounts in the ratios described below. A combination and/or composition of the present invention may comprise a ratio in a range of 1:5 to 5:1 curcumin:pomegranate. For instance, this range may be directed to a ratio of 1 part curcumin to 1 part, 2 parts, 3 parts, 4 parts, or 5 parts pomegranate; 2 parts curcumin to 1 part, 2 parts, 3 parts, 4 parts, or 5 parts pomegranate; 3 parts curcumin to 1 part, 2 parts, 3 parts, 4 parts, or 5 parts pomegranate; 4 parts curcumin to 1 part, 2 parts, 3 parts, 4 parts, or 5 parts pomegranate; or 5 parts curcumin to 1 part, 2 parts, 3 parts, 4 parts, or 5 parts pomegranate. Similarly, this range may be directed to a ratio of 1, 2, 3, 4, or 5 parts curcumin to 1 part pomegranate extract; 1, 2, 3, 4, or 5 parts curcumin to 2 parts pomegranate extract; 1, 2, 3, 4, or 5 parts curcumin to 3 parts pomegranate extract; 1, 2, 3, 4, or 5 parts curcumin to 4 parts pomegranate extract; or 1, 2, 3, 4, or 5 parts curcumin to 5 parts pomegranate extract. Ratios of the present claims may include fractional parts, such as 1.1, 1.2, 1.3, 1.4, 1.5, 1.6, 1.7, 1.8, 1.9; 2.1, 2.2, 2.3, 2.4, 2.5, 2.6, 2.7, 2.8, 2.9; and so forth. In an embodiment, a composition of this invention is Restoridyn® (Verdure Sciences, Noblesville IN), providing equal parts (1:1 ratio of the present invention) of an optimized curcumin extract (Longvida®; Verdure Sciences, Noblesville IN) and a pomegranate extract (Pomella®; Verdure Sciences, Noblesville IN). In an embodiment, a combination of the present invention is a 2:3 blend of curcumin extract such as Longvida®:pomegranate extract such as Pomella®. In an embodiment, a combination of the present invention is a 2:3 blend of pomegranate extract such as Pomella®:curcumin extract such as Longvida®.

In an embodiment, the combination of curcumin extract and pomegranate extract of the present invention is administered orally as a prebiotic composition to improve gut health. Without being bound by theory, gut health is improved because the richness in punicalagins can stimulate the growth of colon bacteria, combined with a very low content of free ellagic acid, which may inhibit microbial growth. A composition of the present invention may be a prebiotic therefore. As mentioned above, in a pomegranate extract of the present invention, the ratio of punicalagins: free ellagic acid (w/w) is in the range of 10:1 to 35:1. For use in the present invention, such as a prebiotic, in an embodiment, the ratio of punicalagins:free ellagic acid (w/w) is about 25:1 to about 35:1.

A pomegranate extract of this invention does not include simple pomegranate juice. The commercially available best pomegranate juice contains between 2400-4000 mg/L total polyphenols (expressed as gallic acid equivalent) including punicalagins content in the range of 500-2000 mg/L. Said juice has a Brix of 16 and can be subsequently concentrated about 5 times thereby in punicalagins content, never reaching more than 10 g/L (1% w/w). Regarding the ratio of punicalagins/free ellagic acid in pomegranate juice, such did not exceed 8:1, and is further reduced due to the hydrolysis suffered by complex ellagitannins such as punicalagins, with the subsequent liberation of free ellagic acid.

In an embodiment, a composition of the present invention is a prebiotic composition, and/or a dietary supplement. Delivery systems and formulations for curcumin or other substances including components of a pomegranate extract of this invention include lipid micelles, microencapsulated oils, solid lipid nanoparticles, gel, capsules, powders and other solid forms, and liquid forms.

In the present application, an "effective amount" of a composition of this invention refers to an amount of curcumin extract and pomegranate extract combined needed to reach a subject's bloodstream and/or tissues and to improve the immune system of the subject's body, for instance by increasing the subject's immune response (e.g. bodily, or total body immune response, or a regionalized or localized response) or increasing the body's ability to respond to foreign antigens or microbes and the like. In an embodiment, an effective amount of curcumin extract and pomegranate extract combined is a daily dose including at least 50 mg to 20 g of a curcumin extract such as the optimized curcumin extract Longvida®, including for instance 80 mg, 100 mg, 150 mg, 200 mg, 300 mg, 400 mg, 500 mg, 600 mg, 800 mg, 1000 mg, 1500 mg, 2000 mg, and 4000 mg of curcumin extract, and any intervening amounts or ranges therein, daily; and at least 50 mg to 20 g of a pomegranate extract, including for instance 80 mg, 100 mg, 150 mg, 200 mg, 300 mg, 400 mg, 500 mg, 600 mg, 800 mg, 1000 mg, 1500 mg, 2000 mg, and 4000 mg of a pomegranate extract such as Pomella®, and any intervening amounts or ranges therein, daily. In an embodiment, an effective amount of curcumin is about 100-2000 nM (0.1-2 micromolar) curcumin in blood or tissue. In an embodiment, plasma levels of curcumin are about 0.25-0.5 micromolar.

A "dietary supplement" according to the present invention refers to a composition comprising curcumin extract and pomegranate extract of the present invention which is administered as an addition to a subject's diet, which is not a natural or conventional food, and which when administered is delivered to the bloodstream and/or bodily tissues of a subject and interacts therewith to effectively increase an immune response over a period of time. In an embodiment, a dietary supplement containing an effective amount of a composition according to the present invention is administered orally. In an embodiment, the dietary supplement is administered daily to a subject; in an embodiment, the dietary supplement is administered daily for 30 days or more, or for another period of time. A dietary supplement may be formulated into various forms, as discussed throughout this application. In an embodiment, the subject self-administers a dietary supplement of the present invention.

A composition of the present invention, including a dietary supplement of the present invention, may for instance be in the form of a sachet, tablet, capsule, powder, liquid, lozenge, chew, gummy, transdermal, injectable, etc. using standard excipients and formulation techniques in the industry. For instance, as shown in Tables 1 and 2, a composition of this invention may include lecithin, phosphatidylcholine (including lecithin as phosphatidylcholine), DHA, stearic acid/stearate, palmitic acid, dextrin, maltodextrin, ascorbyl palmitate, polysaccharides, carbohydrates, silica, and/or silicon dioxide, for instance in the ranges noted in the Tables. In an embodiment, a composition is formulated for oral administration, however, other forms of administration including injection, inhalation, and the like, may be used in the present methods.

"Administering" or "administration" of a composition of the present invention or the like refers to introducing the composition into the body of the human or other mammalian subject, so that the curcumin and pomegranate extract components are delivered to the subject's bloodstream and/or tissues, exposing the tissues to the curcumin and pomegranate extracts, so that the curcumin and pomegranate extracts may change the tissues from their pre-administration state as indicated throughout this application. In an embodiment, administration to a subject is oral, for instance as discussed throughout this application. Administration of a composition according to this invention may be for a period of time of 1 day, 1-7 days, 1-4 weeks, 1 month, 27-35 days, 2 months, or longer.

Supporting immune health according to the present invention, and the like, refers to helping the immune system of the subject's body maintain a healthy status. Improving immune health refers to helping the immune system of the subject's body respond to an invader in a superior manner than pre-administration, for instance by increasing the subject's immune response to a normal healthy state or to an enhanced healthy state (e.g. bodily, or total body immune response, or a regionalized or localized response) or increasing the body's ability to respond to foreign antigens or microbes and the like. Supporting and/or improving immune health may include for instance making necessary components for an immune response available or more plentiful, including but not limited to protein or RNA availability, so that an immune response may proceed for instance in optimal time in response to an invader; or otherwise may refer to preparing the subject's body for an immune challenge.

"Health" according to the present invention generally refers to systems, organs, tissues including the blood and bloodstream of the subject, and/or cells, that are functioning properly, and that are regular and intact.

An immune-related disorder according to the present invention refers to an abnormally low immune response in a subject, and an immune-related disease refers to a decrease in the body's ability to fight invaders, causing the subject to be vulnerable to invaders. In an embodiment, the immune-related disorder or disease refers to an abnormally high, or overactive, immune response in a subject; or an excessive immune response in a subject. In an embodiment, the disease or disorder treated according to the present invention is an auto-immune disease.

Treating or preventing an immune disease or disorder according the present invention, or a symptom thereof, refers to improving the immune system of the subject's body to overcome the disease or disorder, or a symptom of the disease or disorder, for instance by increasing the subject's immune response (e.g. bodily, or total body immune response, or a regionalized or localized response) or increasing the body's ability to respond to foreign antigens or microbes and the like, in a subject having an immune-related disorder or disease (i.e. treating the disease), and/or in a subject at risk for the disease or disorder or that may develop the disease or disorder (i.e. preventing the disease). In an embodiment, a composition of the present invention may be used as an antiviral agent, immunostimulant, immunosuppressant, to treat sepsis, to treat cardiovascular diseases, and to treat respiratory diseases.

In an embodiment, reducing risk of infection according to this invention may include treating or preventing a disease cause by a virus or bacteria, for instance such as treating or preventing infection with SARS-CoV2 virus, or COVID-19.

A subject of the present invention is in an embodiment a human, but may be a mammal, including for instance a horse, cat, or dog. Individuals described in Table 3 are examples of subjects of the present invention. A healthy subject has normal bodily functions for instance falling within normal ranges of a medical blood analysis, subjectively feels in good health, and/or is not currently suffering from an infection. A sick or unwell subject has abnormal bodily functions such as elevated white blood cell counts or other signs of infection or other illness for instance per a medical blood analysis, subjectively does not feel in good health, and/or currently has an infection.

The present invention may be further understood in connection with the following Examples and embodiments. The following non-limiting Examples and embodiments described throughout this application are provided to illustrate the invention.

Example 1

Materials & Methods

Experimental Design

The present study was conducted using two experiments that included a similar group of subjects (trained runners), but different sets of outcome measurements. Experiment One involved the use of Luminex bead-based methods to measure changes in protein and RNA biomarkers that have been shown to be involved in the inflammatory process and muscle injury (Supplementary Table 1). The bead-based RNA biomarker panel (mRNA and lncRNA, 40 plex) was designed to complement the proteins measured (Supplementary Table 2). Experiment Two involved the use of a commercially available NanoString® array to measure and expand the set of RNA biomarkers (>500 plex) (Supplementary Table 3). Supplementation conditions (i.e. administration of the combination of curcumin extract and pomegranate extract and control) and blood sample collection time points (i.e. pre-race, 4-hour post-race, and 24-hour post-race) were identical between the two experiments.

Subjects orally self-administered a 50-50 blend of optimized curcumin (Longvida®) and pomegranate extract (Pomella®); (together, Restoridyn®; Verdure Sciences; Noblesville IN). The optimized curcumin (Longvida®) was a solid lipid curcumin particle formulation designed to improve bioavailability of at least unglucuronidated curcumin. The formulation of pomegranate extract (Pomella®) was designed to provide high levels of ellagitannins, in particular punicalagins. The composition administered to the subjects comprised 20-32% total pomegranate polyphenols, 3-5% bis and dimethoxy curcumin, 12-13% curcumin, 9-30% punicalagins, 10-16% stearic and palmitic acid, 1-2% ascorbyl palmitate, 10-16% dextrin, 15-20% polysaccharides, and 1-3% lecithin (phosphatidylcholine (PC)).

During the first 26 days, subjects were supplemented daily with 1000 mg/d Restoridyn® and an additional booster dose (1000 mg/d of Restoridyn®) within one hour of completing a run longer than 6 miles (6±2 total booster doses consumed). At day 27 (3 days prior to the half-marathon race), subjects increased their daily dosage to 2000 mg/d and discontinued the use of booster doses. The subjects continued this higher dose through the 24-hour post-race blood sample (day 31). The dosage was doubled on days 27-31 to manage the expected increase in muscle injury from the half-marathon race which is consistent with previous laboratory-based studies [McFarlin et al., *Reduced inflammatory and muscle damage biomarkers following oral supplementation with bioavailable curcumin. BBA Clin*, 5: 72-8 (2016); Nicol et al., *Curcumin supplementation likely attenuates delayed onset muscle soreness (DOMS) Eur J Appl Physiol* 115(8): 1769-77(2015)]. Venous blood samples were collected pre-race (PRE), 4-hour post-race (4 H), and 24-hour post-race (24 H). These sample time points were selected to focus on the acute response to a half-marathon race [Gary et al., *Combined bead-based multiplex detection of RNA and* protein biomarkers: Implications for understanding the time course of skeletal muscle injury and repair Methods 158: 92-96 (2019); Tanner et al., Combining single molecule counting with bead-based multiplexing to quantify biological inflammation time course following skeletal muscle injury Methods 158:77-80 (2019)].

Subjects

Prior to any research being conducted our study was reviewed and approved by the UNT Institutional Review Board (IRB). All study procedures were conducted in accordance with the Declaration of Helsinki. Subjects gave written and verbal consent to participate. Prior to enrollment, subjects were screened for contraindications to exercise and when necessary received medical clearance from a physician to participate. Subjects were stratified to one of two supplement conditions: curcumin+pomegranate (the combination of curcumin extract and pomegranate extract; Restoridyn®; N=8) or open-label control (N=10). Qualified subjects were currently training for a half-marathon race, had no significant medical history (i.e. smoking, chronic disease, etc.) and had not consumed curcumin/turmeric or pomegranate containing foods or nutritional products within the past 2-months. Body composition was measured using dual-energy x-ray absorptiometry (DEXA). Subject characteristics are reported in Table 3.

TABLE 3

Subject Characteristics

| Gender | Control<br>Male = 5, Female = 5 | Treatment<br>Male = 5, Female = 3 |
| --- | --- | --- |
| Age (yr) | 38.7 ± 6.0 | 37.8 ± 6.4 |
| Height (cm) | 176.6 ± 10.4 | 177.1 ± 7.1 |
| Weight (kg) | 75.6 ± 14.7 | 81.0 ± 14.5 |
| Body Fat (%) | 27.1 ± 10.8 | 26.7 ± 12.1 |
| Body Mass Index (BMI) | 24.0 ± 2.7 | 25.7 ± 3.3 |

Data reported as mean ± standard deviation. No significant difference between conditions.

Blood Collection & Isolation:

Whole blood was collected from a peripheral arm vein into Z-serum separator vacuettes (Greiner Bio-One, Kremsmünster, Austria) or PAXgene® RNA stabilizing vacutainers (PreAnalytiX, Hombrechtikon, Switzerland). According to manufacturer guidelines, PAXgene® tubes were mixed by inversion and stored at −20° C. for 24-hour, before being transferred to −80° C. for long-term storage. Individual serum aliquots were isolated by centrifugation and frozen (−80° C.) until analysis.

Experiment One: Bead-Based Analysis

Previously frozen serum samples were analyzed in duplicate for protein concentration using commercially available bead-based kits (Supplementary Table 1): high sensitivity cytokines (Milliplex®; Millipore-Sigma; St. Louis, MO; 21-cytokines), soluble cytokine receptors (Milliplex®; Millipore-Sigma; 14-soluble receptors), and myokines (Milliplex®; Millipore-Sigma; 15-myokines). All analysis was conducted according to manufacture guidelines, raw data was collected using a bead-based multiplex analyzer (FlexMAP 3D™). PAXgene® blood was processed and analyzed for RNA expression in duplicate using custom extraction and bead-based gene expression kits (QuantiGene; ThermoFisher Scientific; Santa Clara, CA; 40-RNA) (Supplementary Table 2). Sample processing and analysis was completed according to the manufacture guidelines. After the assay was complete, raw data was collected using a bead-based multiplex analyzer (FlexMAP 3D™; Luminex Corp; Austin, TX).

Experiment One: Statistical Analysis

Protein biomarker concentrations were calculated using commercially available software (Milliplex® Analyst v5; MilliporeSigma) that automatically calculated unknown values compared to a standard curve. $R^2$ for all standard curves were >0.98. RNA data was normalized by dividing the median fluorescent intensity for a given RNA target by the geometric mean of the control RNA median fluorescent intensity. Data were cleaned and analyzed using R (version 3.6.0). The statistical analysis of the pairwise comparisons ("Curcumin+Pomegranate" versus "Control") was done with the ggpubr package (version 0.2) and a Welch t-test. The data was visualized using the ggplot2 package (version 3.1.0). To visualize significantly regulated proteins/RNAs volcano plots were used with a fold-change cutoff of 1.2 and a p-value cutoff of 0.05 displayed as dashed lines. Analyte label saturation indicates test-power where full saturation indicates >0.8 test-power.

Experiment Two: Nanostring Analysis

Total RNA was extracted from frozen PAXgene® blood using a commercial isolation kit (PAXgene® Blood miRNA kit; PreAnalytiX, Hombrechtikon, Switzerland) using an automated system (QIAcube; Qiagen, Hilden, Germany). Isolated total RNA was analyzed using a Human Immunology Panel (nCounter; Nanostring, Seattle, WA, 594-RNA) (Supplementary Table 3), raw data was acquired using a multiplex imaging system (Sprint Profiler; NanoString®, Seattle, WA). Samples were processed according to the manufacture guidelines. The raw data included total counts of each target mRNA present in each sample.

Experiment Two: Statistical Analysis

Quality control and assay performance analyses were conducted on all raw mRNA data using nSolver software (NanoString®) with the nCounter Advanced analysis module (v.2.0.115). Target mRNA data was normalized to internal control/housekeeping mRNA (TUBB, GUSB, TBP, PPIA, SDHA, POLR1B, ALAS1, HPRT1, EEF1G, RPL19, ABCF1, G6PD, POLR2A, and GAPDH). Normalized data were cleaned and analyzed using R (version 3.6.0). The statistical analysis of the pairwise comparisons ("Curcumin+Pomegranate" versus "Control") was done with the ggpubr package (version 0.2) and a Welch t-test. The data was visualized using the ggplot2 package (version 3.1.0). To visualize significantly regulated mRNA, we used volcano plots with a fold-change cutoff of 1.2 and a p-value cutoff of 0.05 displayed via dashed lines. Analyte label saturation indicates test-power where full saturation indicates >0.8 testpower.

Results

Experiment One: Protein Analysis

Volcano plots were generated based on log 2 median ratios and negative decadic logarithm of the p-value to identify target protein abundances that were either increased, decreased, or not altered when comparing the supplement to the control (FIG. 1). Additional box and whisker plots of the absolute concentration of the proteins in the blood were generated to confirm proteins that significantly changed with supplement relative to control (FIG. 2; from top, row 1: BDNF, IL-10, IL-13, IL-4, IL-8; row 2: ITAC, MIP-1alpha, MIP-3alpha, sgp130, sIL-2Ralpha; row 3: TNF-alpha). At PRE, prior to the race, IL-10, TNF-alpha, IL-8, ITAC, IL-13, MIP-1alpha, and MIP-3alpha abundance were found significantly increased in the supplement group when compared to the control group, while BDNF and sgp130 were found in significantly lower levels. At 4 H, 4 hours post-race, IL-10 was found in higher levels and BDNF was found in lower levels and at 24 H, 24 hours post-race, IL-4, sIL-2Ralpha, and IL-8 abundance were increased when supplement was compared to the control group. There were no proteins found in lower levels at 24 H.

Experiment One: Bead-Based RNA Analysis

Figure 3:
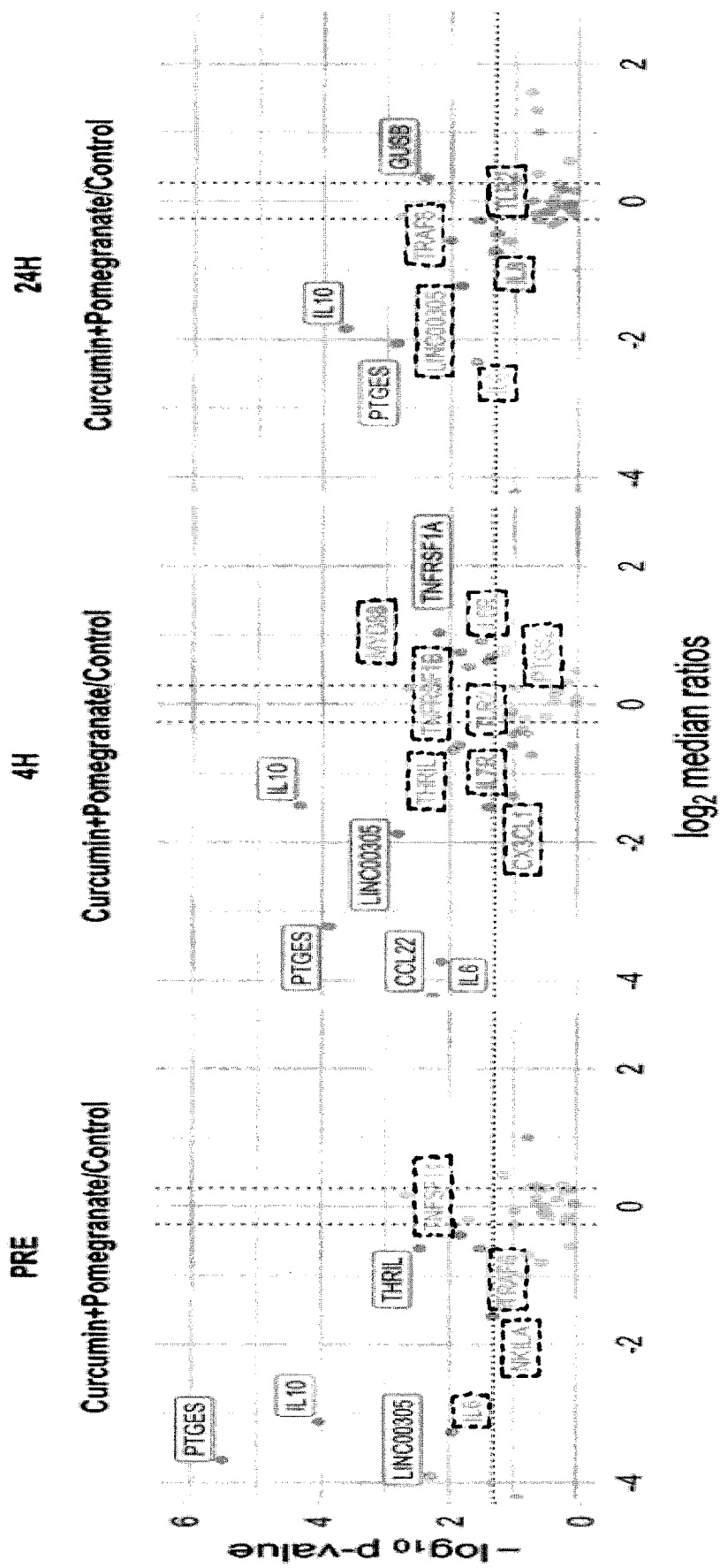
FIG. 3 shows a volcano plot showing RNA relating to inflammation that significantly increased or decreased in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

Volcano plots were generated based on log 2 median ratios and negative decadic logarithm of the p-value to identify bead-based RNA that were either up-regulated, down-regulated, or not changed with supplement compared to control (FIG. 3). Additional box and whisker plots were generated to confirm RNA that significantly changed with supplement (FIG. 4; from top, row 1: CCL22, CX3CL1, GUSB, IL10, IL6; row 2: IL6R, IL7R, IL8, LINC00305, MYD88; row 3: NKILA, PTGES, PTGS2, THRIL, TLR2; row 4: TNFRSF1A, TNFRSF1B, TNFSF14, TRAF6). At PRE, no RNA was significantly up-regulated but IL-6, IL-10, PTGES, THRIL, LINC00305, TNFSF14, TRAF6, and NKILA were significantly down-regulated with supplement compared to control. At 4 H, the RNA that were significantly up-regulated were MYD88, TNFRSF1B, TNFRSF1A, TLR2, IL-6R, and PTGS2; the down-regulated RNAs were IL-6, IL-10, PTGES, THRIL, LINC00305, CCL22, IL-7R, and CX3CL1 with supplement compared to control. At 24 H, the RNA that was significantly up-regulated was GUSB while IL-6, IL-10, PTGES, TRAF6, LINC00305, IL-8, and TLR2 were down-regulated with supplement compared to control.

Experiment Two: Nanostring mRNA Analysis

Figure 5:
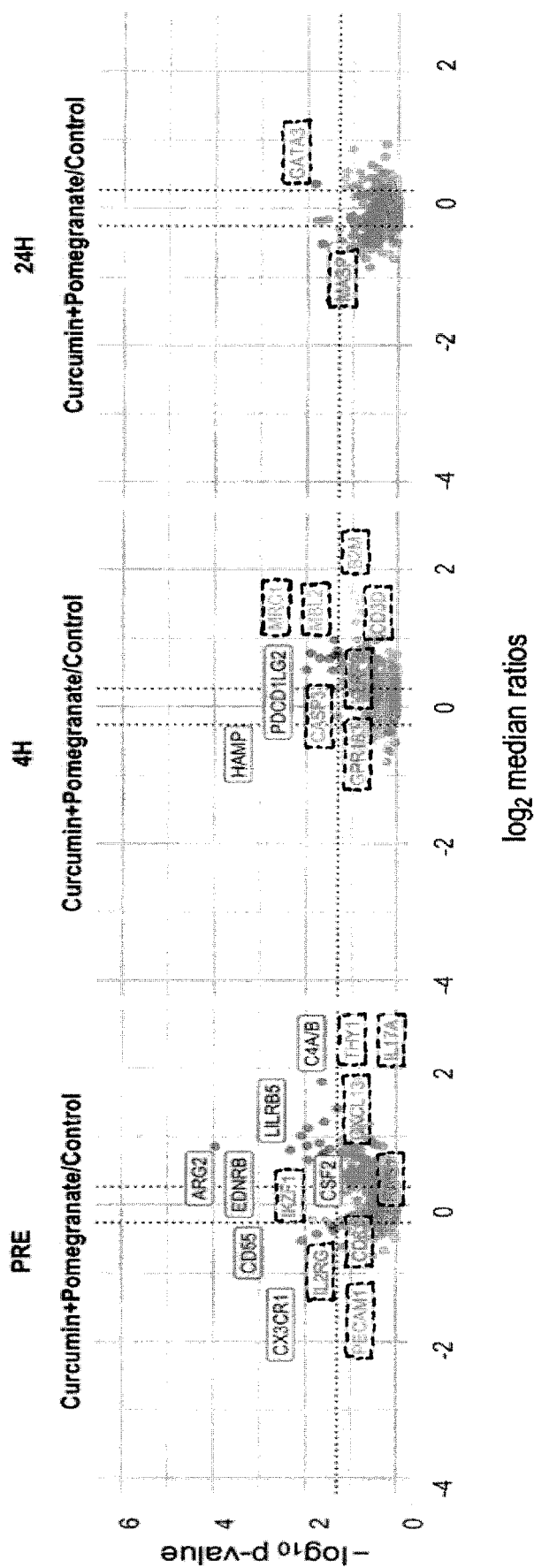
FIG. 5 shows a volcano plot showing significant upregulation or downregulation of mRNA expression in markers of immune response in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

Volcano plots were generated based on log fold change to identify NanoString® mRNA that were either up-regulated, down-regulated, or not changed with supplement compared to control (FIG. 5). At PRE, the mRNA that were significantly upregulated were ARG2, EDNRB, LILRB5, C4A/B, CSF2, RAG1, THY1, CD55, IL17A, and CXCL13 with supplement compared to control. Significantly, curcumin and pomegranate for endurance running down-regulated mRNA at PRE with supplement were CX3CR1, IKZF1, IL2RG, PECAM1, and CD81. At 4 H, the mRNA that were significantly up-regulated were HAMP, MBL2, CASP3, B2M, KLRF2, PDCD1LG2, GPR183, MRC1, and CD3D. There was no significantly down-regulated mRNA at 4 H with supplement compared to control. At 24 H, GATA3 mRNA was significantly upregulated and MASP1 was down-regulated with supplement compared to control.

DISCUSSION

The purpose of this study was to determine which systemic inflammatory proteins and RNA were altered when subjects were administered curcumin extract combined with pomegranate extract and completed a half-marathon.

Figure 6:
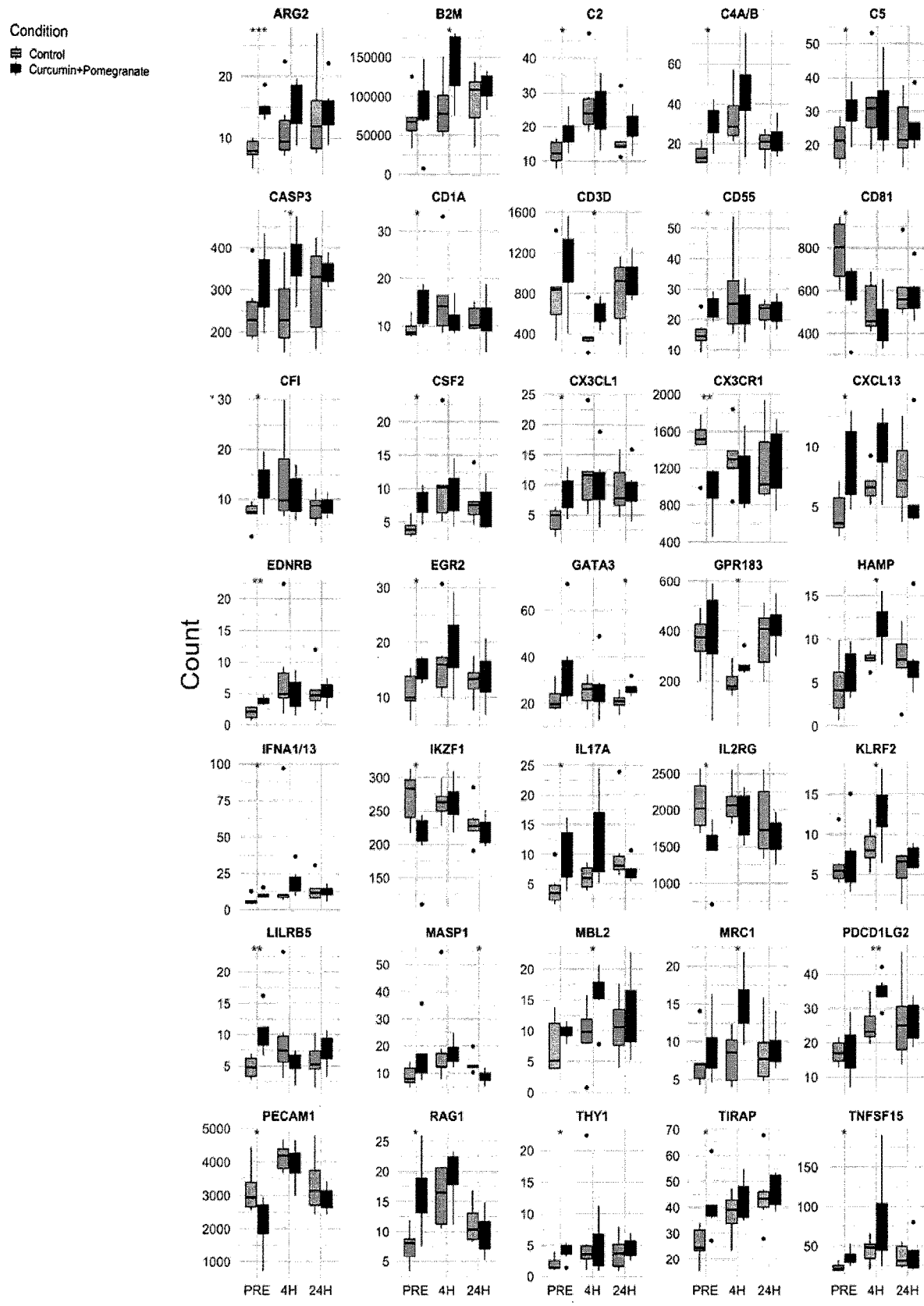
FIG. 6 shows concentrations of mRNA in markers of immune response in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

Surprisingly and unexpectedly, administration of the composition containing the combined curcumin extract and pomegranate extract showed the composition supported immune function, preparing the subject's body for an immune challenge. An increase in expression of the host-pathogen interaction RNA marker ARG2 was identified, as shown in FIGS. 5 and 6. See for instance FIG. 5 ("PRE"), showing the increased fold-change in ARG2, and FIG. 6, showing significantly increased ARG2 RNA expression with the combination of curcumin extract and pomegranate extract as compared with control before the half-marathon began (PRE; $p \leq 0.001$). The ARG2 gene encodes for the protein arginase, type II, a regulator of innate and adaptive immune responses. (From top, FIG. 6 entries are, row 1: ARG2, B2M, C2, C4A/B, C5; row 2: CASP3, CD1A, CD3D, CD55, CD81; row 3: CFI, C8F2, CX3CL1, CX3CR1, CXCL13; row 4: EDNRB, EGR2, GATA3, GPR183, HAMP; row 5: IFNA1/13, IKZF1, IL17A, IL2RG, KLRF2; row 6: LILRB5, MASP1, MBL2, MRC1, PDCD1LG2; row 7: PECAM1, RAG1, THY1, TIRAP, TNFSF18).

Also, increases in EDNRB and HAMP RNA, markers for hemostasis, may be seen in FIGS. 5 and 6 (FIG. 6 middle row, left and right plots, respectively). EDNRB RNA increased significantly for curcumin+pomegranate (the combination of curcumin extract and pomegranate extract) over control before the half-marathon began (PRE; $p \leq 0.01$), similar to ARG2, whereas HAMP RNA increased significantly for curcumin+pomegranate (the combination of curcumin extract and pomegranate extract) over control 4 hours after the subject finished the half-marathon (4 H; $p \leq 0.05$). The EDNRB gene encodes for endothelin receptor type B, and the HAMP gene for hepcidin antimicrobial peptide, both of which are markers for hemostasis, which is linked to immune function and in particular adaptive immunity.

While these changes are not associated with muscle injury, they support our claim that the combination of curcumin extract and pomegranate extract of this invention support and improve immune function, before strenuous exercise as well as the post-exercise immune system. Also, the findings support a reduced incidence of opportunistic infection that is commonly reported following strenuous endurance exercise. The changes in RNA expression following administration of the combined curcumin and pomegranate extracts of the present invention mirror changes observed with protein biomarkers.

Figure 7:
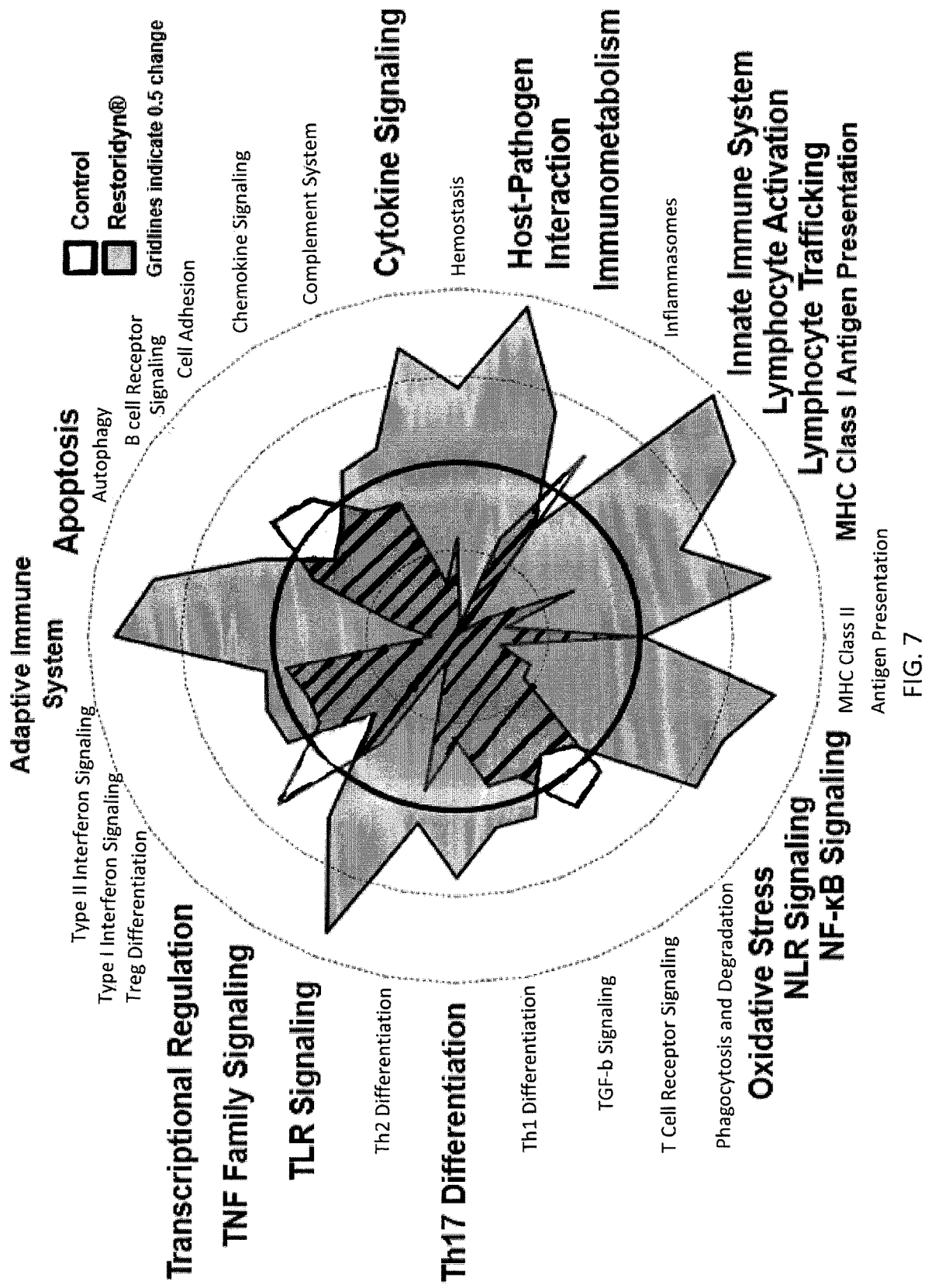
FIG. 7 illustrates immune system changes in subjects administered a composition having curcumin extract and pomegranate extract of the present invention, compared with control, after running a half-marathon. Control (white), Restoridyn® (shaded), overlap (striped).

Further investigation shows immune system changes and support for the Adaptive Immune System and the Innate Immune System, for instance as seen by changes from curcumin+pomegranate (the combination of curcumin extract and pomegranate extract) administration in RNA expression relating to the Adaptive Immune System, Apoptosis, Autophagy, B Cell Receptor Signaling, Cell Adhesion, Chemokine Signaling, Complement System, Cytokine Signaling, Hemostasis (EDNRB and HAMP), Host-Pathogen Interaction (ARG2), Immunometabolism, Inflammasomes, Innate Immune System, Lymphocyte Activation, Lymphocyte Trafficking, MHC Class I Antigen Presentation, MHC Class II Antigen Presentation, NF-κB Signaling, NLR Signaling, Oxidative Stress, Phagocytosis and Degradation, T Cell Receptor Signaling, TGF-b Signaling, Th1 Differentiation, Th17 Differentiation, Th2 Differentiation, TLR Signaling, TNF Family Signaling, Transcriptional Regulation, Treg Differentiation, Type I Interferon Signaling, Type II Interferon Signaling, all as shown in FIG. 7.

With regard to the original goal of this study, our laboratory and others have demonstrated that supplementation with optimized curcumin alone has the potential to reduce protein inflammatory cytokines and muscle soreness following a variety of laboratory-based muscle damage tests [McFarlin et al., "*Does Acute Improvement in Muscle Recovery with Curcumin Supplementation Translate to Long-term Training?*" *J. Sci. Sport Exerc.* pp. 1-5 (2019).].

We observed a group of cytokines whose pre-exercise values were greater in supplement than control; however, this difference disappeared by 4-hour post-race due to an increase in the control and no change in the supplement group (IL-10, IL-13, IL-4, ITAC, MIP-1alpha, MIP-3alpha, and TNF-alpha). Further, we found no group differences in a variety of muscle damage biomarkers prior to exercise (muscle damage myokines, CK, etc.; data not shown), hence the difference between groups is likely due to individual variability and not a supplement effect. It is notable that the control group experienced an increase in these markers (IL-10, IL-13, 11-4, ITAC, MIP-1alpha, MIP-3alpha, and TNF-alpha) at 4-hour post-race, while the supplement had no change. This later finding supports a potential effect of a blunted post-race inflammatory response with supplement. Some of the proteins had a similar exercise-induced increase at 4-hour post-race in both groups, with the only significant difference being at PRE (IL-8 and sgp130). Specific proteins that changed with supplement were associated with chemotactic signaling (ITAC, IL-8, MIP-3alpha, and MIP-1alpha), anti-inflammatory (IL-10 and IL-13), muscle recovery (BDNF), and B cell activation (sIL-2Ralpha, IL-8, and IL-4). All of these proteins have been previously reported to play a role in muscle recovery from exercise and/or injury [Gary (2019); Nicol (2015); Sciberras, J. N., et al., "The effect of turmeric (Curcumin) supplementation on cytokine and inflammatory marker responses following 2 hours of endurance cycling" J. Int. Soc. Sports Nutr. 12(1):5 (2015); Davis et al., "Curcumin effects on inflammation and performance recovery following eccentric exercise-induced muscle damage" Am. J. Physiol. Regul. Integr. Comp. Physiol. 292(6):R2168-73 (2007); Drobnic et al., "Reduction of delayed onset muscle soreness by a novel curcumin delivery system (Meriva®): a randomised, placebo-controlled trial" J. Int. Soc. Sports Nutr. 11:31 (2014); McFarlin (2016); Bernecker et al., "Evidence for an exercise induced increase of TNF-alpha and IL-6 in marathon runners" Scand. J. Med. Sci Sports 23(2):207-14 (2013); Suzuki et al., "Changes in markers of muscle damage, inflammation and HSP70 after an Ironman Triathlon race" Eur. J. Appl. Physiol. 98(6):525-34 (2006)].

Explaining the protein response with supplement may partially be difficult because all the subjects were considered healthy and most commercial protein assays are optimized to measure disease associated changes (which we did not observe in the present study). Supplement was associated with no increase in proteins at 4-hour compared to control, which may be consistent with an improved response. The control response for all proteins was consistent with what our lab and others have reported following distance running. Similar to the protein cytokine response, we found a group of RNA with greater levels prior to the race with supplement compared to control, but this difference was not present at 4-hour post-race due to an increase in the control group response and no change with supplement (CCL22, GUSB, IL-6, LINC00305, NKILA, PTGES, THRIL, TRAF6, ARG2, CD1A, CD55, CFI, CSF2, CXC3CL1, CX3CR1, EDNRB, GATA3, LILRB5, THY1, and TIRAP). The preexercise difference may or may not be due to individual variability rather than a supplement effect due to no differences in muscle injury markers measured (muscle damage myokines, CK, etc.; data not shown). Some RNA were increased at 4-hour post-race regardless of condition (IL-10, IL-6R, MYD88, PTGS2, TLR2, TNFRSF1A, TNFRSF1B, TNFSF14, B2M, C2, C4A/B, CASP3, EGR2, HAMP, IFNA1/B, IKZF1, IL-17A, IL2RG, KLRF2, MASP1, MBL2, MRC1, PDCD1LG2, PECAM1, RAG1, TNFSF15). The RNA that changed with supplement were associated with TNFα (TNFSF14, TRAF6, and THRIL), nuclear factor kappa beta (NF-κβ) signaling pathway (NKILA and LINC00305), inflammation-associated RNA (IL-10, IL-6, PTGES, TLR2, IL7R, CX3CL1, CCL22, IL-8, CSF2, RAG1, IL-17A, IL2RG, CX3CR1, CASP3, B2M, GATA3, LILRB5, C4A/B, PECAM1, MASP1, MBL2, CD55, THY1, IKZF1, PDCD1LG2, and KLRF2), and anti-inflammatory RNA (TNFRSF1A, TNFRSF1B, and IL-6R).

Similar to the protein response, supplementation resulted in no change in certain RNA at 4-hour, compared to an increased response with control, which may be consistent with an improved response. Interestingly, as discussed above, we also detected changes in host-pathogen interaction (ARG2) and hemostasis (EDNRB and HAMP). While these responses are not associated with muscle injury their change support an improved post-exercise immune system and reduced incidence of opportunistic infection that is commonly reported following strenuous endurance exercise [McFarlin et al., "Baker's yeast beta glucan supplementation increases salivary IgA and decreases cold/flu symptomatic days after intense exercise" J. Diet. Suppl. 10(3):171-183 (2013); Bergendiova et al., "Pleuran (beta-glucan from Pleurotus ostreatus) supplementation, cellular immune response and respiratory tract infections in athletes" Eur. J. Appl. Physiol. 111(9):2033-2040 (2011); Gleeson et al., "Respiratory infection risk in athletes: association with antigen-stimulated IL-10 production and salivary IgA secretion" Scand. J. Med. Sci. Sports 22(3):410-417 (2012); Gleeson et al., "Influence of training load on upper respiratory tract infection incidence and antigen-stimulated cytokine production" Scand. J. Med. Sci. Sports 23(4):451-457 (2013)]. In summary, the observed supplement-associated changes in RNA mirror the changes observed with protein biomarkers, and show that the present compositions support immune health.

It is well documented that reduced post-exercise inflammation is associated with a faster return to normal function in activities of daily living or training [Bell et al., "Recovery facilitation with Montmorency cherries following high-intensity, metabolically challenging exercise" Appl. Physiol. Nutr. Metab. 40(4):414-23 (2015); McLeay et al., "Effect of New Zealand blueberry consumption on recovery from eccentric exercise-induced muscle damage" J. Int. Soc. Sports Nutr. 9(1):19 (2012); Michailidis et al., "Thiol-based antioxidant supplementation alters human skeletal muscle signaling and attenuates its inflammatory response and recovery after intense eccentric exercise" Am. J. Clin. Nutr. 98(1): 233-45 (2013)].

The findings of the present study are consistent with previously reported reductions in post-exercise inflammation. When combining all the biomarker responses, a similar pattern was observed where supplement was associated with no change at 4-hour, which is consistent with a blunted post-exercise response compared to control. By extension it is reasonable to speculate that combined supplementation with optimized curcumin and a pomegranate extract may be useful as part of a comprehensive plan designed to mitigate post-exercise inflammation/injury and improve subsequent recovery between sessions.

In FIG. 1, the volcano plots display the group comparison log 2 median ratios (Curcumin+Pomegranate/Control) of protein biomarker data and the log 10-p-value of the Welch t-test (horizontal dashed line: p-value=0.05; vertical dashed lines: fold-change=1.2) at prerace (PRE), 4-hour post-race (4 H), and 24-hour post-race (24 H). Significantly up-regulated protein biomarkers with supplement compared to control are discussed in the Results section above, as are significantly down-regulated protein biomarkers with supplement compared to control. Biomarker label color saturation indicates test-power (saturated=test-power >0.8). Boxes (shown with dotted lines) indicating test-power ≤0.8 (top to bottom, PRE: IL-13, MIP-1alpha, BDNF, MIP-3alpha, sgp130; 4 H: IL-10, BDNF; 24 H:sIL-2Ralpha, IL-8, IL-4). Multiplex protein assays were conducted using commercially available bead-based kits (Milliplex®; MilliporeSigma) and multiplex analyzer (FlexMAP 3D™; Luminex Corp.).

Figure 2:
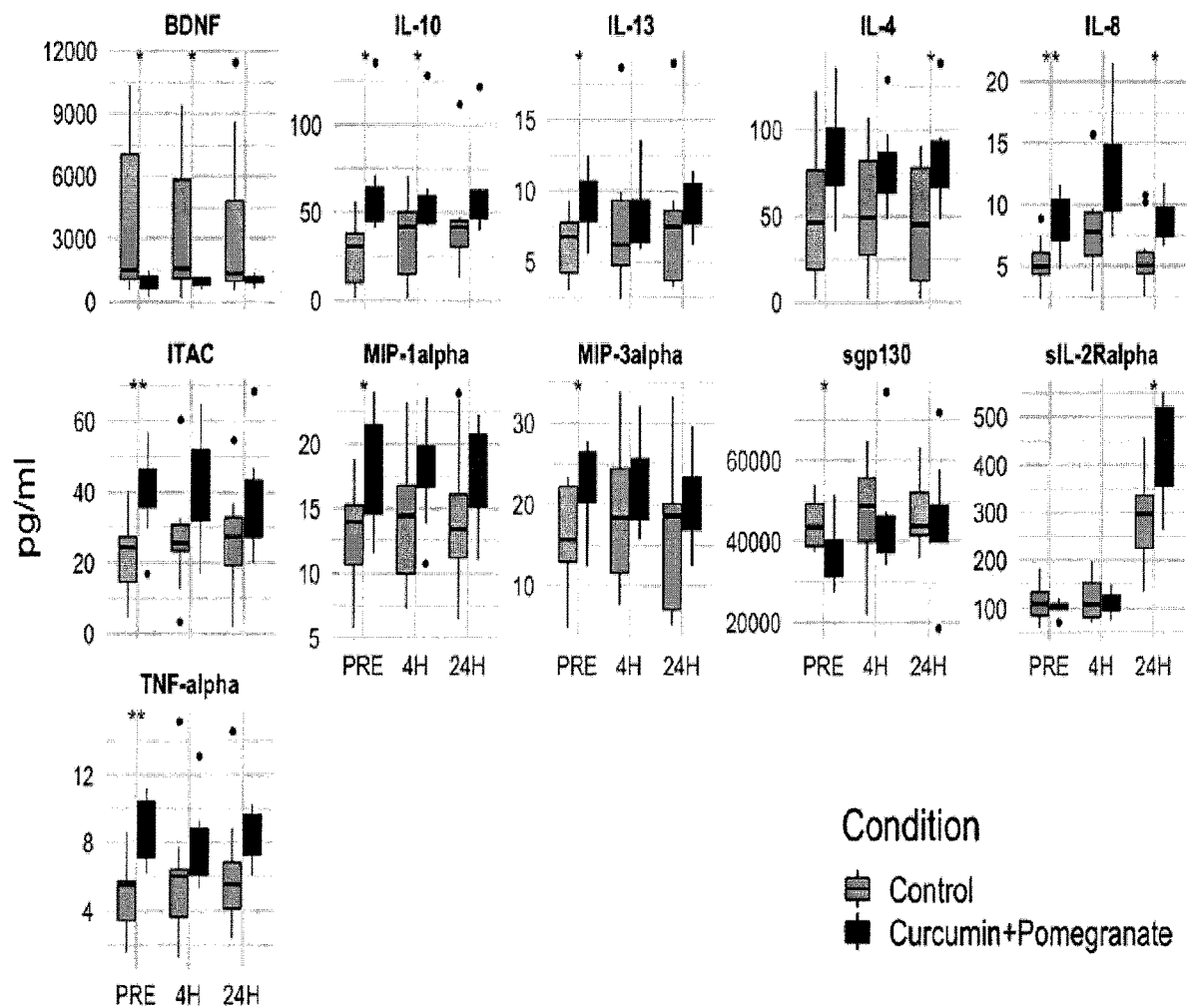
FIG. 2 shows concentrations of protein biomarkers for inflammation that significantly increased or decreased in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

FIG. 2 demonstrates the concentration of significantly changed protein biomarkers for supplement (black) and control (light grey) across all time points (PRE, 4 H, and 24 H). All protein concentrations are expressed as pg/mL. Observed supplement group responses were either flat (i.e. no response to exercise) or increased to a similar degree as the control group. Multiplex protein assays were conducted using commercially available bead-based kits (Milliplex®; MilliporeSigma) and multiplex analyzer (FlexMAP 3D™; Luminex Corp.). Note: Welch t-test p-value significance *($p \leq 0.05$); ($p \leq 0.01$); *($p \leq 0.001$); ****($p \leq 0.0001$).

The volcano plots of FIG. 3 display the group comparison log 2 median ratios (Curcumin+Pomegranate/Control) of RNA data and the log 10-p-value of the Welch t-test (horizontal dashed line: p-value=0.05; vertical dashed lines: fold-change=1.2) at pre-race (PRE), 4-h post-race (4 H), and 24-hour post-race (24 H). Significantly up-regulated RNA with supplement compared to control are discussed in the Results section above, as are significantly down-regulated RNA with supplement compared to control. Biomarker label color saturation indicates test-power (saturated=test-power >0.8). Boxes (shown with dotted lines) indicating test-power ≤0.8 (top to bottom, PRE: TNFSF14, IL6, TRAF6, NKILA; 4 H:MYD88, THRIL, TNFRSF1B, IL7R, TLR2, IL6R, CX3CL1, PTGS2; 24 H: TRAF6, LINC00305, IL6, TLR2, IL8). Multiplex RNA assays were conducted using commercially available bead-based kits (Quantigene®; ThermoFisher Scientific) and multiplex analyzer (FlexMAP 3D™; Luminex Corp.).

Figure 4:
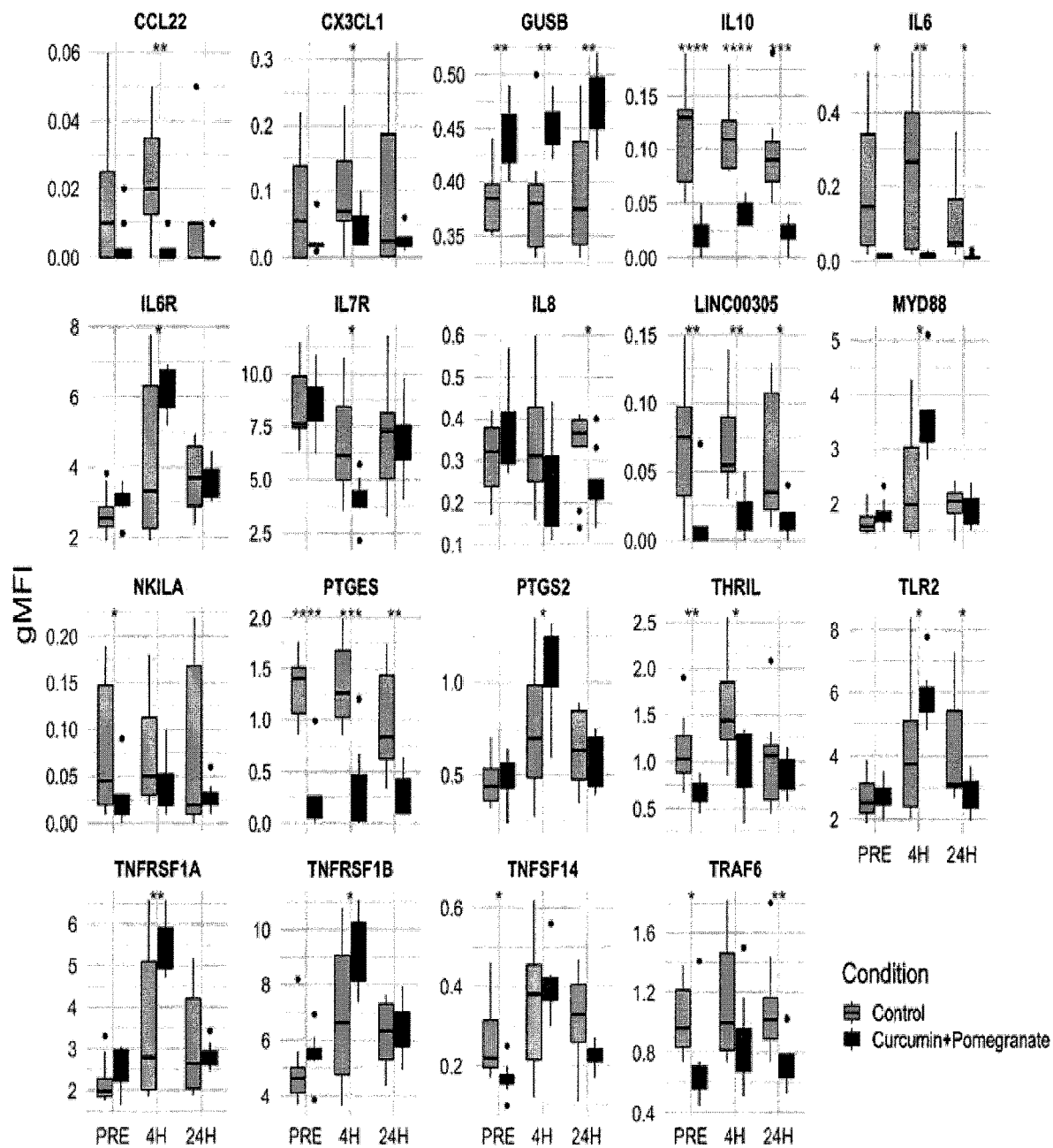
FIG. 4 shows concentrations of RNA relating to inflammation that significantly increased or decreased in subjects administered a composition having curcumin extract and pomegranate extract of the present invention, compared with control, before running a half-marathon (PRE), 4 hours after completion of the half-marathon (4 H), and 24 hours after completion of the half-marathon (24 H).

FIG. 4 shows the normalized gMFI (geometric mean of median fluorescent intensity) of significantly changed RNA for supplement (black) and control (light grey) across all time points (PRE, 4 H, and 24 H). Observed supplement group responses were either flat (i.e. no response to exercise) or increased to a similar degree as the control group. Multiplex RNA assays were conducted using commercially available bead-based kits (Quantigene®; ThermoFisher Scientific) and multiplex analyzer (FlexMAP 3D™; Luminex Corp.). Note: Welch t-test p-value significance *($p \leq 0.05$); ($p \leq 0.01$); *($p \leq 0.001$); ****($p \leq 0.0001$).

In FIG. 5, volcano plots display the group comparison log 2 median ratios (Curcumin+Pomegranate/Control) of mRNA data and the log 10-p-value of the Welch t-test (horizontal dashed line: p-value=0.05; vertical dashed lines: fold-change=1.2) at pre-race (PRE), 4-hour post-race (4 H), and 24-hour post-race (24 H). Significantly up-regulated RNA with supplement compared to control are discussed in the Results section above, as are significantly down-regulated RNA with supplement compared to control. Biomarker label color saturation indicates test-power (saturated=test-power >0.8). Boxes (shown with dotted lines) indicating test-power ≤0.8 (top to bottom, PRE: IKZF1, IL2RG, PECAM1, CD81, CXCL13, THY1, RAG1, IL17A; 4 H:MRC1, CASP3, MBL2, GPR183, KLRF2, B@M, CD3D; 24 H:GATA3, MASP1). Multiplex RNA assays were conducted using commercially available Human Immunology Panel (nCounter®; NanoString®) and imaging platform (Sprint Profiler; NanoString®).

FIG. 6 demonstrates the mRNA count for each significantly changed mRNA for supplement (black) and control (light grey) across all time points (PRE, 4 H, and 24 H). Observed supplement group responses were either flat (i.e. no response to exercise) or increased to a similar degree as the control group. Multiplex RNA assays were conducted using commercially available Human Immunology Panel (nCounter®; NanoString®) and imaging platform (Sprint Profiler; NanoString®). Note: Welch t-test p-value significance *($p \leq 0.05$); ($p \leq 0.01$); *($p \leq 0.001$); ****($p \leq 0.0001$).

Example 2

Endurance-trained men and women (26-45 years old) currently training for a half-marathon race gave Institutional Review Board (IRB) consent. Participants were assigned to Control (N=6) or Supplement (N=6). Combined curcumin and natural proprietary pomegranate extract (Restoridyn®) dietary supplements were taken in an amount of 500 mg Restoridyn® per day for 26 days. Booster doses of 1000 mg Restoridyn® per day were taken following training runs greater than 6 miles in length and 3 days prior to the half-marathon race (days 27, 28, 29). On day 29, subjects ran the half-marathon. On day 30, a booster dose was taken. Control was taken for 30 days. Restoridyn® provided to subjects was as described in Example 1.

Venous blood samples taken pre-race, 4-hours after the race, and 24-hours after the race were collected in PAXgene Blood RNA tubes (PreAnalytiX). Samples were incubated at room temperature then frozen until total RNA isolation and analysis was performed. Total RNA was isolated using an automated system (QIAcube) and RNA quantity and Quality was assessed with a fluorescent RNA assay and fluorometer (Qubit).

To measure RNA, a 594-plex Human Immunology Panel was analyzed on a NanoString nCounter Platform. Results were normalized to housekeeper genes. Differential expression analysis was conducted using Nanostring nSolver software. Significance was set at p<0.05.

See Supplementary Table 3 for further information on targets of Tables 4-7 to immune response and other embodiments of this application. Inflammation-associated mRNA expression was reduced with daily Restoridyn® administration prior to and after a half-marathon race. mRNA changes with Restoridyn® supplementation may positively affect recovery after endurance exercise and the ability to return to training more quickly.

TABLE 4

PRE-Half-Marathon

| TABLE - PRE Significant mRNA targets (p < 0.05) | Official Name | Upregulated/ Downregulated |
|---|---|---|
| CD3EAP | CD3e molecule, epsilon associated protein | Down |
| C4A/B | complement component 4A/complement component 4B | Up |
| CX3CR1 | chemokine (C-X3-C motif) receptor 1 | Down |
| TIRAP | toll-interleukin 1 receptor, domain containing adaptor protein | Up |
| TNFSF4 | tumor necrosis factor (ligand) superfamily, member 4 | Up |
| IRAK3 | interleukin-1 receptor-associated kinase 3 | Up |
| RAG1 | recombination activating gene 1 | Up |

TABLE 4-continued

PRE-Half-Marathon

| TABLE - PRE Significant mRNA targets (p < 0.05) | Official Name | Upregulated/Downregulated |
|---|---|---|
| IL2RG | interleukin 2 receptor, gamma | Down |
| TNFSF15 | tumor necrosis factor (ligand) superfamily, member 15 | Up |
| CD55 | CD55 molecule, decay accelerating factor for complement | Up |
| ARG2 | arginase, type II | Up |
| C5 | complement component 5 | Up |
| TNFSF8 | tumor necrosis factor (ligand) superfamily, member 8 | Up |
| PTK2 | PTK2 protein tyrosine Kinase 2 | Up |
| FKBP5 | FK506 binding protein 5 | Up |
| C6 | compliment component 6 | Up |
| TNFRSF17 | tumor necrosis factor receptor superfamily, member 17 | Up |
| ITGAE | integrin, alpha E | Up |
| ARG1 | arginase, liver | Up |
| C1S | complement component 1, s subcomponent | Up |
| GP1BB | glycoprotein 1b (platelet), beta polypeptide | Up |
| GATA3 | GATA binding protein 3 | Up |
| CD24 | CD24 molecule | Up |
| FOXP3 | forkhead box P3 | Up |

TABLE 5

4 Hours after Half-Marathon

| Significant mRNA targets (p < 0.05) | Official Name | Upregulated/Downregulated |
|---|---|---|
| IL28A | interleukin 28A (interferon, lambda 2) | Down |
| CSF1 | colony stimulating factor 1 (macrophage) | Down |
| BAX | BCL2-associated X protein | Down |
| IFITM1 | interferon induced transmembrane protein 1 | Up |
| GPR183 | G protein-coupled receptor 183 | Up |
| CXCL12 | chemokine (C-X-C motif) ligand 12 | Up |
| CASP3 | caspase 3, apoptosis-related cysteine peptidase | Up |
| CASP2 | caspase 2, apoptosis-related cysteine peptidase | Down |
| PDCD1 | programmed cell death 1 | Down |
| LY96 | lymphocyte antigen 96 | Up |
| CD3D | CD3d molecule, delta (CD3-TCR complex) | Up |
| B2M | Beta-2-microglobulin | Up |
| C9 | complement component 9 | Down |
| XCR1 | chemokine (C motif) receptor 1 | Down |
| IL1RL1 | interleukin 1 receptor-like 1 | Down |
| PIGR | polymeric immunoglobulin receptor | Down |
| HFE | hemochromatosis | Down |

TABLE 6

Restoridyn ® (24 H after half-marathon)

| Significant mRNA targets* (p < 0.01) | Official Name | Upregulated/Downregulated |
|---|---|---|
| ZAP70 | zeta-chain (TCR) associated protein kinase 70 kDA | Down |
| BTLA | B and T lymphocyte associated | Down |
| CD96 | CD96 molecule | Down |
| TLR5 | Toll-like receptor 5 | Up |
| SELL | Selectin L | Up |
| CEACAM1 | Carcinoembryonic antigen-related cell adhesion molecule | Up |
| ENTPD1 | Ectonucleoside triphosphate diphosphohydrolase 1 | Up |
| GNLY | Granulysin | Down |
| TLR4 | Toll-like receptor 4 | Up |
| STAT3 | Signal transducer and activator of transcription 3 (acute phase response factor) | Up |
| KLRC4 | Killer cell lectin-like receptor subfamily C, member 4 | Down |
| CD247 | CD247 molecule | Down |
| CR1 | Complement component (3b/4b) receptor 1 Knops blood group) | Up |
| STAT5A | Signal transducer and activator of transcription 5A | Up |
| BST1 | Bone marrow stromal cell antigen 1 | Up |
| CLEC5A | C-type lectin domain family 5, member A | Up |
| IFI16 | Interferon, gamma-inducible protein 16 | Up |
| FCGR3A/B | Fc fragment of IgG, low affinity IIIa, receptor (CD16a)/Fc fragment of IgG, low affinity IIIb, receptor (CD16a) | Up |
| LILRA3 | Leukocyte immunoglobulin-like receptor, subfamily A, member 3 | Up |
| LILRA2 | Leukocyte immunoglobulin-like receptor, subfamily A, member 2 | Up |
| CFP | Complement factor properdin | Up |
| SLAMF7 | SLAM family member 7 | Down |
| MYD88 | Myeloid differentiation primary response gene (88) | Up |

TABLE 6-continued

Restoridyn ® (24 H after half-marathon)

| Significant mRNA targets* (p < 0.01) | Official Name | Upregulated/Downregulated |
|---|---|---|
| TNFSF10 | Tumor necrosis factor (ligand) superfamily, member 10 | Up |
| CD58 | CD58 molecule | Up |

*Top 25 targets listed

TABLE 7

CONTROL (24 H after half-marathon)

| Significant mRNA targets* (p < 0.01) | Official Name | Upregulated/Downregulated |
|---|---|---|
| PLAUR | Plasminogen activator, urokinase receptor | Up |
| FCGR3A/B | Fc fragment of IgG, low affinity IIIa, receptor (CD16a)/Fc fragment of IgG, low affinity IIIb, receptor (CD16a) | Up |
| IGF2R | Insulin-like growth factor 2 receptor | Up |
| LILRA3 | Leukocyte immunoglobulin-like receptor, subfamily A, member 3 | Up |
| ZAP70 | Zeta-chain (TCR) associated protein kinase 70 kDa | Down |
| TRAF3 | TNF receptor-associated factor 3 | Down |
| BCL6 | B-cell CLL/lymphoma 6 | Up |
| FCGR2A/C | Fc fragment of IgG, low affinity IIa, receptor (CD32)/Fc fragment of IgG, low affinity IIc, receptor for (CD32) | Up |
| ICAM3 | Intercellular adhesion molecule 3 | Up |
| IL1RN | Interleukin 1 receptor antagonist | Up |
| CSF3R | Colony stimulating factor 3 receptor (granulocyte) | Up |
| IL6R | Interleukin 6 receptor | Up |
| HLA-B | Major histocompatibility complex, class I, B | Up |
| LILRA2 | Leukocyte immunoglobulin-like receptor, subfamily A, member 2 | Up |
| ENTPD1 | Ectonucleoside triphosphate diphosphohydrolase 1 | Up |
| MME | Membrane metallo-endopeptidase | Up |
| TNFRSF9 | Tumor necrosis factor receptor superfamily, member 9 | Up |
| STAT4 | Signal transducer and activator of transcription 4 | Down |
| TLR5 | Toll-like receptor 5 | Up |
| TLR2 | Toll-like receptor 2 | Up |

*Top 20 targets listed

Example 3

Combination Dietary Polyphenol and Methylsulfonylmethane Supplementation Alters Systemic Inflammation Time Course Response after Running a Half Marathon Race 1 Material and Methods 1.1 Participants This study was approved by the University of North Texas Institutional Review Board and was executed in accordance with the Declaration of Helsinki. Fifteen subjects gave written and oral informed consent and met inclusion criteria prior to participating the study. Inclusion criteria included: (1) male or female between the ages of 20-60 years old, (2) non-smoker, (3) healthy, with no known disease as determined by medical history questionnaire (4) physically active 6-months prior to the start of the study, and (5) currently training for a half marathon race. Participants were excluded if they consumed curcumin/turmeric, pomegranate extract, and/or methylsulfonylmethane (MSM) for three or more days per week for two months prior to the start of the study. Subject characteristics can be found in Table 8.

TABLE 8

Subject characteristics

| Gender | Control<br>Male = 5; Female = 5 | Treatment<br>Male = 3; Female = 2 |
|---|---|---|
| Age (yr) | 38.7 ± 6.0 | 40.0 ± 2.5 |
| Height (cm) | 179.1 ± 12.3 | 178.1 ± 8.3 |
| Weight (kg) | 80.7 ± 15.2 | 82.8 ± 16.3 |
| Body Fat (%) | 27.1 ± 10.8 | 26.1 ± 9.5 |

Data reported as mean ± standard deviation. No significant difference between conditions.

1.2 Experimental Design

Qualifying subjects returned to the laboratory to assess body composition using dual-energy x-ray absorptiometry (DEXA) and to receive supplementation and training log instructions. Subjects were randomized to either control (n=10) or treatment (n=5) using an open label design. Subject characteristics are presented in Table 8. The treatment group consumed a combination of Restoridyn® (1000 mg/d; 50-50 mix of optimized curcumin and pomegranate extract; Verdure Sciences; Noblesville IN) and MSM (500 mg/d; Bergstrom Nutrition; Vancouver, WA) for 26 days. During this period, subjects were instructed to consume a booster dose (additional 500 mg) in addition to the daily dose when training sessions were greater than six miles. Three days prior to and one day after the half marathon race the treatment group doubled their daily dosage (i.e. 500 mg/d to 1000 mg/). Supplement safety was assessed by measuring serum alkaline phosphatase (liver function biomarker) was measured using an enzymatic assay (Pointe Scientific; Canton, MI) on an automated chemistry analyzer (Awareness Tech; Palm City, FL). There were no differences between conditions and values were within normal range (control: 33.1±11.9; treatment: 51.2±21.1). Venous blood samples were collected from an antecubital vein prior to (PRE), 4 hours (4 h), and 24 hours (24 h) after running a half marathon race (13.1 miles; 21.1 km).

1.3 Monitoring Exercise Training

Subjects were given access to MapMyRun (UnderArmour; Baltimore, MD) to record their training sessions. Heart rate was measured using wrist-based heart rate devices (Garmin or Apple Watch) and caloric expenditure for the training sessions was estimated by the MapMyRun app. By using this approach, we were able to monitor subject training in real-time and intervene when necessary.

1.4 Biomarker Measurement

Whole blood at PRE, 4 h, and 24 h was collected into serum separator vacuettes (Griener; Kremsmünster, Austria) and PAXgene® RNA stabilizing vacutainers (PreAnalytiX, Hombrechtikon, Switzerland). The serum samples were allowed to clot at room temperature for 20-min followed by centrifugation (20-min at 400×g). The resulting serum was stored at −80° C. until analysis. PAXgene blood was frozen at −20° C. for 24-hr then transferred to long term storage at −80° C. until RNA analysis. Prior to RNA analysis, PAXgene blood was thawed and incubated at room temperature for 24-hours. RNA was analyzed using custom bead-based RNA kits (QuantiGene®; ThermoFisher Scientific; Santa Clara, CA). The RNA targets (41 mRNA, 6 lncRNA, and 3 controls) were chosen to complement the measured protein markers to assess skeletal muscle injury and oxidative stress. Protein markers were measured using a combination of commercially-available multiplex kits for high-sensitivity cytokines (Milliplex; Millipore-Sigma; St. Louis, MO; 21-cytokines), soluble cytokine receptors (Milliplex; Millipore-Sigma; 14-soluble receptors), and myokines (Milliplex; Millipore-Sigma; 15-myokines). Samples were processed according to manufacture specifications and raw data files were acquired using a bead-based multiplex analyzer (FlexMap3D; Luminex Corp; Austin, TX). Prior to analysis, instrument calibration and verification were conducted according to manufacturer specifications.

1.5 Statistical Analysis

RNA data was normalized by dividing the median fluorescent intensity for a given RNA target by the geometric mean of the 3 control RNA median fluorescent intensity. Protein biomarker concentrations were calculated using commercially available software (Milliplex Analyst v5; MilliporeSigma) that automatically calculated unknown values compared to a standard curve. $R^2$ for all standard curves were >0.98. Data were cleaned and analyzed using R-studio to create volcano plots based on log change of treatment normalized to control. A two-sample Wilcoxon Test was used to analyzed for significance based on a standardized fold change (1.2; $P<0.05$). Data were standardized into 6 volcano plots to identified biomarkers that were significantly up or down-regulated relative to control.

2 Results

2.1 Exercise Training

The goal of the present study was to identify a treatment response profile by combining the various outcome measures into a single response type. Based on the training data present above (section 2.3), the treatment response profile observed in the present study allowed for treatment subjects to train at a higher mileage and exertion level compared to controls. Specifically, as a whole the treatment group was able to complete a total of 11% more mileage (341.2±3.5 vs. 307.5±3.8 miles) and expend 20% more calories (51, 802±546 vs. 43,185±595 kcal) in a similar number of training sessions between (60 vs. 59 training sessions) as control during the 26 days leading up to the event. The nature of the training observed in the treatment group would translate to a better race performance according to the literature.

2.2 Protein Biomarkers

Figure 8:
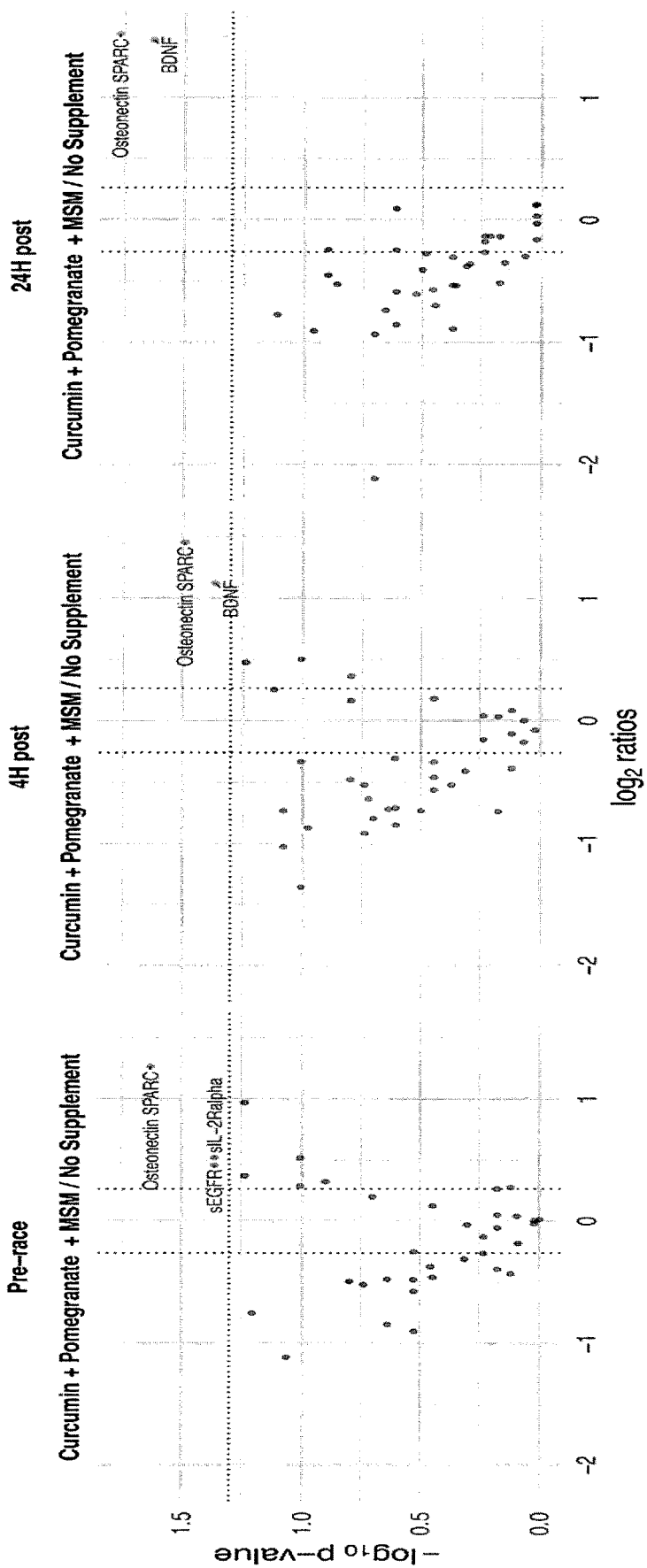
FIG. 8 is a volcano plot showing protein biomarkers significantly upregulated before running a half-marathon (PRE), 4 hours after completion of the half-marathon (4 H), and 24 hours after completion of the half-marathon (24 H).
Figure 9:
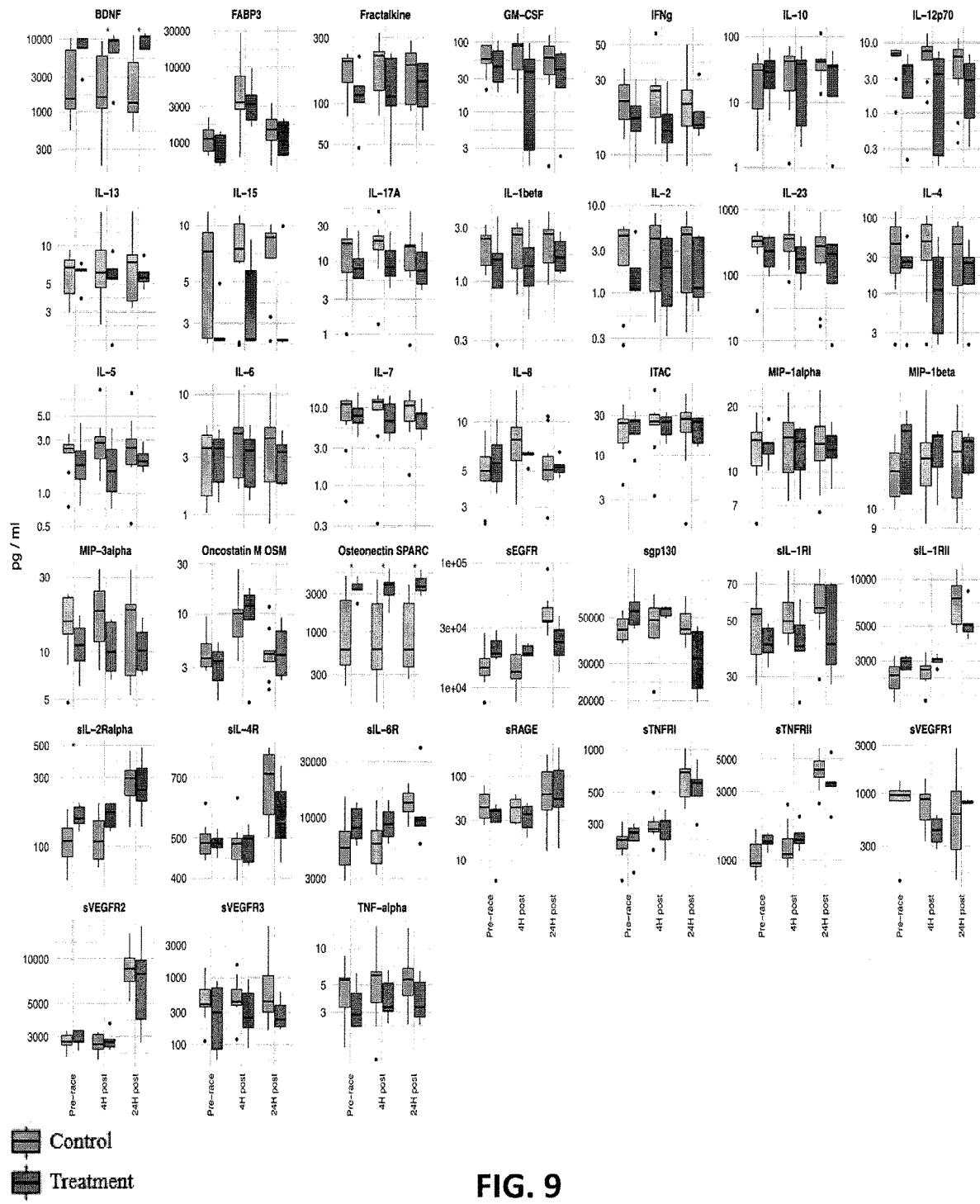
FIG. 9 shows concentrations of protein biomarkers (pg/ml) significantly upregulated before running a half-marathon (PRE), 4 hours after completion of the half-marathon (4 H), and 24 hours after completion of the half-marathon (24 H).

When analyzing for protein biomarkers that had at least 1.2 fold change we found groups of protein biomarkers that were significantly upregulated at PRE (FIG. 8A "Curcumin+Pomegranate+MSM/No Supplement"; Osteonectin/SPARC, sEGFR and sIL-2Rα), 4 H (FIG. 8B "Curcumin+Pomegranate+MSM/No Supplement"; Osteonectin/SPARC, and BDNF), and 24 H (FIG. 8C "Curcumin+Pomegranate+MSM/No Supplement"; Osteonectin/SPARC, and BDNF) compared to control. Numerical changes for all proteins measured are shown in FIG. 9 (row 1 from top, "*" indicates up-regulation: BDNF*, FABP3, Fractalkine, GM-CSF, IFNg, IL-10, IL-12p70; row 2: IL-13, IL-15, IL-17A, IL-1beta, IL-2, IL-23, IL-4; row 3: IL-5, IL-6, IL-7, IL-8, ITAC, MIP-1alpha, MIP-1beta; row 4: MIP-3alpha, Oncostatin M OSM, Osteonectin SPARC*, sEGFR*, sgp130, sIL-1RI, sIL-1RII; row 5: sIL-2Ralpha*, sIL-4R, sIL-6R, sRAGE, sTNFRI, sTNFRII, sVEGFR1; row 6: sVEGFR2, sVEGFR3, TNF-alpha. Control (light grey) and Treatment (dark grey) are shown for each, left to right, PRE-RACE, 4 H post-race, and 24 H post race.)

2.3 RNA Biomarkers

Figure 10:
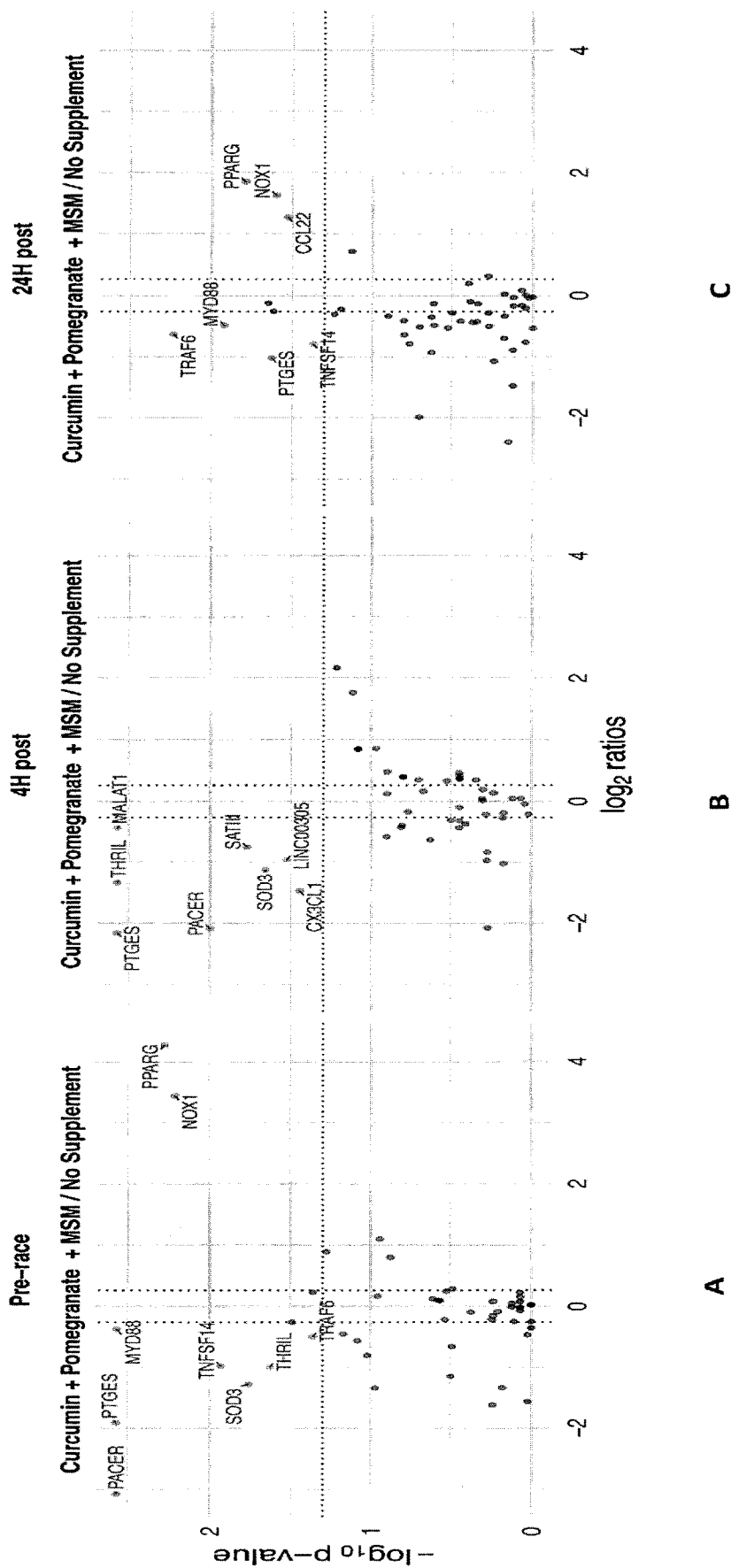
FIG. 10 is a volcano plot showing RNA biomarkers significantly upregulated before running a half-marathon (PRE), 4 hours after completion of the half-marathon (4 H), and 24 hours after completion of the half-marathon (24 H).
Figure 11:
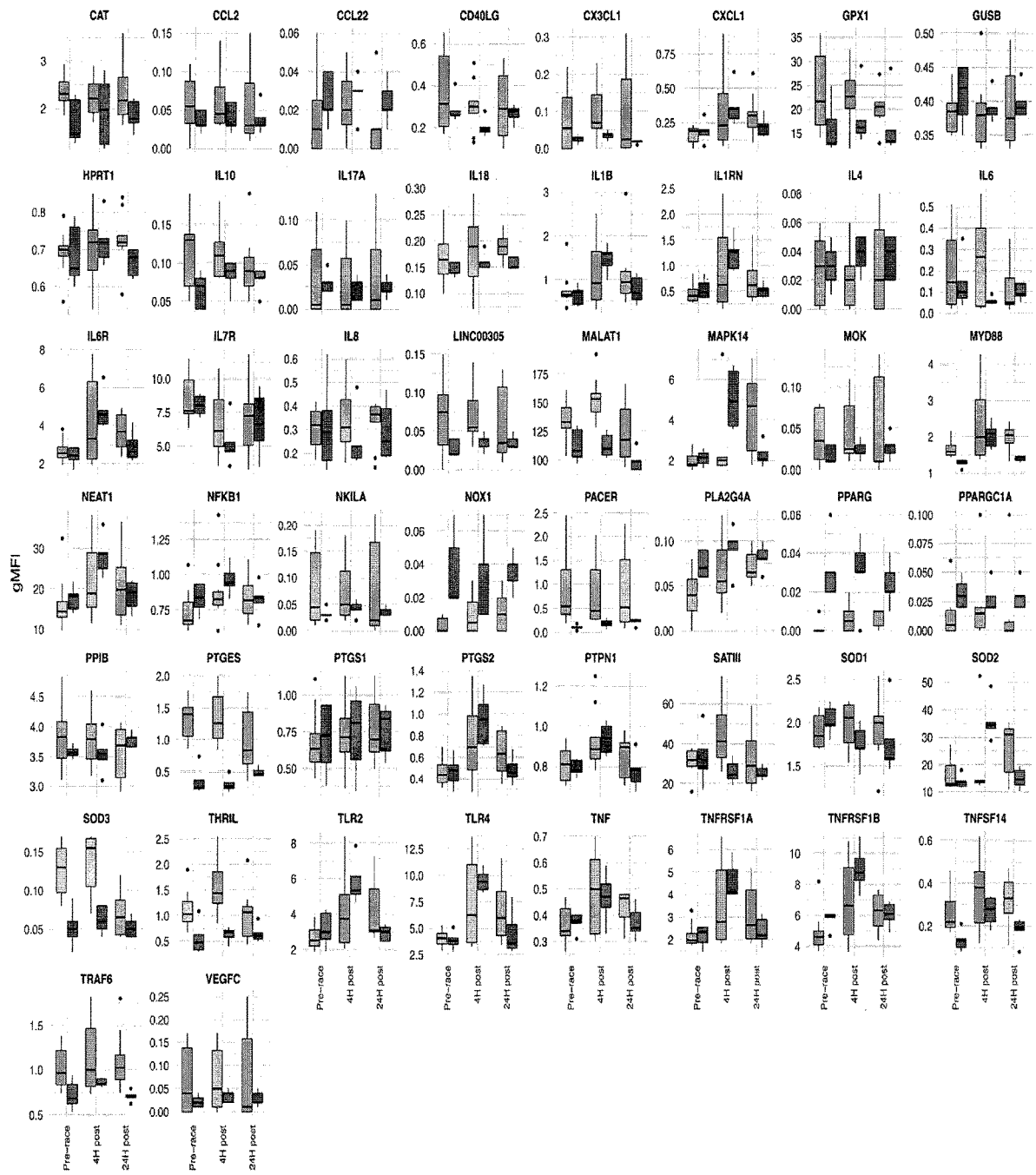
FIG. 11 shows numerical changes for all RNA measured (gMFI; geometric mean of median fluorescent intensity) before running a half-marathon (PRE), 4 hours after completion of the half-marathon (4 H), and 24 hours after completion of the half-marathon (24 H).

When analyzing for RNA biomarkers that had at least 1.2 fold change we found groups of biomarkers that were significantly upregulated at PRE (FIG. 10A; PPARg & NOX1) and 24 H (FIG. 10C; PPARg, NOX1, and CCL22) compared to control. No RNA were found to significantly increase relative to control at 4 H (FIG. 10B). We also identified RNA that were significantly downregulated compared to control at PRE (FIG. 10A; PACER, PTGES, MYD88, TNFS14, SOD3, THRIL, and TRAF6), 4 H (FIG. 10B; PTGES, THRIL, MALAT1, PACER, SOD3, SATIII, CX3CL1, LNC00305), and 24 H (FIG. 10C; TRAF6, MYD88, PTGES, and TNFS14). Numerical changes for all RNA measured are shown in FIG. 11 ("*" indicates upregulation, "**" indicates down regulation (FC≥1.2). Row 1 from top: CAT, CCL2, CCL22*, CD40LG, CX3CL1, CXCL1, GPX1, GUSB; row 2: HPRT1, IL10, IL17A, IL18, IL1B, IL1RN, IL4, IL6; row 3: IL6R, IL7R, IL8, LINC00305, MALAT1, MAPK14, MOK, MYD88; row 4: NEAT1, NFKB1, NKILA, NOX1*, PACER**, PLA2G4A, PPARG*, PPARGC1A; row 5: PPIB, PTGES, PTGS1, PTGS2, PTPN1, SATIII, SOD1, SOD2; row 6: SOD3, THRIL, TLR2, TLR4, TNF, TNFRSF1A, TNFRSF1B, TNFSF14; row 7: TRAF6, VEGFC. Control (light grey) and Treatment (dark grey) are shown for each, left to right, PRE-RACE, 4 H post-race, and 24 H post race.).

3 Discussion

The present study aimed to identify the effect of dietary supplementation with a combination of curcumin, pomegranate, and MSM on inflammation-associated protein and RNA biomarkers prior to and after a half marathon race performance. This study is part of our larger research agenda, which aims to understand and improve biological response to muscle injury and repair. Through this work, our goal is to develop more effective strategies to improve the effectiveness of exercise training, while minimizing common side effects (i.e. soreness, inflammation, overuse injuries, etc.). As the science of biomarker detection has advanced, it has become possible for small labs to expand their measurement capacity with minimal increase in study cost. The present study took advantage of bead-based multiplexing to measure a broad array of inflammation-associated protein and RNA biomarkers. While science has advanced such that multiplexing is within reach for most laboratories, drawing conclusions has become more complicated because new statistical techniques are needed to develop a treatment response profile. To address this later issue, we used statistical methodology that resulted in the creation of volcano plots at each time point comparing treatment (Restoridyn®+MSM) to control and uniquely identified biomarkers that were either up or down regulated/expressed with treatment. Distance running is commonly investigated in the scientific literature; however, attempts to minimize side effects with dietary treatments have been inconsistent. The present study demonstrates when strategically used, a combination dietary polyphenol and MSM treatment was associated with reductions in inflammation-associated RNA and an increase in muscle recovery proteins. The present study was focused on short-term recovery (within the $1^{st}$ 24-h) because this is a critical period of time that affects the ability to return to next practice and activities of daily living.

The observed treatment response profile for protein biomarkers was consistent with an increase in the muscle recovery rate at both 4-h and 24-h (increased Osteonectin/SPARC, and BDNF). Also, we observed a pre-exercise response profile consistent with an increased ability to control type 1 cytokines (increased sEGFR and sIL-2Rα). In the last decade, it was determined that during exercise, skeletal muscle is highly metabolically active and releases a variety of myokines that have systemic implications. According to the literature it is clear when exercise is sustained for long periods of time, myokine release is increased compared to shorter exercise durations. Osteonectin/SPARC and BDNF both play a role in promoting recovery from injury. Thus, based on previous research the treatment response profile resulted in conditions that favored a more rapid return to exercise and normal activities following the half-marathon race.

With respect to RNA biomarkers, the observed treatment response profile included a reduction in inflammation-associated RNA at both 4-h and 24-h with treatment (PACER, PTGES, MYD88, TNFS14, THRIL, TRAF6, CX2CL1, MALAT1, and LNC00305). The treatment response profile also included increase expression of anti-inflammatory RNA (PPARg, NOX1, and CCL22). Interestingly, the treatment response profile included reductions in inflammation-associated RNA, but not the corresponding proteins. Our lab and other have demonstrated that controlled, muscle-damaging laboratory exercise can cause transient disruptions in systemic inflammatory proteins. It is possible that the present results differ because the degree of muscle damage was much lower with the half-marathon model than traditional muscle damage models (i.e. eccentric reps, down-hill running, etc.). Given that we observed reductions in inflammation-associated RNA, it is also possible that the treatment delayed the inflammatory protein response until after 24-h post-race. Regardless, the treatment response profile that includes the observed changes in proteins and RNA reflects an improved recovery from running a half-marathon during the early recovery period.

No study is without limitations and the present study is certainly no exception. While we worked very hard to delimit as many variables as possible, when using an applied, field-based study model difficulty are to be expected. One potential limitation of the present study is the small sample size, although this was mitigated by the fact that we used a unique statistical approach that focused on identifying a treatment response profile using all the protein and RNA biomarkers in combination at each time point. This approach was determined a priori to specifically address what we planned to be a small sample size. Another potential limitation of this study is associated with the selected time points for blood collection. The time points were selected to focus on the early phase of recovery for exercise consistent with what we have previously studied. Given the difference in response between protein and RNA biomarkers during this period, it is reasonable to speculate that additional treatment response profiles may exist for later recovery (>24-h post exercise). Through this process, we identified a unique treatment response profile.

In summary, oral supplementation with combined curcumin, pomegranate, MSM resulted in an improved inflammatory and muscle recovery response during the first 24-h after running a half marathon. Better management of post exercise inflammation may translate to faster, more effective recovery. An applied goal of this work was to determine how to improve the speed of return to normal activities and exercise training. The treatment response profile was determined by combining bead-based measurements with volcano plots to uniquely identify treatment effects using all of the outcome variables in combination. It is noteworthy that these changes were observed in a group of free living adults who did not exercise in the confines of a laboratory, yet we found responses that were very consistent to what our lab and others have observed in laboratory-based models of muscle injury and recovery.

The use of the terms "a," "an," "the," and similar referents in the context of describing the present invention (especially in the context of the claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. Use of the term "about" is in an embodiment intended to describe values either above or below the stated value in a range of approximately ±10%; in other embodiments, the values may range in value above or below the stated value in a range of approximately ±5%; in other embodiments, the values may range in value above or below the stated value in a range of approximately ±2%; in other embodiments, the values may range in value above or below the stated value in a range of approximately ±1%. The preceding ranges are intended to be made clear by context, and no further limitation is implied. All method steps described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise stated. No language in the specification should be construed as indicating any non-claimed element as essential to the practice of the invention.

While in the foregoing specification the present invention has been described in relation to certain embodiments thereof, and many details have been put forth for the purposes of illustration, it will be apparent to those skilled in the art that the invention is susceptible to additional embodiments and that certain of the details described herein can be varied considerably without departing from the basic principles of the invention.

The present invention may be embodied in other specific forms without departing from the spirit or essential attributes thereof, and, accordingly, reference should be made to the appended claims, rather than to the foregoing specification, as indicating the scope of the invention.

SUPPLEMENTARY TABLE 1

Summary of Protein biomarkers

| Abbreviation | Name | Type | Relevance |
|---|---|---|---|
| Fractalkine | Fractalkine | Cytokine | Inflammation |
| GM-CSF | Granulocyte macrophage colony-stimulating factor | Cytokine | Inflammation |
| IFNg | Interferon-gamma | Cytokine | Inflammation |
| IL-10 | Interleukin-10 | Cytokine | Inflammation |
| IL-12p70 | Interleukin-12 (bioactive form) | Cytokine | Inflammation |
| IL-13 | Interleukin-13 | Cytokine | Inflammation |
| IL-17A | Interleukin-17A | Cytokine | Inflammation |
| IL-1beta | Interleukin-1 beta | Cytokine | Inflammation |
| IL-2 | Interleukin-2 | Cytokine | Inflammation |
| IL-23 | Interleukin-23 | Cytokine | Inflammation |
| IL-4 | Interleukin-4 | Cytokine | Inflammation |
| IL-5 | Interleukin-5 | Cytokine | Inflammation |
| IL-6 | Interleukin-6 | Cytokine | Inflammation |
| IL-7 | Interleukin-7 | Cytokine | Inflammation |
| IL-8 | Interleukin-8 | Cytokine | Inflammation |
| ITAC | Interferon-inducible T cell alpha chemoattractant | Cytokine | Inflammation |
| MIP-1alpha | C-C motif chemokine 3 | Cytokine | Inflammation |
| MIP-1beta | C-C motif chemokine 4 | Cytokine | Inflammation |
| MIP-3alpha | C-C motif chemokine 20 | Cytokine | Inflammation |
| TNF-alpha | Tumor necrosis factor alpha | Cytokine | Inflammation |
| IL-15 | Interleukin-15 | Myokine | Inflammation |
| Oncostatin M OSM | Oncostatin-M | Myokine | Inflammation |
| SEGFR | Soluble epidermal growth factor receptor | Soluble cytokine receptor | Inflammation |
| sgp130 | Soluble gp130 | Soluble cytokine receptor | Inflammation |
| SIL-1RI | Soluble interleukin-1 receptor, type 1 | Soluble cytokine receptor | Inflammation |
| SIL-1RII | Soluble interleukin-1 receptor, type 2 | Soluble cytokine receptor | Inflammation |
| SIL-2Ralpha | Soluble interleukin-2 receptor subunit alpha | Soluble cytokine receptor | Inflammation |
| SIL-4R | Soluble interleukin-4 receptor | Soluble cytokine receptor | Inflammation |
| SIL-6R | Soluble interleukin-6 receptor | Soluble cytokine receptor | Inflammation |
| SRAGE | Soluble receptor for advanced glycation end-products | Soluble cytokine receptor | Inflammation |
| STNFRI | Soluble tumor necrosis factor receptor 1 | Soluble cytokine receptor | Inflammation |
| STNFRII | Soluble tumor necrosis factor receptor 2 | Soluble cytokine receptor | Inflammation |
| SVEGFR1 | Soluble vascular endothelial growth factor receptor-1 | Soluble cytokine receptor | Inflammation |
| SVEGFR2 | Soluble vascular endothelial growth factor receptor-2 | Soluble cytokine receptor | Inflammation |
| BDNF | Brain-derived neurotrophic factor | Myokine | Muscle injury |
| FABP3 | Fatty acid-binding protein 3 | Myokine | Muscle injury |
| Osteonectin/SPARC | Osteonectin/SPARC | Myokine | Muscle injury |
| SVEGFR3 | Soluble vascular endothelial growth factor receptor-3 | Soluble cytokine receptor | Muscle injury |

SUPPLEMENTARY TABLE 2

Summary of bead-based RNA biomarkers

| Abbreviation | Name | Type | Pathway |
|---|---|---|---|
| LINC00305 | Long Intergenic Non-Protein Coding RNA 305 | lncRNA | Inflammation |
| MALAT1 | Metastasis associated lung adenocarcinoma transcript 1 | lncRNA | Inflammation |
| NEAT1 | Nuclear paraspeckle assembly transcript 1 | lncRNA | Inflammation |
| NKILA | NF-kappaB interacting lncRNA | lncRNA | Inflammation |
| PACER | P50-associated COX-2 extragenic RNA | lncRNA | Inflammation |
| THRIL | TNF and HNRNPL related immunoregulatory long non-coding RNA | lncRNA | Inflammation |
| CCL2 | C-C motif chemokine ligand 2 | mRNA | Inflammation |
| CCL22 | C-C motif chemokine ligand 22 | mRNA | Inflammation |
| CD40LG | CD40 ligand | mRNA | Inflammation |
| CX3CL1 | C-X3-C motif chemokine ligand 1 | mRNA | Inflammation |
| CXCL1 | C-X-C motif chemokine ligand 1 | mRNA | Inflammation |
| IL10 | Interleukin 10 | mRNA | Inflammation |
| IL17A | Interleukin 17A | mRNA | Inflammation |
| IL18 | Interleukin 18 | mRNA | Inflammation |
| IL1B | Interleukin 1 beta | mRNA | Inflammation |
| IL1RN | Interleukin 1 receptor antagonist | mRNA | Inflammation |
| IL4 | Interleukin 4 | mRNA | Inflammation |
| IL6 | Interleukin 6 | mRNA | Inflammation |
| IL6R | Interleukin 6 receptor | mRNA | Inflammation |
| IL7R | Interleukin 7 receptor | mRNA | Inflammation |
| IL8 | Interleukin 8 | mRNA | Inflammation |
| MOK | MOK protein kinase | mRNA | Inflammation |
| MYD88 | Innate immune signal transduction adaptor MYD88 | mRNA | Inflammation |
| NFKB1 | Nuclear factor kappa B subunit 1 | mRNA | Inflammation |
| PTGES | Prostaglandin E synthase | mRNA | Inflammation |
| PTGS1 | Prostaglandin-endoperoxide synthase 1 | mRNA | Inflammation |
| PTGS2 | Prostaglandin-endoperoxide synthase 2 | mRNA | Inflammation |
| PTPN1 | Protein tyrosine phosphatase, non-receptor type 1 | mRNA | Inflammation |
| SATIII | Satellite III (clone 18) | mRNA | Inflammation |
| TLR2 | Toll like receptor 2 | mRNA | Inflammation |
| TLR4 | Toll like receptor 4 | mRNA | Inflammation |
| TNF | Tumor necrosis factor | mRNA | Inflammation |
| TNFRSF1A | TNF receptor superfamily member 1A | mRNA | Inflammation |
| TNFRSF1B | TNF receptor superfamily member 1B | mRNA | Inflammation |
| TNFSF14 | TNF superfamily member 14 | mRNA | Inflammation |
| TRAF6 | TNF receptor associated factor 6 | mRNA | Inflammation |
| VEGFC | Vascular endothelial growth factor C | mRNA | Muscle injury |
| GUSB | Glucuronidase beta | mRNA | Housekeeper |
| HPRT1 | Hypoxanthine phosphoribosyltransferase 1 | mRNA | Housekeeper |
| PPIB | Peptidylprolyl isomerase B | mRNA | Housekeeper |

SUPPLEMENTARY TABLE 3

Summary of Nanostring Array RNA Biomarkers

| Abbreviation | Name | Type | Relevance |
|---|---|---|---|
| CD160 | CD160 molecule | mRNA | Adaptive Immune System |
| CD1A | CD1a molecule | mRNA | Adaptive Immune System |
| CD96 | CD96 molecule | mRNA | Adaptive Immune System |
| ICAM4 | intercellular adhesion molecule 4 (Landsteiner-Wiener blood group) | mRNA | Adaptive Immune System |
| ICAM5 | intercellular adhesion molecule 5, telencephalin | mRNA | Adaptive Immune System |
| KLRF1 | killer cell lectin-like receptor subfamily F, member 1 | mRNA | Adaptive Immune System |
| LILRA1 | leukocyte immunoglobulin-like receptor, subfamily A (with TM domain), member 1 | mRNA | Adaptive Immune System |
| LILRA2 | leukocyte immunoglobulin-like receptor, subfamily A (with TM domain), member 2 | mRNA | Adaptive Immune System |
| LILRA4 | leukocyte immunoglobulin-like receptor, subfamily A (with TM domain), member 4 | mRNA | Adaptive Immune System |
| LILRA5 | leukocyte immunoglobulin-like receptor, subfamily A (with TM domain), member 5 | mRNA | Adaptive Immune System |
| LILRB4 | leukocyte immunoglobulin-like receptor, subfamily B (with TM and ITIM domains), member 4 | mRNA | Adaptive Immune System |
| LILRB5 | leukocyte immunoglobulin-like receptor, subfamily B (with TM and ITIM domains), member 5 | mRNA | Adaptive Immune System |
| BCL2L11 | BCL2-like 11 (apoptosis facilitator) | mRNA | Apoptosis |
| CD82 | CD82 molecule | mRNA | Apoptosis |
| CRADD | CASP2 and RIPK1 domain containing adaptor with death domain | mRNA | Apoptosis |
| CUL9 | cullin 9 | mRNA | Apoptosis |
| PDCD2 | programmed cell death 2 | mRNA | Apoptosis |
| ATG10 | ATG10 autophagy related 10 homolog (S. cerevisiae) | mRNA | Autophagy |
| LILRB3 | leukocyte immunoglobulin-like receptor, subfamily B (with TM and ITIM domains), member 3 | mRNA | B cell Receptor Signaling; Adaptive Immune System |
| CD34 | CD34 molecule | mRNA | Cell Adhesion |
| ITGAE | integrin, alpha E (antigen CD103, human mucosal lymphocyte antigen 1; alpha polypeptide) | mRNA | Cell Adhesion |
| TGFBI | transforming growth factor, beta-induced, 68 kDa | mRNA | Cell Adhesion |
| CD22 | CD22 molecule | mRNA | Cell Adhesion; B cell Receptor Signaling; Adaptive Immune System |
| CCBP2 | chemokine binding protein 2 | mRNA | Chemokine Signaling |
| CCRL1 | chemokine (C-C motif) receptor-like 1 | mRNA | Chemokine Signaling |
| CCRL2 | chemokine (C-C motif) receptor-like 2 | mRNA | Chemokine Signaling |
| CISH | cytokine inducible SH2-containing protein | mRNA | Cytokine Signaling |
| CSF1R | colony stimulating factor 1 receptor | mRNA | Cytokine Signaling |
| CSF3R | colony stimulating factor 3 receptor (granulocyte) | mRNA | Cytokine Signaling |
| IL11RA | interleukin 11 receptor, alpha | mRNA | Cytokine Signaling |
| IL13RA1 | interleukin 13 receptor, alpha 1 | mRNA | Cytokine Signaling |
| IL16 | interleukin 16 | mRNA | Cytokine Signaling |
| IL17B | interleukin 17B | mRNA | Cytokine Signaling |
| IL19 | interleukin 19 | mRNA | Cytokine Signaling |

SUPPLEMENTARY TABLE 3-continued

Summary of Nanostring Array RNA Biomarkers

| Abbreviation | Name | Type | Relevance |
|---|---|---|---|
| IL1RL1 | interleukin 1 receptor-like 1 | mRNA | Cytokine Signaling |
| IL1RN | interleukin 1 receptor antagonist | mRNA | Cytokine Signaling |
| IL20 | interleukin 20 | mRNA | Cytokine Signaling |
| IL22RA2 | interleukin 22 receptor, alpha 2 | mRNA | Cytokine Signaling |
| IL26 | interleukin 26 | mRNA | Cytokine Signaling |
| IL32 | interleukin 32 | mRNA | Cytokine Signaling |
| IL9 | interleukin 9 | mRNA | Cytokine Signaling |
| S1PR1 | sphingosine-1-phosphate receptor 1 | mRNA | Cytokine Signaling |
| TNFRSF17 | tumor necrosis factor receptor superfamily, member 17 | mRNA | Cytokine Signaling |
| TNFRSF8 | tumor necrosis factor receptor superfamily, member 8 | mRNA | Cytokine Signaling |
| TNFSF12 | tumor necrosis factor (ligand) superfamily, member 12 | mRNA | Cytokine Signaling |
| TNFSF15 | tumor necrosis factor (ligand) superfamily, member 15 | mRNA | Cytokine Signaling |
| CCL11 | chemokine (C-C motif) ligand 11 | mRNA | Cytokine Signaling; Chemokine Signaling |
| CCL15 | chemokine (C-C motif) ligand 15 | mRNA | Cytokine Signaling; Chemokine Signaling |
| CCL16 | chemokine (C-C motif) ligand 16 | mRNA | Cytokine Signaling; Chemokine Signaling |
| CCL18 | chemokine (C-C motif) ligand 18 (pulmonary and activation-regulated) | mRNA | Cytokine Signaling; Chemokine Signaling |
| CCL22 | chemokine (C-C motif) ligand 22 | mRNA | Cytokine Signaling; Chemokine Signaling |
| CCL23 | chemokine (C-C motif) ligand 23 | mRNA | Cytokine Signaling; Chemokine Signaling |
| CCL24 | chemokine (C-C motif) ligand 24 | mRNA | Cytokine Signaling; Chemokine Signaling |
| CCL26 | chemokine (C-C motif) ligand 26 | mRNA | Cytokine Signaling; Chemokine Signaling |
| CCL7 | chemokine (C-C motif) ligand 7 | mRNA | Cytokine Signaling; Chemokine Signaling |
| CCL8 | chemokine (C-C motif) ligand 8 | mRNA | Cytokine Signaling; Chemokine Signaling |
| CCR1 | chemokine (C-C motif) receptor 1 | mRNA | Cytokine Signaling; Chemokine Signaling |
| CCR10 | chemokine (C-C motif) receptor 10 | mRNA | Cytokine Signaling; Chemokine Signaling |
| CCR8 | chemokine (C-C motif) receptor 8 | mRNA | Cytokine Signaling; Chemokine Signaling |
| CX3CR1 | chemokine (C-X3-C motif) receptor 1 | mRNA | Cytokine Signaling; Chemokine Signaling |
| CXCL13 | chemokine (C-X-C motif) ligand 13 | mRNA | Cytokine Signaling; Chemokine Signaling |
| CXCR3 | chemokine (C-X-C motif) receptor 3 | mRNA | Cytokine Signaling; Chemokine Signaling |
| CXCR6 | chemokine (C-X-C motif) receptor 6 | mRNA | Cytokine Signaling; Chemokine Signaling |

SUPPLEMENTARY TABLE 3-continued

Summary of Nanostring Array RNA Biomarkers

| Abbreviation | Name | Type | Relevance |
|---|---|---|---|
| XCR1 | chemokine (C motif) receptor 1 | mRNA | Cytokine Signaling; Chemokine Signaling |
| CD9 | CD9 molecule | mRNA | Hemostasis |
| EDNRB | endothelin receptor type B | mRNA | Hemostasis |
| FCGRT | Fc fragment of IgG, receptor, transporter, alpha | mRNA | Hemostasis |
| GP1BB | glycoprotein Ib (platelet), beta polypeptide | mRNA | Hemostasis |
| HAMP | hepcidin antimicrobial peptide | mRNA | Hemostasis |
| CSF2RB | colony stimulating factor 2 receptor, beta, low-affinity (granulocyte-macrophage) | mRNA | Hemostasis; Cytokine Signaling; Apoptosis |
| IL3 | interleukin 3 (colony-stimulating factor, multiple) | mRNA | Hemostasis; Cytokine Signaling; Apoptosis |
| C14orf166 | chromosome 14 open reading frame 166 | mRNA | Host-pathogen Interaction |
| CD3EAP | CD3e molecule, epsilon associated protein | mRNA | Host-pathogen Interaction |
| IRGM | immunity-related GTPase family, M | mRNA | Host-pathogen Interaction |
| KLRB1 | Killer cell lectin-like receptor subfamily B, member I | mRNA | Host-pathogen Interaction; Adaptive Immune System |
| MASP2 | Mannan-binding lectin serine peptidase 2 | mRNA | Host-pathogen Interaction; Complement System |
| IL1A | Interleukin 1, alpha | mRNA | Host-pathogen Interaction; Cytokine Signaling |
| IL1R2 | Interleukin 1 receptor, type II | mRNA | Host-pathogen Interaction; Cytokine Signaling |
| CCR5 | Chemokine (C-C motif) receptor 5 | mRNA | Host-pathogen Interaction; Cytokine Signaling; Chemokine Signaling |
| ITGA2B | Integrin, alpha 2b (platelet glycoprotein IIb of IIb/IIIa complex, antigen CD41) | mRNA | Host-pathogen Interaction; Hemostasis |
| ITGA6 | Integrin, alpha 6 | mRNA | Host-pathogen Interaction; Hemostasis; Cell Adhesion |
| SELPLG | Selectin P ligand | mRNA | Host-pathogen Interaction; Hemostasis; Cell Adhesion |
| C1QBP | Complement component 1, q subcomponent binding protein | mRNA | Host-pathogen Interaction; Hemostasis; Complement System |
| PDGFB | Platelet-derived growth factor beta polypeptide | mRNA | Host-pathogen Interaction; Hemostasis; Cytokine Signaling |
| ABCF1 | ATP-binding cassette, sub-family F (GCN20), member 1 | mRNA | Housekeeper |
| ALAS1 | Aminolevulinate, delta-,synthase 1 | mRNA | Housekeeper |
| EEF1G | Eukaryotic translation elongation factor 1 gamma | mRNA | Housekeeper |
| G6PD | Glucose-6-phosphate dehydrogenase | mRNA | Housekeeper |
| GAPDH | Glyceraldehyde-3-phosphate dehydrogenase | mRNA | Housekeeper |

SUPPLEMENTARY TABLE 3-continued

Summary of Nanostring Array RNA Biomarkers

| Abbreviation | Name | Type | Relevance |
| --- | --- | --- | --- |
| GUSB | Glucuronidase, beta | mRNA | Housekeeper |
| HPRT1 | Hypoxanthine phosphoribosyltransferase 1 | mRNA | Housekeeper |
| OAZ1 | Ornithine decarboxylase antizyme 1 | mRNA | Housekeeper |
| POLR1B | Polymerase (RNA) I polypeptide B, 128 kDa | mRNA | Housekeeper |
| POLR2A | Polymerase (RNA) II (DNA directed) polypeptide A, 220 kDa | mRNA | Housekeeper |
| PPIA | Peptidylprolyl isomerase A (cyclophilin A) | mRNA | Housekeeper |
| RPL19 | Ribosomal protein L19 | mRNA | Housekeeper |
| SDHA | Succinate dehydrogenase complex, subunit A, flavoprotein (Fp) | mRNA | Housekeeper |
| TBP | TATA box binding protein | mRNA | Housekeeper |
| TUBB | Tubulin, beta | mRNA | Housekeeper |
| KLRAP1 | Killer cell lectin-like receptor subfamily A pseudogene 1 | mRNA | Immune System |
| ABCB1 | ATP-binding cassette, sub-family B (MDR/TAP), member 1 | mRNA | Immunometabolism |
| B3GAT1 | Beta-1,3-glucuronyltransferase 1 (glucuronosyltransferase P) | mRNA | Immunometabolism |
| CMKLR1 | Chemokine-like receptor 1 | mRNA | Immunometabolism |
| FKBP5 | FK506 binding protein 5 | mRNA | Immunometabolism |
| KCNJ2 | Potassium inwardly-rectifying channel, subfamily J, member 2 | mRNA | Immunometabolism |
| LTB4R | Leukotriene B4 receptor | mRNA | Immunometabolism |
| LTB4R2 | Leukotriene B4 receptor 2 | mRNA | Immunometabolism |
| NT5E | 5'-nucleotidase, ecto (CD73) | mRNA | Immunometabolism |
| PLA2G2E | Phospholipase A2, group IIE | mRNA | Immunometabolism |
| RARRES3 | Retinoic acid receptor responder (tazarotene induced) 3 | mRNA | Immunometabolism |
| ARG2 | Arginase, type II | mRNA | Immunometabolism; Host-pathogen interaction |
| ENTPD1 | Ectonucleoside triphosphate diphosphohydrolase 1 | mRNA | Immunometabolism; Host-pathogen interaction |
| SLC2A1 | Solute carrier family 2 (facilitated glucose transporter), member 1 | mRNA | Immunometabolism; Host-pathogen interaction |
| CD53 | CD53 molecule | mRNA | Innate Immune System |
| CD97 | CD97 molecule | mRNA | Innate Immune System |
| CLEC4A | C-type lectin domain family 4, member A | mRNA | Innate Immune System |
| CLEC5A | C-type lectin domain family 5, member A | mRNA | Innate Immune System |
| CLEC6A | C-type lectin domain family 6, member A | mRNA | Innate Immune System |
| DEFB1 | Defensin, beta 1 | mRNA | Innate Immune System |
| DEFB103A | Defensin, beta 103A | mRNA | Innate Immune System |
| DEFB103B | Defensin, beta 103B | mRNA | Innate Immune System |
| DEFB4A | Defensin, beta 4A | mRNA | Innate Immune System |
| FCER1A | Fc fragment of IgE, high affinity 1, receptor for; alpha polypeptide | mRNA | Innate Immune System |
| GNLY | Granulysin | mRNA | Innate Immune System |
| ITLN1 | Intelectin 1 | mRNA | Innate Immune System |
| ITLN2 | Intelectin 2 | mRNA | Innate Immune System |
| LTF | Lactotransferrin | mRNA | Innate Immune System |
| MME | Membrane metallo-endopeptidase | mRNA | Innate Immune System |
| PIGR | polymeric immunoglobulin receptor | mRNA | Innate Immune System |
| TNFAIP6 | tumor necrosis factor, alpha-induced protein 6 | mRNA | Innate Immune System |

SUPPLEMENTARY TABLE 3-continued

Summary of Nanostring Array RNA Biomarkers

| Abbreviation | Name | Type | Relevance |
|---|---|---|---|
| LAIR1 | leukocyte-associated immunoglobulin-like receptor 1 | mRNA | Innate Immune System; Adaptive Immune System |
| LILRA3 | leukocyte immunoglobulin-like receptor, subfamily A (without TM domain), member 3 | mRNA | Innate Immune System; Adaptive Immune System |
| ICAM3 | intercellular adhesion molecule 3 | mRNA | Innate Immune System; Cell Adhesion; Adaptive Immune System |
| C6 | complement component 6 | mRNA | Innate Immune System; Complement System |
| C7 | complement component 7 | mRNA | Innate Immune System; Complement System |
| MUC1 | mucin 1, cell surface associated | mRNA | Innate Immune System; Cytokine Signaling |
| CCR6 | chemokine (C-C motif) receptor 6 | mRNA | Innate Immune System; Cytokine Signaling; Chemokine Signaling |
| CXCR1 | chemokine (C-X-C motif) receptor 1 | mRNA | Innate Immune System; Cytokine Signaling; Chemokine Signaling |
| CXCR2 | chemokine (C-X-C motif) receptor 2 | mRNA | Innate Immune System; Cytokine Signaling; Chemokine Signaling |
| CEACAM6 | carcinoembryonic antigen-related cell adhesion molecule 6 (non-specific cross reacting antigen) | mRNA | Innate Immune System; Hemostasis |
| CEACAM8 | carcinoembryonic antigen-related cell adhesion molecule 8 | mRNA | Innate Immune System; Hemostasis |
| SELL | selectin L | mRNA | Innate Immune System; Hemostasis; Cell Adhesion; Adaptive Immune System |
| CLU | clusterin | mRNA | Innate Immune System; Hemostasis; Complement System |
| PLAUR | plasminogen activator, urokinase receptor | mRNA | Innate Immune System; Hemostasis; Complement System |
| PPBP | pro-platelet basic protein (chemokine (C-X-C motif) ligand 7) | mRNA | Innate Immune System; Hemostasis; Cytokine Signaling; Chemokine Signaling |
| IFIH1 | interferon induced with helicase C domain 1 | mRNA | Innate Immune System; Host-pathogen Interaction |
| C1QA | complement component 1, q subcomponent, A chain | mRNA | Innate Immune System; Host-pathogen Interaction; Complement System |
| C1QB | complement component 1, q subcomponent, B chain | mRNA | Innate Immune System; Host-pathogen Interaction; Complement System |
| C1S | complement component 1, s subcomponent | mRNA | Innate Immune System; Host-pathogen Interaction; Complement System |
| C2 | complement component 2 | mRNA | Innate Immune System; Host-pathogen |

SUPPLEMENTARY TABLE 3-continued

Summary of Nanostring Array RNA Biomarkers

| Abbreviation | Name | Type | Relevance |
|---|---|---|---|
| | | | Interaction; Complement System |
| C4A/B | complement component 4A (Rodgers blood group)/complement component 4B (Chido blood group) | mRNA | Innate Immune System; Host-pathogen Interaction; Complement System |
| C4BPA | complement component 4 binding protein, alpha | mRNA | Innate Immune System; Host-pathogen Interaction; Complement System |
| C5 | complement component 5 | mRNA | Innate Immune System; Host-pathogen Interaction; Complement System |
| C8A | complement component 8, alpha polypeptide | mRNA | Innate Immune System; Host-pathogen Interaction; Complement System |
| C8B | complement component 8, beta polypeptide | mRNA | Innate Immune System; Host-pathogen Interaction; Complement System |
| C8G | complement component 8, gamma polypeptide | mRNA | Innate Immune System; Host-pathogen Interaction; Complement System |
| C9 | complement component 9 | mRNA | Innate Immune System; Host-pathogen Interaction; Complement System |
| CFB | complement factor B | mRNA | Innate Immune System; Host-pathogen Interaction; Complement System |
| CFH | complement factor H | mRNA | Innate Immune System; Host-pathogen Interaction; Complement System |
| CFI | complement factor I | mRNA | Innate Immune System; Host-pathogen Interaction; Complement System |
| CFP | complement factor properdin | mRNA | Innate Immune System; Host-pathogen Interaction; Complement System |
| CR1 | complement component (3b/4b) receptor 1 (Knops blood group) | mRNA | Innate Immune System; Host-pathogen Interaction; Complement System |
| MASP1 | mannan-binding lectin serine peptidase 1 (C4/C2 activating component of Ra-reactive factor) | mRNA | Innate Immune System; Host-pathogen Interaction; Complement System |
| VTN | vitronectin | mRNA | Innate Immune System; Host-pathogen Interaction; Complement System |
| CD19 | CD19 molecule | mRNA | Innate Immune System; Host-pathogen Interaction; Complement |

SUPPLEMENTARY TABLE 3-continued

Summary of Nanostring Array RNA Biomarkers

| Abbreviation | Name | Type | Relevance |
|---|---|---|---|
| CD58 | CD58 molecule | mRNA | System; B cell Receptor Signaling; Adaptive Immune System Innate Immune System; Host-pathogen Interaction; Hemostasis; Cell Adhesion |
| CFD | complement factor D (adipsin) | mRNA | Innate Immune System; Host-pathogen Interaction; Hemostasis; Complement System |
| SERPING1 | serpin peptidase inhibitor, clade G (C1 inhibitor), member 1 | mRNA | Innate Immune System; Host-pathogen Interaction; Hemostasis; Complement System |
| NOS2 | nitric oxide synthase 2, inducible | mRNA | Innate Immune System; Host-pathogen Interaction; Hemostasis; Cytokine Signaling |
| ITGAX | integrin, alpha X (complement component 3 receptor 4 subunit) | mRNA | Innate Immune System; Host-pathogen Interaction; Hemostasis; Cytokine Signaling; Complement System; Cell Adhesion |
| GPI | glucose-6-phosphate isomerase | mRNA | Innate Immune System; Immuno-metabolism |
| PLA2G2A | phospholipase A2, group IIA (platelets, synovial fluid) | mRNA | Innate Immune System; Immuno-metabolism |
| AICDA | activation-induced cytidine deaminase | mRNA | Lymphocyte Activation |
| AIRE | autoimmune regulator | mRNA | Lymphocyte Activation |
| CD24 | CD24 molecule | mRNA | Lymphocyte Activation |
| CD5 | CD5 molecule | mRNA | Lymphocyte Activation |
| CD7 | CD7 molecule | mRNA | Lymphocyte Activation |
| CD83 | CD83 molecule | mRNA | Lymphocyte Activation |
| DPP4 | dipeptidyl-peptidase 4 | mRNA | Lymphocyte Activation |
| GPR183 | G protein-coupled receptor 183 | mRNA | Lymphocyte Activation |
| HFE | hemochromatosis | mRNA | Lymphocyte Activation |
| KLRC3 | killer cell lectin-like receptor subfamily C, member 3 | mRNA | Lymphocyte Activation |
| KLRC4 | killer cell lectin-like receptor subfamily C, member 4 | mRNA | Lymphocyte Activation |
| KLRF2 | killer cell lectin-like receptor subfamily F, member 2 | mRNA | Lymphocyte Activation |
| KLRG2 | killer cell lectin-like receptor subfamily G, member 2 | mRNA | Lymphocyte Activation |
| LILRB2 | leukocyte immunoglobulin-like receptor, subfamily B (with TM and ITIM domains), member 2 | mRNA | Lymphocyte Activation |
| MS4A1 | membrane-spanning 4-domains, subfamily A, member 1 | mRNA | Lymphocyte Activation |
| PRDM1 | PR domain containing 1, with ZNF domain | mRNA | Lymphocyte Activation |
| BTLA | B and T lymphocyte associated | mRNA | Lymphocyte Activation; Adaptive |

SUPPLEMENTARY TABLE 3-continued

Summary of Nanostring Array RNA Biomarkers

| Abbreviation | Name | Type | Relevance |
|---|---|---|---|
| KIR_Inhibiting_Sub-group_1 | killer cell immunoglobulin-like receptor | mRNA | Immune System Lymphocyte Activation; Adaptive Immune System |
| KIR_Inhibiting_Sub-group_2 | killer cell immunoglobulin-like receptor | mRNA | Lymphocyte Activation; Adaptive Immune System |
| KIR3DL1 | killer cell immunoglobulin-like receptor, three domains, long cytoplasmic tail, 1 | mRNA | Lymphocyte Activation; Adaptive Immune System |
| KIR3DL2 | killer cell immunoglobulin-like receptor, three domains, long cytoplasmic tail, 2 | mRNA | Lymphocyte Activation; Adaptive Immune System |
| KIR3DL3 | killer cell immunoglobulin-like receptor, three domains, long cytoplasmic tail, 3 | mRNA | Lymphocyte Activation; Adaptive Immune System |
| KLRC1 | killer cell lectin-like receptor subfamily C, member 1 | mRNA | Lymphocyte Activation; Adaptive Immune System |
| KLRG1 | killer cell lectin-like receptor subfamily G, member 1 | mRNA | Lymphocyte Activation; Adaptive Immune System |
| LILRB1 | leukocyte immunoglobulin-like receptor, subfamily B (with TM and ITIM domains), member 1 | mRNA | Lymphocyte Activation; Adaptive Immune System |
| NCR1 | natural cytotoxicity triggering receptor 1 | mRNA | Lymphocyte Activation; Adaptive Immune System |
| SLAMF6 | SLAM family member 6 | mRNA | Lymphocyte Activation; Adaptive Immune System |
| SLAMF7 | SLAM family member 7 | mRNA | Lymphocyte Activation; Adaptive Immune System |
| GZMA | granzyme A (granzyme 1, cytotoxic T-lymphocyte-associated serine esterase 3) | mRNA | Lymphocyte Activation; Apoptosis |
| GZMB | granzyme B (granzyme 2, cytotoxic T-lymphocyte-associated serine esterase 1) | mRNA | Lymphocyte Activation; Apoptosis |
| GZMK | granzyme K (granzyme 3; tryptase II) | mRNA | Lymphocyte Activation; Apoptosis |
| PRF1 | perforin 1 (pore forming protein) | mRNA | Lymphocyte Activation; Apoptosis |
| CD79A | CD79a molecule, immunoglobulin-associated alpha | mRNA | Lymphocyte Activation; B cell Receptor Signaling; Adaptive Immune System |
| CD79B | CD79b molecule, immunoglobulin-associated beta | mRNA | Lymphocyte Activation; B cell Receptor Signaling; Adaptive Immune System |
| CD276 | CD276 molecule | mRNA | Lymphocyte Activation; Cell Adhesion |
| CD6 | CD6 molecule | mRNA | Lymphocyte Activation; Cell Adhesion |
| TIGIT | T cell immunoreceptor with Ig and ITIM domains | mRNA | Lymphocyte Activation; Cell Adhesion |

SUPPLEMENTARY TABLE 3-continued

Summary of Nanostring Array RNA Biomarkers

| Abbreviation | Name | Type | Relevance |
| --- | --- | --- | --- |
| CD274 | CD274 molecule | mRNA | Lymphocyte Activation; Cell Adhesion; Adaptive Immune System |
| ICOSLG | inducible T-cell co-stimulator ligand | mRNA | Lymphocyte Activation; Cell Adhesion; Adaptive Immune System |
| PDCD1LG2 | programmed cell death 1 ligand 2 | mRNA | Lymphocyte Activation; Cell Adhesion; Adaptive Immune System |
| BCL6 | B-cell CLL/lymphoma 6 | mRNA | Lymphocyte Activation; Cytokine Signaling |
| CD27 | CD27 molecule | mRNA | Lymphocyte Activation; Cytokine Signaling |
| CD70 | CD70 molecule | mRNA | Lymphocyte Activation; Cytokine Signaling |
| EBI3 | Epstein-Barr virus induced 3 | mRNA | Lymphocyte Activation; Cytokine Signaling |
| HAVCR2 | hepatitis A virus cellular receptor 2 | mRNA | Lymphocyte Activation; Cytokine Signaling |
| IL1RL2 | interleukin 1 receptor-like 2 | mRNA | Lymphocyte Activation; Cytokine Signaling |
| IL27 | interleukin 27 | mRNA | Lymphocyte Activation; Cytokine Signaling |
| IL28A | interleukin 28A (interferon, lambda 2) | mRNA | Lymphocyte Activation; Cytokine Signaling |
| IL28A/B | interleukin 28A (interferon, lambda 2)/interleukin 28B (interferon, lambda 3) | mRNA | Lymphocyte Activation; Cytokine Signaling |
| IL29 | interleukin 29 (interferon, lambda 1) | mRNA | Lymphocyte Activation; Cytokine Signaling |
| IL7 | interleukin 7 | mRNA | Lymphocyte Activation; Cytokine Signaling |
| IL7R | interleukin 7 receptor | mRNA | Lymphocyte Activation; Cytokine Signaling |
| KIT | v-kit Hardy-Zuckerman 4 feline sarcoma viral oncogene homolog | mRNA | Lymphocyte Activation; Cytokine Signaling |
| PTPN2 | protein tyrosine phosphatase, non-receptor type 2 | mRNA | Lymphocyte Activation; Cytokine Signaling |
| RAG1 | recombination activating gene 1 | mRNA | Lymphocyte Activation; Cytokine Signaling |
| RAG2 | recombination activating gene 2 | mRNA | Lymphocyte Activation; Cytokine Signaling |
| TNFRSF13B | tumor necrosis factor receptor superfamily, member 13B | mRNA | Lymphocyte Activation; Cytokine Signaling |
| TNFRSF4 | tumor necrosis factor receptor superfamily, member 4 | mRNA | Lymphocyte Activation; Cytokine Signaling |
| TNFRSF9 | tumor necrosis factor receptor superfamily, member 9 | mRNA | Lymphocyte Activation; Cytokine Signaling |
| TNFSF4 | tumor necrosis factor (ligand) superfamily, member 4 | mRNA | Lymphocyte Activation; Cytokine Signaling |
| TNFSF8 | tumor necrosis factor (ligand) superfamily, member 8 | mRNA | Lymphocyte Activation; Cytokine Signaling |

SUPPLEMENTARY TABLE 3-continued

Summary of Nanostring Array RNA Biomarkers

| Abbreviation | Name | Type | Relevance |
| --- | --- | --- | --- |
| XCL1 | chemokine (C motif) ligand 1 | mRNA | Lymphocyte Activation; Cytokine Signaling; Chemokine Signaling |
| CD244 | CD244 molecule, natural killer cell receptor 2B4 | mRNA | Lymphocyte Activation; Hemostasis |
| CD48 | CD48 molecule | mRNA | Lymphocyte Activation; Hemostasis |
| CD2 | CD2 molecule | mRNA | Lymphocyte Activation; Hemostasis; Cell Adhesion |
| KLRK1 | killer cell lectin-like receptor subfamily K, member 1 | mRNA | Lymphocyte Activation; Host-pathogen Interaction |
| PTGER4 | prostaglandin E receptor 4 (subtype EP4) | mRNA | Lymphocyte Activation; Host-pathogen Interaction |
| SLAMF1 | signaling lymphocytic activation molecule family member 1 | mRNA | Lymphocyte Activation; Host-pathogen Interaction |
| CD1D | CD1d molecule | mRNA | Lymphocyte Activation; Host-pathogen Interaction; Adaptive Immune System |
| SH2D1A | SH2 domain containing 1A | mRNA | Lymphocyte Activation; Host-pathogen Interaction; Adaptive Immune System |
| BAX | BCL2-associated X protein | mRNA | Lymphocyte Activation; Host-pathogen Interaction; Apoptosis |
| BID | BH3 interacting domain death agonist | mRNA | Lymphocyte Activation; Host-pathogen Interaction; Apoptosis |
| CCND3 | cyclin D3 | mRNA | Lymphocyte Activation; Host-pathogen Interaction; Cytokine Signaling |
| CDKN1A | cyclin-dependent kinase inhibitor 1A (p21, Cip1) | mRNA | Lymphocyte Activation; Host-pathogen Interaction; Cytokine Signaling |
| TNFRSF14 | tumor necrosis factor receptor superfamily, member 14 | mRNA | Lymphocyte Activation; Host-pathogen Interaction; Cytokine Signaling; Adaptive Immune System |
| TNFRSF10C | tumor necrosis factor receptor superfamily, member 10c, decoy without an intracellular domain | mRNA | Lymphocyte Activation; Host-pathogen Interaction; Cytokine Signaling; Apoptosis |
| IDO1 | indoleamine 2,3-dioxygenase 1 | mRNA | Lymphocyte Activation; Immuno-metabolism; Host-pathogen Interaction |
| KIR_Activating_Sub-group_1 | killer cell immunoglobulin-like receptor | mRNA | Lymphocyte Activation; Innate Immune System |
| KLRC2 | killer cell lectin-like receptor subfamily C, member 2 | mRNA | Lymphocyte Activation; Innate Immune System |
| LGALS3 | lectin, galactoside-binding, soluble, 3 | mRNA | Lymphocyte Activation; Innate Immune System |

SUPPLEMENTARY TABLE 3-continued

Summary of Nanostring Array RNA Biomarkers

| Abbreviation | Name | Type | Relevance |
|---|---|---|---|
| KIR_Activating_Sub-group_2 | killer cell immunoglobulin-like receptor | mRNA | Lymphocyte Activation; Innate Immune System; Adaptive Immune System |
| KLRD1 | killer cell lectin-like receptor subfamily D, member 1 | mRNA | Lymphocyte Activation; Innate Immune System; Adaptive Immune System |
| ICAM2 | intercellular adhesion molecule 2 | mRNA | Lymphocyte Activation; Innate Immune System; Cell Adhesion; Adaptive Immune System |
| CD55 | CD55 molecule, decay accelerating factor for complement (Cromer blood group) | mRNA | Lymphocyte Activation; Innate Immune System; Complement System |
| CD59 | CD59 molecule, complement regulatory protein | mRNA | Lymphocyte Activation; Innate Immune System; Complement System |
| CCR2 | chemokine (C-C motif) receptor 2 | mRNA | Lymphocyte Activation; Innate Immune System; Cytokine Signaling; Chemokine Signaling |
| CEACAM1 | carcinoembryonic antigen-related cell adhesion molecule 1 (biliary glycoprotein) | mRNA | Lymphocyte Activation; Innate Immune System; Hemostasis |
| MIF | macrophage migration inhibitory factor (glycosylation-inhibiting factor) | mRNA | Lymphocyte Activation; Innate Immune System; Hemostasis; Cytokine Signaling |
| CLEC4E | C-type lectin domain family 4, member E | mRNA | Lymphocyte Activation; Innate Immune System; Host-pathogen Interaction |
| CD46 | CD46 molecule, complement regulatory protein | mRNA | Lymphocyte Activation; Innate Immune System; Host-pathogen Interaction; Complement System |
| CR2 | complement component (3d/Epstein Barr virus) receptor 2 | mRNA | Lymphocyte Activation; Innate Immune System; Host-pathogen Interaction; Complement System; B cell Receptor Signaling |
| CD81 | CD81 molecule | mRNA | Lymphocyte Activation; Innate Immune System; Host-pathogen Interaction; Complement System; B cell Receptor Signaling; Adaptive Immune System |

SUPPLEMENTARY TABLE 3-continued

Summary of Nanostring Array RNA Biomarkers

| Abbreviation | Name | Type | Relevance |
|---|---|---|---|
| FCER1G | Fc fragment of IgE, high affinity I, receptor for; gamma polypeptide | mRNA | Lymphocyte Activation; Innate Immune System; Host-pathogen Interaction; Hemostasis |
| BST1 | bone marrow stromal cell antigen 1 | mRNA | Lymphocyte Activation; Innate Immune System; Immuno-metabolism |
| MBP | myelin basic protein | mRNA | Lymphocyte Trafficking |
| ARHGDIB | Rho GDP dissociation inhibitor (GDI) beta | mRNA | Lymphocyte Trafficking; Apoptosis |
| CDH5 | cadherin 5, type 2 (vascular endothelium) | mRNA | Lymphocyte Trafficking; Cell Adhesion |
| CXCR4 | chemokine (C-X-C motif) receptor 4 | mRNA | Lymphocyte Trafficking; Cytokine Signaling; Chemokine Signaling |
| CD99 | CD99 molecule | mRNA | Lymphocyte Trafficking; Hemostasis; Cell Adhesion; Adaptive Immune System |
| PECAM1 | platelet/endothelial cell adhesion molecule | mRNA | Lymphocyte Trafficking; Innate Immune System; Host-pathogen Interaction; Hemostasis; Cell Adhesion |
| PTK2 | PTK2 protein tyrosine kinase 2 | mRNA | Lymphocyte Trafficking; Innate Immune System; Host-pathogen Interaction; Hemostasis; Chemokine Signaling; Apoptosis |
| THY1 | Thy-1 cell surface antigen | mRNA | Lymphocyte Trafficking; Lymphocyte Activation |
| ITGA4 | integrin, alpha 4 (antigen CD49D, alpha 4 subunit of VLA-4 receptor) | mRNA | Lymphocyte Trafficking; Lymphocyte Activation; Host-pathogen Interaction; Hemostasis; Cell Adhesion; Adaptive Immune System |
| CTNNB1 | catenin (cadherin-associated protein), beta 1, 88 kDa | mRNA | Lymphocyte Trafficking; Lymphocyte Activation; Innate Immune System; Host-pathogen Interaction |
| ITGAL | integrin, alpha L (antigen CD11A (p180), lymphocyte function-associated antigen 1; alpha polypeptide) | mRNA | Lymphocyte Trafficking; Lymphocyte Activation; Innate Immune System; Host-pathogen Interaction; Hemostasis; Cell Adhesion; Adaptive Immune System |
| MR1 | major histocompatibility complex, class I-related | mRNA | MHC Class I Antigen Presentation |

SUPPLEMENTARY TABLE 3-continued

Summary of Nanostring Array RNA Biomarkers

| Abbreviation | Name | Type | Relevance |
|---|---|---|---|
| LILRA6 | leukocyte immunoglobulin-like receptor, subfamily A (with TM domain), member 6 | mRNA | MHC Class I Antigen Presentation; Adaptive Immune System |
| TAPBP | TAP binding protein (tapasin) | mRNA | MHC Class I Antigen Presentation; Adaptive Immune System |
| UBE2L3 | ubiquitin-conjugating enzyme E2L3 | mRNA | MHC Class I Antigen Presentation; Adaptive Immune System |
| BCAP31 | B-cell receptor-associated protein 31 | mRNA | MHC Class I Antigen Presentation; Host-pathogen Interaction; Apoptosis; Adaptive Immune System |
| ATG7 | ATG7 autophagy related 7 homolog (S. cerevisiae) | mRNA | MHC Class I Antigen Presentation; Innate Immune System; Autophagy; Adaptive Immune System |
| ZBTB16 | zinc finger and BTB domain containing 16 | mRNA | MHC Class I Antigen Presentation; Lymphocyte Activation; Adaptive Immune System |
| LAG3 | lymphocyte-activation gene 3 | mRNA | MHC Class II Antigen Presentation; Lymphocyte Activation; Adaptive Immune System |
| CD74 | CD74 molecule, major histocompatibility complex, class II invariant chain | mRNA | MHC Class II Antigen Presentation; Lymphocyte Activation; Host-pathogen Interaction; Hemostasis; Adaptive Immune System |
| IKBKAP | inhibitor of kappa light polypeptide gene enhancer in B-cells, kinase complex-associated protein | mRNA | NF-kB Signaling |
| TAGAP | T-cell activation RhoGTPase activating protein | mRNA | NF-kB Signaling |
| TNFRSF11A | tumor necrosis factor receptor superfamily, member 11a, NFKB activator | mRNA | NF-kB Signaling; Cytokine Signaling |
| CCL13 | chemokine (C-C motif) ligand 13 | mRNA | NF-kB Signaling; Cytokine Signaling; Chemokine Signaling |
| LTBR | lymphotoxin beta receptor (TNFR superfamily, member 3) | mRNA | NF-kB Signaling; Host-pathogen Interaction; Cytokine Signaling |
| PLAU | plasminogen activator, urokinase | mRNA | NF-kB Signaling; Innate Immune System; Hemostasis; Complement System |
| TNFSF11 | tumor necrosis factor (ligand) superfamily, member 11 | mRNA | NF-kB Signaling; Lymphocyte Activation; Cytokine Signaling |
| TNFSF13B | tumor necrosis factor (ligand) superfamily, member 13b | mRNA | NF-kB Signaling; Lymphocyte Activation; Cytokine Signaling |

SUPPLEMENTARY TABLE 3-continued

Summary of Nanostring Array RNA Biomarkers

| Abbreviation | Name | Type | Relevance |
|---|---|---|---|
| BLNK | B-cell linker | mRNA | NF-kB Signaling; Lymphocyte Activation; Cytokine Signaling; B cell Receptor Signaling; Adaptive Immune System |
| ATM | ataxia telangiectasia mutated | mRNA | NF-kB Signaling; Lymphocyte Activation; Host-pathogen Interaction; Apoptosis |
| TNFRSF13C | tumor necrosis factor receptor superfamily, member 13C | mRNA | NF-kB Signaling; Lymphocyte Activation; Host-pathogen Interaction; Cytokine Signaling |
| SYK | spleen tyrosine kinase | mRNA | NF-kB Signaling; Lymphocyte Activation; Innate Immune System; Host-pathogen Interaction; Hemostasis; Cytokine Signaling; B cell Receptor Signaling; Adaptive Immune System |
| CXCL12 | chemokine (C-X-C motif) ligand 12 | mRNA | NF-kB Signaling; Lymphocyte Trafficking; Cytokine Signaling; Chemokine Signaling |
| ATG16L1 | ATG16 autophagy related 16-like 1 (*S. cerevisiae*) | mRNA | NLR signaling; Autophagy |
| IFI16 | interferon, gamma-inducible protein 16 | mRNA | NLR signaling; Innate Immune System |
| CASP2 | caspase 2, apoptosis-related cysteine peptidase | mRNA | NLR signaling; Innate Immune System; Apoptosis |
| ATG12 | ATG12 autophagy related 12 homolog (*S. cerevisiae*) | mRNA | NLR signaling; Innate Immune System; Autophagy |
| CAMP | cathelicidin antimicrobial peptide | mRNA | NLR signaling; Innate Immune System; Host-pathogen Interaction |
| CARD9 | caspase recruitment domain family, member 9 | mRNA | NLR signaling; Innate Immune System; Host-pathogen Interaction |
| TMEM173 | transmembrane protein 173 | mRNA | NLR signaling; Innate Immune System; Host-pathogen Interaction |
| CASP1 | caspase 1, apoptosis-related cysteine peptidase (interleukin 1, beta, convertase) | mRNA | NLR signaling; Innate Immune System; Inflammasomes; Host-pathogen Interaction; Cytokine Signaling |

SUPPLEMENTARY TABLE 3-continued

Summary of Nanostring Array RNA Biomarkers

| Abbreviation | Name | Type | Relevance |
| --- | --- | --- | --- |
| IL18 | interleukin 18 (interferon-gamma-inducing factor) | mRNA | NLR signaling; Lymphocyte Activation; Host-pathogen Interaction; Cytokine Signaling |
| ATG5 | ATG5 autophagy related 5 homolog (S. cerevisiae) | mRNA | NLR signaling; Lymphocyte Activation; Innate Immune System; Host-pathogen Interaction; Autophagy |
| NLRP3 | NLR family, pyrin domain containing 3 | mRNA | NLR signaling; Lymphocyte Activation; Innate Immune System; Inflammasomes; Host-pathogen Interaction |
| PYCARD | PYD and CARD domain containing | mRNA | NLR signaling; Lymphocyte Activation; Innate Immune System; Inflammasomes; Host-pathogen Interaction |
| IL18RAP | interleukin 18 receptor accessory protein | mRNA | Oxidative Stress; Cytokine Signaling |
| MCL1 | myeloid cell leukemia sequence 1 (BCL2-related) | mRNA | Oxidative Stress; Cytokine Signaling; Apoptosis |
| PDGFRB | platelet-derived growth factor receptor, beta polypeptide | mRNA | Oxidative Stress; Host-pathogen Interaction; Cytokine Signaling |
| FN1 | fibronectin 1 | mRNA | Oxidative Stress; Host-pathogen Interaction; Hemostasis; Cytokine Signaling |
| ARG1 | arginase, liver | mRNA | Oxidative Stress; Innate Immune System; Immuno-metabolism; Host-pathogen Interaction |
| CCR7 | chemokine (C-C motif) receptor 7 | mRNA | Oxidative Stress; Lymphocyte Activation; Cytokine Signaling; Chemokine Signaling |
| SRC | v-src sarcoma (Schmidt-Ruppin A-2) viral oncogene homolog (avian) | mRNA | Oxidative Stress; Lymphocyte Activation; Host-pathogen Interaction; Chemokine Signaling |
| ADA | adenosine deaminase | mRNA | Oxidative Stress; Lymphocyte Activation; Immuno-metabolism |
| ABL1 | c-abl oncogene 1, non-receptor tyrosine kinase | mRNA | Oxidative Stress; Lymphocyte Activation; Innate Immune System; Host-pathogen Interaction; Hemostasis |

SUPPLEMENTARY TABLE 3-continued

Summary of Nanostring Array RNA Biomarkers

| Abbreviation | Name | Type | Relevance |
| --- | --- | --- | --- |
| CCL19 | chemokine (C-C motif) ligand 19 | mRNA | Oxidative Stress; NF-kB Signaling; Lymphocyte Activation; Cytokine Signaling; Chemokine Signaling |
| BCL2 | B-cell CLL/lymphoma 2 | mRNA | Oxidative Stress; NLR signaling; NF-kB Signaling; Lymphocyte Activation; Innate Immune System; Inflammasomes; Host-pathogen Interaction; Cytokine Signaling; Autophagy; Apoptosis |
| CD163 | CD163 molecule | mRNA | Phagocytosis and Degradation |
| CD164 | CD164 molecule, sialomucin | mRNA | Phagocytosis and Degradation |
| LAMP3 | lysosomal-associated membrane protein 3 | mRNA | Phagocytosis and Degradation |
| LITAF | lipopolysaccharide-induced TNF factor | mRNA | Phagocytosis and Degradation |
| MARCO | macrophage receptor with collagenous structure | mRNA | Phagocytosis and Degradation |
| MSR1 | macrophage scavenger receptor 1 | mRNA | Phagocytosis and Degradation |
| TFRC | transferrin receptor (p90, CD71) | mRNA | Phagocytosis and Degradation |
| FCGR2A/C | Fc fragment of IgG, low affinity IIa, receptor (CD32)/Fc fragment of IgG, low affinity IIc, receptor for (CD32) | mRNA | Phagocytosis and Degradation; Host-pathogen Interaction |
| FCGR2B | Fc fragment of IgG, low affinity IIb, receptor (CD32) | mRNA | Phagocytosis and Degradation; Host-pathogen Interaction; B cell Receptor Signaling; Adaptive Immune System |
| ITGA5 | integrin, alpha 5 (fibronectin receptor, alpha polypeptide) | mRNA | Phagocytosis and Degradation; Host-pathogen Interaction; Hemostasis |
| IGF2R | insulin-like growth factor 2 receptor | mRNA | Phagocytosis and Degradation; Innate Immune System |
| CTSG | cathepsin G | mRNA | Phagocytosis and Degradation; Innate Immune System; Host-pathogen Interaction |
| FCAR | Fc fragment of IgA, receptor for | mRNA | Phagocytosis and Degradation; Innate Immune System; Host-pathogen Interaction |
| FCGR2A | Fc fragment of IgG, low affinity IIa, receptor (CD32) | mRNA | Phagocytosis and Degradation; Innate Immune System; Host-pathogen Interaction |
| C1R | complement component 1, r subcomponent | mRNA | Phagocytosis and Degradation; Innate Immune System; Host-pathogen Interaction; Complement System |

SUPPLEMENTARY TABLE 3-continued

Summary of Nanostring Array RNA Biomarkers

| Abbreviation | Name | Type | Relevance |
| --- | --- | --- | --- |
| C3 | complement component 3 | mRNA | Phagocytosis and Degradation; Innate Immune System; Host-pathogen Interaction; Complement System; Adaptive Immune System |
| CLEC7A | C-type lectin domain family 7, member A | mRNA | Phagocytosis and Degradation; Lymphocyte Activation; Innate Immune System; Host-pathogen Interaction |
| FCGR3A/B | Fc fragment of IgG, low affinity IIIa, receptor (CD16a)/Fc fragment of IgG, low affinity IIIb, receptor (CD16a) | mRNA | Phagocytosis and Degradation; Lymphocyte Activation; Innate Immune System; Host-pathogen Interaction |
| CD209 | CD209 molecule | mRNA | Phagocytosis and Degradation; Lymphocyte Activation; Innate Immune System; Host-pathogen Interaction; Adaptive Immune System |
| ITGB1 | integrin, beta 1 (fibronectin receptor, beta polypeptide, antigen CD29 includes MDF2, MSK12) | mRNA | Phagocytosis and Degradation; Lymphocyte Trafficking; Lymphocyte Activation; Host-pathogen Interaction; Hemostasis; Cytokine Signaling; Cell Adhesion; Adaptive Immune System |
| MRC1 | mannose receptor, C type 1 | mRNA | Phagocytosis and Degradation; MHC Class I Antigen Presentation; Host-pathogen Interaction; Adaptive Immune System |
| TAP1 | transporter 1, ATP-binding cassette, sub-family B (MDR/TAP) | mRNA | Phagocytosis and Degradation; MHC Class I Antigen Presentation; Host-pathogen Interaction; Adaptive Immune System |
| TAP2 | transporter 2, ATP-binding cassette, sub-family B (MDR/TAP) | mRNA | Phagocytosis and Degradation; MHC Class I Antigen Presentation; Host-pathogen Interaction; Adaptive Immune System |
| NCF4 | neutrophil cytosolic factor 4, 40 kDa | mRNA | Phagocytosis and Degradation; MHC Class I Antigen Presentation; Lymphocyte Trafficking; Innate Immune System; Host-pathogen Interaction; Adaptive Immune System |

SUPPLEMENTARY TABLE 3-continued

Summary of Nanostring Array RNA Biomarkers

| Abbreviation | Name | Type | Relevance |
|---|---|---|---|
| HLA-DMA | major histocompatibility complex, class II, DM alpha | mRNA | Phagocytosis and Degradation; MHC Class II Antigen Presentation; Host-pathogen Interaction; Cell Adhesion |
| HLA-DOB | major histocompatibility complex, class II, DO beta | mRNA | Phagocytosis and Degradation; MHC Class II Antigen Presentation; Host-pathogen Interaction; Cell Adhesion; Adaptive Immune System |
| CTSC | cathepsin C | mRNA | Phagocytosis and Degradation; MHC Class II Antigen Presentation; Innate Immune System; Apoptosis; Adaptive Immune System |
| HLA-DMB | major histocompatibility complex, class II, DM beta | mRNA | Phagocytosis and Degradation; MHC Class II Antigen Presentation; Lymphocyte Activation; Host-pathogen Interaction; Cell Adhesion; Adaptive Immune System |
| MBL2 | mannose-binding lectin (protein C) 2, soluble | mRNA | Phagocytosis and Degradation; Oxidative Stress; Innate Immune System; Host-pathogen Interaction; Complement System |
| CYBB | cytochrome b-245, beta polypeptide | mRNA | Phagocytosis and Degradation; Oxidative Stress; NLR signaling; MHC Class I Antigen Presentation; Lymphocyte Trafficking; Innate Immune System; Host-pathogen Interaction; Adaptive Immune System |
| PTPN22 | protein tyrosine phosphatase, non-receptor type 22 (lymphoid) | mRNA | T Cell Receptor Signaling; Lymphocyte Activation; Adaptive Immune System |
| ICOS | inducible T-cell co-stimulator | mRNA | T Cell Receptor Signaling; Lymphocyte Activation; Cell Adhesion |
| CD8A | CD8a molecule | mRNA | T Cell Receptor Signaling; Lymphocyte Activation; Cell Adhesion; Adaptive Immune System |
| CD8B | CD8b molecule | mRNA | T Cell Receptor Signaling; Lymphocyte Activation; Cell Adhesion; Adaptive Immune System |

SUPPLEMENTARY TABLE 3-continued

Summary of Nanostring Array RNA Biomarkers

| Abbreviation | Name | Type | Relevance |
|---|---|---|---|
| CTLA4_all | cytotoxic T-lymphocyte-associated protein 4 | mRNA | T Cell Receptor Signaling; Lymphocyte Activation; Cell Adhesion; Adaptive Immune System |
| CTLA4-TM | cytotoxic T-lymphocyte-associated protein 4 | mRNA | T Cell Receptor Signaling; Lymphocyte Activation; Cell Adhesion; Adaptive Immune System |
| PDCD1 | programmed cell death 1 | mRNA | T Cell Receptor Signaling; Lymphocyte Activation; Cell Adhesion; Adaptive Immune System |
| sCTLA4 | cytotoxic T-lymphocyte-associated protein 4 | mRNA | T Cell Receptor Signaling; Lymphocyte Activation; Cell Adhesion; Adaptive Immune System |
| CD247 | CD247 molecule | mRNA | T Cell Receptor Signaling; Lymphocyte Activation; Host-pathogen Interaction |
| CD3D | CD3d molecule, delta (CD3-TCR complex) | mRNA | T Cell Receptor Signaling; Lymphocyte Activation; Host-pathogen Interaction; Adaptive Immune System |
| CD3E | CD3e molecule, epsilon (CD3-TCR complex) | mRNA | T Cell Receptor Signaling; Lymphocyte Activation; Host-pathogen Interaction; Adaptive Immune System |
| CD28 | CD28 molecule | mRNA | T Cell Receptor Signaling; Lymphocyte Activation; Host-pathogen Interaction; Cell Adhesion; Adaptive Immune System |
| CD45R0 | protein tyrosine phosphatase, receptor type, C | mRNA | T Cell Receptor Signaling; Lymphocyte Activation; Innate Immune System; Cell Adhesion; Adaptive Immune System |
| CD45RA | protein tyrosine phosphatase, receptor type, C | mRNA | T Cell Receptor Signaling; Lymphocyte Activation; Innate Immune System; Cell Adhesion; Adaptive Immune System |
| CD45RB | protein tyrosine phosphatase, receptor type, C | mRNA | T Cell Receptor Signaling; Lymphocyte Activation; Innate Immune System; Cell Adhesion; Adaptive Immune System |
| PTPRC_all | protein tyrosine phosphatase, receptor type, C | mRNA | T Cell Receptor Signaling; Lymphocyte Activation; Innate Immune System; Cell Adhesion; Adaptive Immune System |

SUPPLEMENTARY TABLE 3-continued

Summary of Nanostring Array RNA Biomarkers

| Abbreviation | Name | Type | Relevance |
|---|---|---|---|
| CD4 | CD4 molecule | mRNA | T Cell Receptor Signaling; Lymphocyte Activation; Innate Immune System; Cytokine Signaling; Cell Adhesion; Adaptive Immune System |
| LCP2 | lymphocyte cytosolic protein 2 (SH2 domain containing leukocyte protein of 76 kDa) | mRNA | T Cell Receptor Signaling; Lymphocyte Activation; Innate Immune System; Hemostasis; Adaptive Immune System |
| FYN | FYN oncogene related to SRC, FGR, YES | mRNA | T Cell Receptor Signaling; Lymphocyte Activation; Innate Immune System; Host-pathogen Interaction; Hemostasis; Cytokine Signaling; B cell Receptor Signaling; Adaptive Immune System |
| HRAS | v-Ha-ras Harvey rat sarcoma viral oncogene homolog | mRNA | T Cell Receptor Signaling; Lymphocyte Activation; Innate Immune System; Host-pathogen Interaction; Hemostasis; Cytokine Signaling; Chemokine Signaling; B cell Receptor Signaling; Autophagy; Apoptosis; Adaptive Immune System |
| RAF1 | v-raf-1 murine leukemia viral oncogene homolog 1 | mRNA | T Cell Receptor Signaling; Lymphocyte Activation; Innate Immune System; Host-pathogen Interaction; Hemostasis; Cytokine Signaling; Chemokine Signaling; B cell Receptor Signaling; Autophagy; Apoptosis; Adaptive Immune System |
| ZAP70 | zeta-chain (TCR) associated protein kinase 70 kDa | mRNA | T Cell Receptor Signaling; NF-kB Signaling; Lymphocyte Activation; Adaptive Immune System |
| CD40LG | CD40 ligand | mRNA | T Cell Receptor Signaling; NF-kB Signaling; Lymphocyte Activation; Host-pathogen Interaction; Cytokine Signaling; Cell Adhesion; Adaptive Immune System |
| BCL10 | B-cell CLL/lymphoma 10 | mRNA | T Cell Receptor Signaling; NF-kB Signaling; Lymphocyte Activation; Innate |

SUPPLEMENTARY TABLE 3-continued

Summary of Nanostring Array RNA Biomarkers

| Abbreviation | Name | Type | Relevance |
|---|---|---|---|
| MALT1 | mucosa associated lymphoid tissue lymphoma translocation gene 1 | mRNA | Immune System; Host-pathogen Interaction; B cell Receptor Signaling; Adaptive Immune System |
| LCK | lymphocyte-specific protein tyrosine kinase | mRNA | T Cell Receptor Signaling; NF-kB Signaling; Lymphocyte Activation; Innate Immune System; Host-pathogen Interaction; B cell Receptor Signaling; Adaptive Immune System |
| PSMB7 | proteasome (prosome, macropain) subunit, beta type, 7 | mRNA | T Cell Receptor Signaling; NF-kB Signaling; Lymphocyte Activation; Innate Immune System; Host-pathogen Interaction; Hemostasis; Cytokine Signaling; Adaptive Immune System |
| PSMB9 | proteasome (prosome, macropain) subunit, beta type, 9 (large multifunctional peptidase 2) | mRNA | T Cell Receptor Signaling; NF-kB Signaling; MHC Class I Antigen Presentation; Innate Immune System; Immuno-metabolism; Cytokine Signaling; B cell Receptor Signaling; Apoptosis; Adaptive Immune System |
| PSMC2 | proteasome (prosome, macropain) 26S subunit, ATPase, 2 | mRNA | T Cell Receptor Signaling; NF-kB Signaling; MHC Class I Antigen Presentation; Innate Immune System; Immuno-metabolism; Cytokine Signaling; B cell Receptor Signaling; Apoptosis; Adaptive Immune System |
| PSMD7 | proteasome (prosome, macropain) 26S subunit, non-ATPase, 7 | mRNA | T Cell Receptor Signaling; NF-kB Signaling; MHC Class I Antigen Presentation; Innate Immune System; Immuno-metabolism; Host-pathogen Interaction; Cytokine Signaling; B cell Receptor Signaling; Apoptosis; Adaptive Immune System |
| | | | T Cell Receptor Signaling; NF-kB Signaling; MHC Class I Antigen Presentation; Innate Immune |

SUPPLEMENTARY TABLE 3-continued

Summary of Nanostring Array RNA Biomarkers

| Abbreviation | Name | Type | Relevance |
|---|---|---|---|
| PSMB10 | proteasome (prosome, macropain) subunit, beta type, 10 | mRNA | System; Immuno-metabolism; Host-pathogen Interaction; Cytokine Signaling; B cell Receptor Signaling; Apoptosis; Adaptive Immune System T Cell Receptor Signaling; NF-kB Signaling; MHC Class I Antigen Presentation; Lymphocyte Activation; Innate Immune System; Immuno-metabolism; Cytokine Signaling; B cell Receptor Signaling; Apoptosis; Adaptive Immune System |
| PSMB5 | proteasome (prosome, macropain) subunit, beta type, 5 | mRNA | T Cell Receptor Signaling; Oxidative Stress; NF-kB Signaling; MHC Class I Antigen Presentation; Innate Immune System; Immuno-metabolism; Cytokine Signaling; B cell Receptor Signaling; Apoptosis; Adaptive Immune System |
| SKI | v-ski sarcoma viral oncogene homolog (avian) | mRNA | TGF-b Signaling |
| SMAD5 | SMAD family member 5 | mRNA | TGF-b Signaling |
| IL17A | interleukin 17A | mRNA | Th17 Differentiation; Cytokine Signaling |
| IL17F | interleukin 17F | mRNA | Th17 Differentiation; Cytokine Signaling |
| IL1RAP | interleukin 1 receptor accessory protein | mRNA | Th17 Differentiation; Cytokine Signaling |
| IL22 | interleukin 22 | mRNA | Th17 Differentiation; Cytokine Signaling |
| IL6R | interleukin 6 receptor | mRNA | Th17 Differentiation; Cytokine Signaling |
| IL21 | interleukin 21 | mRNA | Th17 Differentiation; Lymphocyte Activation; Cytokine Signaling |
| IL21R | interleukin 21 receptor | mRNA | Th17 Differentiation; Lymphocyte Activation; Cytokine Signaling |
| IL23R | interleukin 23 receptor | mRNA | Th17 Differentiation; Lymphocyte Activation; Cytokine Signaling |
| IL6ST | interleukin 6 signal transducer (gp130, oncostatin M receptor) | mRNA | Th17 Differentiation; Lymphocyte Activation; Cytokine Signaling |

SUPPLEMENTARY TABLE 3-continued

Summary of Nanostring Array RNA Biomarkers

| Abbreviation | Name | Type | Relevance |
| --- | --- | --- | --- |
| IL23A | interleukin 23, alpha subunit p19 | mRNA | Th17 Differentiation; Lymphocyte Activation; Host-pathogen Interaction; Cytokine Signaling |
| IL1R1 | interleukin 1 receptor, type I | mRNA | Th17 Differentiation; Oxidative Stress; NF-kB Signaling; Host-pathogen Interaction; Cytokine Signaling |
| IL12RB1 | interleukin 12 receptor, beta 1 | mRNA | Th17 Differentiation; Th1 Differentiation; Lymphocyte Activation; Cytokine Signaling |
| NOTCH1 | notch 1 | mRNA | Th2 Differentiation; Host-pathogen Interaction |
| IL4R | interleukin 4 receptor | mRNA | Th2 Differentiation; Lymphocyte Activation; Cytokine Signaling |
| NOTCH2 | notch 2 | mRNA | Th2 Differentiation; Lymphocyte Activation; Host-pathogen Interaction |
| IL13 | interleukin 13 | mRNA | Th2 Differentiation; Lymphocyte Activation; Host-pathogen Interaction; Cytokine Signaling |
| IL2RA | interleukin 2 receptor, alpha | mRNA | Th2 Differentiation; Lymphocyte Activation; Host-pathogen Interaction; Hemostasis; Cytokine Signaling |
| IL2RB | interleukin 2 receptor, beta | mRNA | Th2 Differentiation; Lymphocyte Activation; Host-pathogen Interaction; Hemostasis; Cytokine Signaling |
| IL5 | interleukin 5 (colony-stimulating factor, eosinophil) | mRNA | Th2 Differentiation; T Cell Receptor Signaling; Lymphocyte Activation; Hemostasis; Cytokine Signaling |
| IL4 | interleukin 4 | mRNA | Th2 Differentiation; T Cell Receptor Signaling; Lymphocyte Activation; Host-pathogen Interaction; Cytokine Signaling |

SUPPLEMENTARY TABLE 3-continued

Summary of Nanostring Array RNA Biomarkers

| Abbreviation | Name | Type | Relevance |
|---|---|---|---|
| IL2 | interleukin 2 | mRNA | Th2 Differentiation; Th1 Differentiation; T Cell Receptor Signaling; Lymphocyte Activation; Host-pathogen Interaction; Hemostasis; Cytokine Signaling |
| IL2RG | interleukin 2 receptor, gamma | mRNA | Th2 Differentiation; Th17 Differentiation; Host-pathogen Interaction; Hemostasis; Cytokine Signaling |
| JAK3 | Janus kinase 3 | mRNA | Th2 Differentiation; Th17 Differentiation; Lymphocyte Activation; Host-pathogen Interaction; Hemostasis; Cytokine Signaling; Chemokine Signaling |
| CXCL11 | chemokine (C-X-C motif) ligand 11 | mRNA | TLR Signaling; Cytokine Signaling; Chemokine Signaling |
| CXCL9 | chemokine (C-X-C motif) ligand 9 | mRNA | TLR Signaling; Cytokine Signaling; Chemokine Signaling |
| SPP1 | secreted phosphoprotein 1 | mRNA | TLR Signaling; Host-pathogen Interaction |
| CCL3 | chemokine (C-C motif) ligand 3 | mRNA | TLR Signaling; Host-pathogen Interaction; Cytokine Signaling; Chemokine Signaling |
| S100A8 | S100 calcium binding protein A8 | mRNA | TLR Signaling; Innate Immune System |
| S100A9 | S100 calcium binding protein A9 | mRNA | TLR Signaling; Innate Immune System |
| TLR8 | toll-like receptor 8 | mRNA | TLR Signaling; Innate Immune System |
| DUSP4 | dual specificity phosphatase 4 | mRNA | TLR Signaling; Innate Immune System; Cytokine Signaling |
| IRAK3 | interleukin-1 receptor-associated kinase 3 | mRNA | TLR Signaling; Innate Immune System; Cytokine Signaling |
| SIGIRR | single immunoglobulin and toll-interleukin 1 receptor (TIR) domain | mRNA | TLR Signaling; Innate Immune System; Cytokine Signaling |
| TOLLIP | toll interacting protein | mRNA | TLR Signaling; Innate Immune System; Cytokine Signaling |

SUPPLEMENTARY TABLE 3-continued

Summary of Nanostring Array RNA Biomarkers

| Abbreviation | Name | Type | Relevance |
|---|---|---|---|
| TLR3 | toll-like receptor 3 | mRNA | TLR Signaling; Innate Immune System; Host-pathogen Interaction |
| TLR5 | toll-like receptor 5 | mRNA | TLR Signaling; Innate Immune System; Host-pathogen Interaction |
| TLR7 | toll-like receptor 7 | mRNA | TLR Signaling; Innate Immune System; Host-pathogen Interaction |
| TLR9 | toll-like receptor 9 | mRNA | TLR Signaling; Innate Immune System; Host-pathogen Interaction |
| MAPKAPK2 | mitogen-activated protein kinase-activated protein kinase 2 | mRNA | TLR Signaling; Innate Immune System; Immuno-metabolism; Cytokine Signaling |
| CD80 | CD80 molecule | mRNA | TLR Signaling; Lymphocyte Activation; Cytokine Signaling; Cell Adhesion; Adaptive Immune System |
| CD86 | CD86 molecule | mRNA | TLR Signaling; Lymphocyte Activation; Cytokine Signaling; Cell Adhesion; Adaptive Immune System |
| TLR1 | toll-like receptor 1 | mRNA | TLR Signaling; MHC Class I Antigen Presentation; Innate Immune System; Host-pathogen Interaction; Adaptive Immune System |
| CCL4 | chemokine (C-C motif) ligand 4 | mRNA | TLR Signaling; NF-kB Signaling; Host-pathogen Interaction; Cytokine Signaling; Chemokine Signaling |
| CD40 | CD40 molecule, TNF receptor superfamily member 5 | mRNA | TLR Signaling; NF-kB Signaling; Lymphocyte Activation; Host-pathogen Interaction; Cytokine Signaling; Cell Adhesion |

SUPPLEMENTARY TABLE 3-continued

Summary of Nanostring Array RNA Biomarkers

| Abbreviation | Name | Type | Relevance |
| --- | --- | --- | --- |
| LY96 | lymphocyte antigen 96 | mRNA | TLR Signaling; NF-kB Signaling; MHC Class I Antigen Presentation; Innate Immune System; Host-pathogen Interaction; Apoptosis; Adaptive Immune System |
| BTK | Bruton agammaglobulinemia tyrosine kinase | mRNA | TLR Signaling; NF-kB Signaling; MHC Class I Antigen Presentation; Lymphocyte Activation; Innate Immune System; B cell Receptor Signaling; Adaptive Immune System |
| TIRAP | toll-interleukin 1 receptor (TIR) domain containing adaptor protein | mRNA | TLR Signaling; NF-kB Signaling; MHC Class I Antigen Presentation; Lymphocyte Activation; Innate Immune System; Host-pathogen Interaction; Adaptive Immune System |
| IKBKE | inhibitor of kappa light polypeptide gene enhancer in B-cells, kinase epsilon | mRNA | TLR Signaling; NLR signaling; Innate Immune System; Host-pathogen Interaction |
| IRAK2 | interleukin-1 receptor-associated kinase 2 | mRNA | TLR Signaling; NLR signaling; Innate Immune System; Host-pathogen Interaction; Cytokine Signaling |
| NOD1 | nucleotide-binding oligomerization domain containing 1 | mRNA | TLR Signaling; NLR signaling; Innate Immune System; Host-pathogen Interaction; Cytokine Signaling |
| TBK1 | TANK-binding kinase 1 | mRNA | TLR Signaling; NLR signaling; Lymphocyte Activation; Innate Immune System; Host-pathogen Interaction; Cytokine Signaling |
| IL8 | interleukin 8 | mRNA | TLR Signaling; NLR signaling; NF-kB Signaling; Host-pathogen Interaction; Cytokine Signaling; Chemokine Signaling |

SUPPLEMENTARY TABLE 3-continued

Summary of Nanostring Array RNA Biomarkers

| Abbreviation | Name | Type | Relevance |
|---|---|---|---|
| IRAK1 | interleukin-1 receptor-associated kinase 1 | mRNA | TLR Signaling; NLR signaling; NF-kB Signaling; Innate Immune System; Host-pathogen Interaction; Cytokine Signaling |
| IRAK4 | interleukin-1 receptor-associated kinase 4 | mRNA | TLR Signaling; NLR signaling; NF-kB Signaling; Innate Immune System; Host-pathogen Interaction; Cytokine Signaling |
| TICAM1 | toll-like receptor adaptor molecule 1 | mRNA | TLR Signaling; NLR signaling; NF-kB Signaling; Lymphocyte Activation; Innate Immune System; Host-pathogen Interaction; Apoptosis |
| MYD88 | myeloid differentiation primary response gene (88) | mRNA | TLR Signaling; NLR signaling; NF-kB Signaling; MHC Class I Antigen Presentation; Lymphocyte Activation; Innate Immune System; Host-pathogen Interaction; Cytokine Signaling; Adaptive Immune System |
| APP | amyloid beta (A4) precursor protein | mRNA | TLR Signaling; Oxidative Stress; NLR signaling; Innate Immune System; Inflammasomes; Hemostasis; Cytokine Signaling |
| ITGAM | integrin, alpha M (complement component 3 receptor 3 subunit) | mRNA | TLR Signaling; Phagocytosis and Degradation; Lymphocyte Trafficking; Innate Immune System; Host-pathogen Interaction; Hemostasis; Cytokine Signaling; Complement System; Cell Adhesion |
| ITGB2 | integrin, beta 2 (complement component 3 receptor 3 and 4 subunit) | mRNA | TLR Signaling; Phagocytosis and Degradation; Lymphocyte Trafficking; Lymphocyte Activation; Innate Immune System; Host-pathogen Interaction; Hemostasis; Cytokine Signaling; Complement System; Cell Adhesion; Adaptive Immune System |

SUPPLEMENTARY TABLE 3-continued

Summary of Nanostring Array RNA Biomarkers

| Abbreviation | Name | Type | Relevance |
|---|---|---|---|
| TLR2 | toll-like receptor 2 | mRNA | TLR Signaling; Phagocytosis and Degradation; MHC Class I Antigen Presentation; Innate Immune System; Host-pathogen Interaction; Adaptive Immune System |
| CTSS | cathepsin S | mRNA | TLR Signaling; Phagocytosis and Degradation; MHC Class II Antigen Presentation; MHC Class I Antigen Presentation; Innate Immune System; Host-pathogen Interaction; Apoptosis; Adaptive Immune System |
| CD14 | CD14 molecule | mRNA | TLR Signaling; Phagocytosis and Degradation; NF-kB Signaling; MHC Class I Antigen Presentation; Innate Immune System; Host-pathogen Interaction; Apoptosis; Adaptive Immune System |
| TLR4 | toll-like receptor 4 | mRNA | TLR Signaling; Phagocytosis and Degradation; NLR signaling; NF-kB Signaling; MHC Class I Antigen Presentation; Lymphocyte Activation; Innate Immune System; Host-pathogen Interaction; Apoptosis; Adaptive Immune System |
| CD36 | CD36 molecule (thrombospondin receptor) | mRNA | TLR Signaling; Phagocytosis and Degradation; Oxidative Stress; MHC Class I Antigen Presentation; Innate Immune System; Immuno metabolism; Host-pathogen Interaction; Hemostasis; Cytokine Signaling; Adaptive Immune System |
| TRAF6 | TNF receptor-associated factor 6 | mRNA | TLR Signaling; T Cell Receptor Signaling; NLR signaling; NF-kB Signaling; Lymphocyte Activation; Innate Immune System; Host-pathogen Interaction; Cytokine Signaling; Autophagy; |

SUPPLEMENTARY TABLE 3-continued

Summary of Nanostring Array RNA Biomarkers

| Abbreviation | Name | Type | Relevance |
|---|---|---|---|
| IL12A | interleukin 12A (natural killer cell stimulatory factor 1, cytotoxic lymphocyte maturation factor 1, p35) | mRNA | Adaptive Immune System TLR Signaling; Th1 Differentiation; Lymphocyte Activation; Host-pathogen Interaction; Cytokine Signaling |
| IL12B | interleukin 12B (natural killer cell stimulatory factor 2, cytotoxic lymphocyte maturation factor 2, p40) | mRNA | TLR Signaling; Th17 Differentiation; Th1 Differentiation; Lymphocyte Activation; Host-pathogen Interaction; Cytokine Signaling |
| CXCL10 | chemokine (C-X-C motif) ligand 10 | mRNA | TLR Signaling; TNF Family Signaling; Host-pathogen Interaction; Cytokine Signaling; Chemokine Signaling |
| CASP8 | caspase 8, apoptosis-related cysteine peptidase | mRNA | TLR Signaling; TNF Family Signaling; NLR signaling; Lymphocyte Activation; Innate Immune System; Host-pathogen Interaction; Apoptosis |
| FADD | Fas (TNFRSF6)-associated via death domain | mRNA | TLR Signaling; TNF Family Signaling; NLR signaling; Lymphocyte Activation; Innate Immune System; Host-pathogen Interaction; Apoptosis |
| NOD2 | nucleotide-binding oligomerization domain containing 2 | mRNA | TLR Signaling; TNF Family Signaling; NLR signaling; Lymphocyte Activation; Innate Immune System; Host-pathogen Interaction; Cytokine Signaling |
| TRAF3 | TNF receptor-associated factor 3 | mRNA | TLR Signaling; TNF Family Signaling; NLR signaling; NF-kB Signaling; Innate Immune System; Host-pathogen Interaction; Cytokine Signaling |
| CCL5 | chemokine (C-C motif) ligand 5 | mRNA | TLR Signaling; TNF Family Signaling; Oxidative Stress; NLR signaling; Lymphocyte Activation; Host-pathogen Interaction; Cytokine |

SUPPLEMENTARY TABLE 3-continued

Summary of Nanostring Array RNA Biomarkers

| Abbreviation | Name | Type | Relevance |
|---|---|---|---|
| | | | Signaling; Chemokine Signaling |
| IKBKB | inhibitor of kappa light polypeptide gene enhancer in B-cells, kinase beta | mRNA | TLR Signaling; TNF Family Signaling; T Cell Receptor Signaling; NLR signaling; NF-kB Signaling; MHC Class I Antigen Presentation; Innate Immune System; Host-pathogen Interaction; Cytokine Signaling; Chemokine Signaling; B cell Receptor Signaling; Apoptosis; Adaptive Immune System |
| IKBKG | inhibitor of kappa light polypeptide gene enhancer in B-cells, kinase gamma | mRNA | TLR Signaling; TNF Family Signaling; T Cell Receptor Signaling; NLR signaling; NF-kB Signaling; MHC Class I Antigen Presentation; Innate Immune System; Host-pathogen Interaction; Cytokine Signaling; Chemokine Signaling; B cell Receptor Signaling; Apoptosis; Adaptive Immune System |
| CHUK | conserved helix-loop-helix ubiquitous kinase | mRNA | TLR Signaling; TNF Family Signaling; T Cell Receptor Signaling; Oxidative Stress; NLR signaling; NF-kB Signaling; MHC Class I Antigen Presentation; Innate Immune System; Host-pathogen Interaction; Cytokine Signaling; Chemokine Signaling; B cell Receptor Signaling; Apoptosis; Adaptive Immune System |
| MAPK1 | mitogen-activated protein kinase 1 | mRNA | TLR Signaling; TNF Family Signaling; TGF-b Signaling; T Cell Receptor Signaling; NLR signaling; Lymphocyte Activation; Innate Immune System; Host-pathogen Interaction; Hemostasis; |

SUPPLEMENTARY TABLE 3-continued

Summary of Nanostring Array RNA Biomarkers

| Abbreviation | Name | Type | Relevance |
|---|---|---|---|
| IL1B | interleukin 1, beta | mRNA | Cytokine Signaling; Chemokine Signaling; B cell Receptor Signaling; Autophagy; Apoptosis TLR Signaling; TNF Family Signaling; Th17 Differentiation; Oxidative Stress; NLR signaling; NF-kB Signaling; Lymphocyte Activation; Innate Immune System; Host-pathogen Interaction; Cytokine Signaling |
| MAPK11 | mitogen-activated protein kinase 11 | mRNA | TLR Signaling; TNF Family Signaling; Th17 Differentiation; T Cell Receptor Signaling; NLR signaling; Lymphocyte Trafficking; Innate Immune System; Host-pathogen Interaction; Cytokine Signaling |
| MAPK14 | mitogen-activated protein kinase 14 | mRNA | TLR Signaling; TNF Family Signaling; Th17 Differentiation; T Cell Receptor Signaling; NLR signaling; Lymphocyte Trafficking; Innate Immune System; Host-pathogen Interaction; Hemostasis; Cytokine Signaling |
| TNF | tumor necrosis factor | mRNA | TLR Signaling; TNF Family Signaling; Th17 Differentiation; TGF-b Signaling; T Cell Receptor Signaling; Oxidative Stress; NLR signaling; NF-kB Signaling; Lymphocyte Activation; Host-pathogen Interaction; Cytokine Signaling; Apoptosis |
| IL6 | interleukin 6 (interferon, beta 2) | mRNA | TLR Signaling; TNF Family Signaling; Th2 Differentiation; Th17 Differentiation; Oxidative Stress; NLR signaling; Lymphocyte Activation; Host-pathogen |

SUPPLEMENTARY TABLE 3-continued

Summary of Nanostring Array RNA Biomarkers

| Abbreviation | Name | Type | Relevance |
|---|---|---|---|
| | | | Interaction; Cytokine Signaling |
| MAP4K1 | mitogen-activated protein kinase kinase kinase kinase 1 | mRNA | TNF Family Signaling |
| MAP4K2 | mitogen-activated protein kinase kinase kinase kinase 2 | mRNA | TNF Family Signaling |
| MAP4K4 | mitogen-activated protein kinase kinase kinase kinase 4 | mRNA | TNF Family Signaling |
| CSF1 | colony stimulating factor 1 (macrophage) | mRNA | TNF Family Signaling; Cytokine Signaling |
| LIF | leukemia inhibitory factor (cholinergic differentiation factor) | mRNA | TNF Family Signaling; Cytokine Signaling |
| CCL20 | chemokine (C-C motif) ligand 20 | mRNA | TNF Family Signaling; Cytokine Signaling; Chemokine Signaling |
| CX3CL1 | chemokine (C-X3-C motif) ligand 1 | mRNA | TNF Family Signaling; Cytokine Signaling; Chemokine Signaling |
| SELE | selectin E | mRNA | TNF Family Signaling; Host-pathogen Interaction; Hemostasis; Cell Adhesion |
| TNFRSF1B | tumor necrosis factor receptor superfamily, member 1B | mRNA | TNF Family Signaling; Innate Immune System; Cytokine Signaling |
| CASP10 | caspase 10, apoptosis-related cysteine peptidase | mRNA | TNF Family Signaling; Innate Immune System; Host-pathogen Interaction; Apoptosis |
| IL18R1 | interleukin 18 receptor 1 | mRNA | TNF Family Signaling; Lymphocyte Activation; Cytokine Signaling |
| IL15 | interleukin 15 | mRNA | TNF Family Signaling; Lymphocyte Activation; Host-pathogen Interaction; Cytokine Signaling |
| TNFSF10 | tumor necrosis factor (ligand) superfamily, member 10 | mRNA | TNF Family Signaling; Lymphocyte Activation; Host-pathogen Interaction; Cytokine Signaling; Apoptosis |
| TRAF4 | TNF receptor-associated factor 4 | mRNA | TNF Family Signaling; NF-kB Signaling |
| TRAF1 | TNF receptor-associated factor 1 | mRNA | TNF Family Signaling; NF-kB Signaling; Host-pathogen Interaction; Apoptosis |
| LTA | lymphotoxin alpha (TNF superfamily, member 1) | mRNA | TNF Family Signaling; NF-kB Signaling; Host-pathogen Interaction; Cytokine Signaling |
| CXCL1 | chemokine (C-X-C motif) ligand 1 (melanoma growth stimulating activity, alpha) | mRNA | TNF Family Signaling; NLR signaling; Innate Immune System; Host-pathogen Interaction; Cytokine |

SUPPLEMENTARY TABLE 3-continued

Summary of Nanostring Array RNA Biomarkers

| Abbreviation | Name | Type | Relevance |
|---|---|---|---|
| CCL2 | chemokine (C-C motif) ligand 2 | mRNA | Signaling; Chemokine Signaling |
| TRAF5 | TNF receptor-associated factor 5 | mRNA | TNF Family Signaling; NLR signaling; Lymphocyte Activation; Host-pathogen Interaction; Cytokine Signaling; Chemokine Signaling |
| CXCL2 | chemokine (C-X-C motif) ligand 2 | mRNA | TNF Family Signaling; NLR signaling; NF-kB Signaling; Host-pathogen Interaction |
| CASP3 | caspase 3, apoptosis-related cysteine peptidase | mRNA | TNF Family Signaling; NLR signaling; NF-kB Signaling; Host-pathogen Interaction; Cytokine Signaling; Chemokine Signaling |
| FAS | Fas (TNF receptor superfamily, member 6) | mRNA | TNF Family Signaling; Oxidative Stress; Lymphocyte Activation; Host-pathogen Interaction; Cytokine Signaling; Apoptosis |
| PTGS2 | prostaglandin-endoperoxide synthase 2 (prostaglandin G/H synthase and cyclooxygenase) | mRNA | TNF Family Signaling; Oxidative Stress; Lymphocyte Activation; Host-pathogen Interaction; Cytokine Signaling; Apoptosis |
| TNFAIP3 | tumor necrosis factor, alpha-induced protein 3 | mRNA | TNF Family Signaling; Oxidative Stress; NF-KB Signaling; Immuno-metabolism; Host-pathogen Interaction; Cytokine Signaling |
| TRAF2 | TNF receptor-associated factor 2 | mRNA | TNF Family Signaling; Oxidative Stress; NLR signaling; NF-kB Signaling; Lymphocyte Activation; Innate Immune System; Host-pathogen Interaction |
| CSF2 | colony stimulating factor 2 (granulocyte-macrophage) | mRNA | TNF Family Signaling; Oxidative Stress; NLR signaling; NF-kB Signaling; Lymphocyte Activation; Innate Immune System; Host-pathogen Interaction; Cytokine Signaling; Apoptosis |
| | | | TNF Family Signaling; T Cell Receptor Signaling; Lymphocyte Activation; Host-pathogen Interaction; Hemostasis; Cytokine Signaling |

SUPPLEMENTARY TABLE 3-continued

Summary of Nanostring Array RNA Biomarkers

| Abbreviation | Name | Type | Relevance |
|---|---|---|---|
| BATF3 | basic leucine zipper transcription factor, ATF-like 3 | mRNA | Transcriptional Regulation |
| GFI1 | growth factor independent 1 transcription repressor | mRNA | Transcriptional Regulation |
| IKZF2 | IKAROS family zinc finger 2 (Helios) | mRNA | Transcriptional Regulation |
| ILF3 | interleukin enhancer binding factor 3, 90 kDa | mRNA | Transcriptional Regulation |
| NFIL3 | nuclear factor, interleukin 3 regulated | mRNA | Transcriptional Regulation |
| NFKBIZ | nuclear factor of kappa light polypeptide gene enhancer in B-cells inhibitor, zeta | mRNA | Transcriptional Regulation |
| PAX5 | paired box 5 | mRNA | Transcriptional Regulation |
| RUNX1 | runt-related transcription factor 1 | mRNA | Transcriptional Regulation |
| TAL1 | T-cell acute lymphocytic leukemia 1 | mRNA | Transcriptional Regulation |
| TCF4 | transcription factor 4 | mRNA | Transcriptional Regulation |
| EGR2 | early growth response 2 | mRNA | Transcriptional Regulation; Host-pathogen Interaction |
| PPARG | peroxisome proliferator-activated receptor gamma | mRNA | Transcriptional Regulation; Immuno-metabolism |
| EOMES | eomesodermin | mRNA | Transcriptional Regulation; Lymphocyte Activation |
| IKZF1 | IKAROS family zinc finger 1 (Ikaros) | mRNA | Transcriptional Regulation; Lymphocyte Activation |
| IKZF3 | IKAROS family zinc finger 3 (Aiolos) | mRNA | Transcriptional Regulation; Lymphocyte Activation |
| LEF1 | lymphoid enhancer-binding factor 1 | mRNA | Transcriptional Regulation; Lymphocyte Activation |
| POU2F2 | POU class 2 homeobox 2 | mRNA | Transcriptional Regulation; Lymphocyte Activation |
| BATF | basic leucine zipper transcription factor, ATF-like | mRNA | Transcriptional Regulation; Lymphocyte Activation; Cytokine Signaling |
| ZEB1 | zinc finger E-box binding homeobox 1 | mRNA | Transcriptional Regulation; Lymphocyte Activation; Cytokine Signaling |
| TCF7 | transcription factor 7 (T-cell specific, HMG-box) | mRNA | Transcriptional Regulation; Lymphocyte Activation; Host-pathogen Interaction |
| RELB | v-rel reticuloendotheliosis viral oncogene homolog B | mRNA | Transcriptional Regulation; NF-kB Signaling; Lymphocyte Activation; Innate Immune System; Host-pathogen Interaction; Cytokine Signaling |
| ETS1 | v-ets erythroblastosis virus E26 oncogene homolog 1 (avian) | mRNA | Transcriptional Regulation; Oxidative Stress; Host-pathogen Interaction |

SUPPLEMENTARY TABLE 3-continued

Summary of Nanostring Array RNA Biomarkers

| Abbreviation | Name | Type | Relevance |
| --- | --- | --- | --- |
| TP53 | tumor protein p53 | mRNA | Transcriptional Regulation; Oxidative Stress; Host-pathogen Interaction; Hemostasis; Cytokine Signaling; Apoptosis |
| XBP1 | X-box binding protein 1 | mRNA | Transcriptional Regulation; Oxidative Stress; Lymphocyte Activation; Host-pathogen Interaction |
| NFATC3 | nuclear factor of activated T-cells, cytoplasmic, calcineurin-dependent 3 | mRNA | Transcriptional Regulation; T Cell Receptor Signaling; Innate Immune System; Host-pathogen Interaction; B cell Receptor Signaling; Adaptive Immune System |
| NFATC1 | nuclear factor of activated T-cells, cytoplasmic, calcineurin-dependent 1 | mRNA | Transcriptional Regulation; T Cell Receptor Signaling; Lymphocyte Activation; Innate Immune System; Host-pathogen Interaction; B cell Receptor Signaling; Adaptive Immune System |
| NFATC2 | nuclear factor of activated T-cells, cytoplasmic, calcineurin-dependent 2 | mRNA | Transcriptional Regulation; T Cell Receptor Signaling; Lymphocyte Activation; Innate Immune System; Host-pathogen Interaction; B cell Receptor Signaling; Adaptive Immune System |
| STAT4 | signal transducer and activator of transcription 4 | mRNA | Transcriptional Regulation; Th1 Differentiation; Host-pathogen Interaction; Cytokine Signaling |
| TBX21 | T-box 21 | mRNA | Transcriptional Regulation; Th1 Differentiation; Lymphocyte Activation |
| RORC | RAR-related orphan receptor C | mRNA | Transcriptional Regulation; Th17 Differentiation; Lymphocyte Activation; Cytokine Signaling |
| AHR | aryl hydrocarbon receptor | mRNA | Transcriptional Regulation; Th17 Differentiation; Lymphocyte Activation; Immuno-metabolism |

SUPPLEMENTARY TABLE 3-continued

Summary of Nanostring Array RNA Biomarkers

| Abbreviation | Name | Type | Relevance |
|---|---|---|---|
| MAF | v-maf musculoaponeurotic fibrosarcoma oncogene homolog (avian) | mRNA | Transcriptional Regulation; Th2 Differentiation |
| STAT5A | signal transducer and activator of transcription 5A | mRNA | Transcriptional Regulation; Th2 Differentiation; Host-pathogen Interaction; Cytokine Signaling |
| GATA3 | GATA binding protein 3 | mRNA | Transcriptional Regulation; Th2 Differentiation; Lymphocyte Activation; Hemostasis; Cytokine Signaling |
| STAT5B | signal transducer and activator of transcription 5B | mRNA | Transcriptional Regulation; Th2 Differentiation; Lymphocyte Activation; Host-pathogen Interaction; Cytokine Signaling; Chemokine Signaling |
| STAT6 | signal transducer and activator of transcription 6, interleukin-4 induced | mRNA | Transcriptional Regulation; Th2 Differentiation; Oxidative Stress; Lymphocyte Activation; Innate Immune System; Host-pathogen Interaction; Cytokine Signaling |
| NFKB2 | nuclear factor of kappa light polypeptide gene enhancer in B-cells 2 (p49/p100) | mRNA | Transcriptional Regulation; TLR Signaling; NLR signaling; NF-kB Signaling; Innate Immune System; Inflammasomes; Host-pathogen Interaction; Cytokine Signaling |
| NFKBIA | nuclear factor of kappa light polypeptide gene enhancer in B-cells inhibitor, alpha | mRNA | Transcriptional Regulation; TLR Signaling; TNF Family Signaling; T Cell Receptor Signaling; NLR signaling; NF-kB Signaling; Innate Immune System; Host-pathogen Interaction; Cytokine Signaling; Chemokine Signaling; B cell Receptor Signaling; Apoptosis; Adaptive Immune System |
| NFKB1 | nuclear factor of kappa light polypeptide gene enhancer in B-cells 1 | mRNA | Transcriptional Regulation; TLR Signaling; TNF Family Signaling; Th1 Differentiation; T Cell Receptor Signaling; Oxidative Stress; NLR signaling; NF-kB Signaling; Innate Immune |

SUPPLEMENTARY TABLE 3-continued

Summary of Nanostring Array RNA Biomarkers

| Abbreviation | Name | Type | Relevance |
|---|---|---|---|
| RELA | v-rel reticuloendotheliosis viral oncogene homolog A (avian) | mRNA | System; Inflammasomes; Host-pathogen Interaction; Cytokine Signaling; Chemokine Signaling; B cell Receptor Signaling; Apoptosis; Adaptive Immune System Transcriptional Regulation; TLR Signaling; TNF Family Signaling; Th 1 Differentiation; T Cell Receptor Signaling; Oxidative Stress; NLR signaling; NF-kB Signaling; Innate Immune System; Inflammasomes; Host-pathogen Interaction; Cytokine Signaling; Chemokine Signaling; B cell Receptor Signaling; Apoptosis; Adaptive Immune System |
| BCL3 | B-cell CLL/lymphoma 3 | mRNA | Transcriptional Regulation; TNF Family Signaling; Lymphocyte Activation |
| CEBPB | CCAAT/enhancer binding protein (C/EBP), beta | mRNA | Transcriptional Regulation; TNF Family Signaling; Lymphocyte Activation; Host-pathogen Interaction |
| IL10RA | interleukin 10 receptor, alpha | mRNA | Treg Differentiation; Host-pathogen Interaction; Cytokine Signaling |
| IL10 | interleukin 10 | mRNA | Treg Differentiation; T Cell Receptor Signaling; Lymphocyte Activation; Host-pathogen Interaction; Cytokine Signaling |
| TGFBR1 | transforming growth factor, beta receptor 1 | mRNA | Treg Differentiation; Th17 Differentiation; TGF-b Signaling; Host-pathogen Interaction; Cytokine Signaling |
| SMAD3 | SMAD family member 3 | mRNA | Treg Differentiation; Th17 Differentiation; TGF-b Signaling; Lymphocyte Activation; Host-pathogen Interaction; Cytokine Signaling |
| TGFBR2 | transforming growth factor, beta receptor II (70/80 kDa) | mRNA | Treg Differentiation; Th17 Differentiation; TGF-b Signaling; Lymphocyte Activation; Host-pathogen |

SUPPLEMENTARY TABLE 3-continued

Summary of Nanostring Array RNA Biomarkers

| Abbreviation | Name | Type | Relevance |
|---|---|---|---|
| TGFB1 | transforming growth factor, beta 1 | mRNA | Interaction; Cytokine Signaling Treg Differentiation; Th17 Differentiation; TGF-b Signaling; Lymphocyte Activation; Host-pathogen Interaction; Hemostasis; Cytokine Signaling |
| FOXP3 | forkhead box P3 | mRNA | Treg Differentiation; Transcriptional Regulation; Lymphocyte Activation |
| STAT3 | signal transducer and activator of transcription 3 (acute-phase response factor) | mRNA | Treg Differentiation; Transcriptional Regulation; Th17 Differentiation; Host-pathogen Interaction; Cytokine Signaling; Chemokine Signaling |
| IFI35 | interferon-induced protein 35 | mRNA | Type I Interferon Signaling; Cytokine Signaling |
| IFIT2 | interferon-induced protein with tetratricopeptide repeats 2 | mRNA | Type I Interferon Signaling; Cytokine Signaling |
| IFITM1mcfarlin@unt.edu | interferon induced transmembrane protein 1 (9-27) | mRNA | Type I Interferon Signaling; Cytokine Signaling; B cell Receptor Signaling; Adaptive Immune System |
| MX1 | myxovirus (influenza virus) resistance 1, interferon-inducible protein p78 (mouse) | mRNA | Type I Interferon Signaling; Host-pathogen Interaction; Cytokine Signaling |
| BST2 | bone marrow stromal cell antigen 2 | mRNA | Type I Interferon Signaling; Lymphocyte Activation; Innate Immune System; Cytokine Signaling |
| PSMB8 | proteasome (prosome, macropain) subunit, beta type, 8 (large multifunctional peptidase 7) | mRNA | Type I Interferon Signaling; T Cell Receptor Signaling; NF-kB Signaling; MHC Class I Antigen Presentation; Innate Immune System; Immuno-metabolism; Cytokine Signaling; B cell Receptor Signaling; Apoptosis; Adaptive Immune System |
| IFNA1/13 | interferon, alpha 1/interferon, alpha 13 | mRNA | Type I Interferon Signaling; TLR Signaling; NLR signaling; Lymphocyte Activation; Host-pathogen Interaction; Cytokine Signaling |
| IFNAR1 | interferon (alpha, beta and omega) receptor 1 | mRNA | Type I Interferon Signaling; TLR Signaling; NLR signaling; Lymphocyte Activation; Host- |

SUPPLEMENTARY TABLE 3-continued

Summary of Nanostring Array RNA Biomarkers

| Abbreviation | Name | Type | Relevance |
| --- | --- | --- | --- |
| IFNAR2 | interferon (alpha, beta and omega) receptor 2 | mRNA | pathogen Interaction; Cytokine Signaling Type I Interferon Signaling; TLR Signaling; NLR signaling; Lymphocyte Activation; Host-pathogen Interaction; Cytokine Signaling |
| IFNA2 | interferon, alpha 2 | mRNA | Type I Interferon Signaling; TLR Signaling; NLR signaling; Lymphocyte Activation; Innate Immune System; Host-pathogen Interaction; Hemostasis; Cytokine Signaling |
| IFNB1 | interferon, beta 1, fibroblast | mRNA | Type I Interferon Signaling; TLR Signaling; NLR signaling; Lymphocyte Activation; Innate Immune System; Host-pathogen Interaction; Hemostasis; Cytokine Signaling |
| EGR1 | early growth response 1 | mRNA | Type I Interferon Signaling; Transcriptional Regulation; Lymphocyte Activation; Host-pathogen Interaction; Cytokine Signaling |
| STAT2 | signal transducer and activator of transcription 2, 113 kDa | mRNA | Type I Interferon Signaling; Transcr iptional Regulation; NLR signaling; Host-pathogen Interaction; Cytokine Signaling; Chemokine Signaling |
| TYK2 | tyrosine kinase 2 | mRNA | Type I Interferon Signaling; Treg Differentiation; Th17 Differentiation; Th1 Differentiation; NLR signaling; Host-pathogen Interaction; Cytokine Signaling |
| NCAM1 | neural cell adhesion molecule 1 | mRNA | Type II Interferon Signaling; Cytokine Signaling; Cell Adhesion |
| CIITA | class II, major histocompatibility complex, transactivator | mRNA | Type II Interferon Signaling; Host-pathogen Interaction; Cytokine Signaling |
| PTAFR | platelet-activating factor receptor | mRNA | Type II Interferon Signaling; Innate Immune System; Host-pathogen Interaction; Cytokine Signaling |

SUPPLEMENTARY TABLE 3-continued

Summary of Nanostring Array RNA Biomarkers

| Abbreviation | Name | Type | Relevance |
|---|---|---|---|
| CD44 | CD44 molecule (Indian blood group) | mRNA | Type II Interferon Signaling; Innate Immune System; Immuno-metabolism; Host-pathogen Interaction; Hemostasis; Cytokine Signaling |
| B2M | beta-2-microglobulin | mRNA | Type II Interferon Signaling; MHC Class I Antigen Presentation; Lymphocyte Activation; Innate Immune System; Cytokine Signaling; Adaptive Immune System |
| GBP1 | guanylate binding protein 1, interferon-inducible | mRNA | Type II Interferon Signaling; NLR signaling; Cytokine Signaling |
| GBP5 | guanylate binding protein 5 | mRNA | Type II Interferon Signaling; NLR signaling; Cytokine Signaling |
| PML | promyelocytic leukemia | mRNA | Type II Interferon Signaling; Oxidative Stress; Host-pathogen Interaction; Cytokine Signaling |
| PRKCD | protein kinase C, delta | mRNA | Type II Interferon Signaling; Oxidative Stress; NLR signaling; Lymphocyte Activation; Innate Immune System; Hemostasis; Cytokine Signaling; Chemokine Signaling; Autophagy; Apoptosis |
| FCGR1A/B | Fc fragment of IgG, high affinity Ia, receptor (CD64)/Fc fragment of IgG, high affinity Ib, receptor (CD64) | mRNA | Type II Interferon Signaling; Phagocytosis and Degradation; MHC Class I Antigen Presentation; Innate Immune System; Host-pathogen Interaction; Cytokine Signaling; Adaptive Immune System |
| HLA-DPA1 | major histocompatibility complex, class II, DP alpha 1 | mRNA | Type II Interferon Signaling; T Cell Receptor Signaling; Phagocytosis and Degradation; MHC Class II Antigen Presentation; Lymphocyte Activation; Host-pathogen Interaction; Cytokine Signaling; Cell Adhesion; Adaptive Immune System |
| HLA-DPB1 | major histocompatibility complex, class II, DP beta 1 | mRNA | Type II Interferon Signaling; T Cell Receptor Signaling; Phagocytosis and Degradation; MHC Class II Antigen |

SUPPLEMENTARY TABLE 3-continued

Summary of Nanostring Array RNA Biomarkers

| Abbreviation | Name | Type | Relevance |
|---|---|---|---|
| HLA-DQA1 | major histocompatibility complex, class II, DQ alpha 1 | mRNA | Type II Interferon Signaling; T Cell Receptor Signaling; Phagocytosis and Degradation; MHC Class II Antigen Presentation; Lymphocyte Activation; Host-pathogen Interaction; Cytokine Signaling; Cell Adhesion; Adaptive Immune System |
| HLA-DQB1 | major histocompatibility complex, class II, DQ beta 1 | mRNA | Type II Interferon Signaling; T Cell Receptor Signaling; Phagocytosis and Degradation; MHC Class II Antigen Presentation; Lymphocyte Activation; Host-pathogen Interaction; Cytokine Signaling; Cell Adhesion; Adaptive Immune System |
| HLA-DRA | major histocompatibility complex, class II, DR alpha | mRNA | Type II Interferon Signaling; T Cell Receptor Signaling; Phagocytosis and Degradation; MHC Class II Antigen Presentation; Lymphocyte Activation; Host-pathogen Interaction; Cytokine Signaling; Cell Adhesion; Adaptive Immune System |
| HLA-DRB1 | major histocompatibility complex, class II, DR beta 1 | mRNA | Type II Interferon Signaling; T Cell Receptor Signaling; Phagocytosis and Degradation; MHC Class II Antigen Presentation; Lymphocyte Activation; Host-pathogen Interaction; Cytokine Signaling; Cell Adhesion; Adaptive Immune System |
| HLA-DRB3 | major histocompatibility complex, class II, DR beta 3 | mRNA | Type II Interferon Signaling; T Cell Receptor Signaling; Phagocytosis and Degradation; MHC Class II Antigen |

SUPPLEMENTARY TABLE 3-continued

Summary of Nanostring Array RNA Biomarkers

| Abbreviation | Name | Type | Relevance |
|---|---|---|---|
| | | | Presentation; Lymphocyte Activation; Host-pathogen Interaction; Cytokine Signaling; Cell Adhesion; Adaptive Immune System |
| IFNGR1 | interferon gamma receptor 1 | mRNA | Type II Interferon Signaling; Th1 Differentiation; Lymphocyte Activation; Host-pathogen Interaction; Cytokine Signaling |
| IFNG | interferon, gamma | mRNA | Type II Interferon Signaling; Th1 Differentiation; TGF-b Signaling; T Cell Receptor Signaling; Lymphocyte Activation; Host-pathogen Interaction; Cytokine Signaling |
| JAK2 | Janus kinase 2 | mRNA | Type II Interferon Signaling; Th17 Differentiation; Th1 Differentiation; Oxidative Stress; Host-pathogen Interaction; Hemostasis; Cytokine Signaling; Chemokine Signaling |
| ICAM1 | intercellular adhesion molecule 1 | mRNA | Type II Interferon Signaling; TNF Family Signaling; NF-kB Signaling; Lymphocyte Trafficking; Lymphocyte Activation; Host-pathogen Interaction; Cytokine Signaling; Cell Adhesion; Adaptive Immune System |
| VCAM1 | vascular cell adhesion molecule 1 | mRNA | Type II Interferon Signaling; TNF Family Signaling; NF-kB Signaling; Lymphocyte Trafficking; Lymphocyte Activation; Host-pathogen Interaction; Cytokine Signaling; Cell Adhesion; Adaptive Immune System |
| HLA-A | major histocompatibility complex, class I, A | mRNA | Type II Interferon Signaling; Type I Interferon Signaling; Phagocytosis and Degradation; MHC Class I Antigen Presentation; Lymphocyte Activation; Host-pathogen Interaction; Cytokine Signaling; Cell Adhesion; Adaptive Immune System |
| HLA-B | major histocompatibility complex, class I, B | mRNA | Type II Interferon Signaling; Type I Interferon Signaling; Phagocytosis and |

SUPPLEMENTARY TABLE 3-continued

Summary of Nanostring Array RNA Biomarkers

| Abbreviation | Name | Type | Relevance |
|---|---|---|---|
| HLA-C | major histocompatibility complex, class I, C | mRNA | Degradation; MHC Class I Antigen Presentation; Lymphocyte Activation; Innate Immune System; Host-pathogen Interaction; Cytokine Signaling; Cell Adhesion; Adaptive Immune System Type II Interferon Signaling; Type I Interferon Signaling; Phagocytosis and Degradation; MHC Class I Antigen Presentation; Lymphocyte Activation; Innate Immune System; Host-pathogen Interaction; Cytokine Signaling; Cell Adhesion; Adaptive Immune System |
| PTPN6 | protein tyrosine phosphatase, non-receptor type 6 | mRNA | Type II Interferon Signaling; Type I Interferon Signaling; T Cell Receptor Signaling; Lymphocyte Activation; Innate Immune System; Host-pathogen Interaction; Hemostasis; Cytokine Signaling; B cell Receptor Signaling; Adaptive Immune System |
| SOCS1 | suppressor of cytokine signaling 1 | mRNA | Type II Interferon Signaling; Type I Interferon Signaling; TLR Signaling; MHC Class I Antigen Presentation; Innate Immune System; Host-pathogen Interaction; Cytokine Signaling; Adaptive Immune System |
| SOCS3 | suppressor of cytokine signaling 3 | mRNA | Type II Interferon Signaling; Type I Interferon Signaling; TNF Family Signaling; MHC Class I Antigen Presentation; Host-pathogen Interaction; Cytokine Signaling; Adaptive Immune System |
| IRF8 | interferon regulatory factor 8 | mRNA | Type II Interferon Signaling; Type I Interferon Signaling; Transcriptional Regulation; Host-pathogen Interaction; Cytokine Signaling |

SUPPLEMENTARY TABLE 3-continued

Summary of Nanostring Array RNA Biomarkers

| Abbreviation | Name | Type | Relevance |
|---|---|---|---|
| IRF1 | interferon regulatory factor 1 | mRNA | Type II Interferon Signaling; Type I Interferon Signaling; Transcriptional Regulation; Lymphocyte Activation; Innate Immune System; Host-pathogen Interaction; Hemostasis; Cytokine Signaling |
| IRF4 | interferon regulatory factor 4 | mRNA | Type II Interferon Signaling; Type I Interferon Signaling; Transcriptional Regulation; Th17 Differentiation; Lymphocyte Activation; Cytokine Signaling |
| IRF5 | interferon regulatory factor 5 | mRNA | Type II Interferon Signaling; Type I Interferon Signaling; Transcriptional Regulation; TLR Signaling; Cytokine Signaling |
| IRF3 | interferon regulatory factor 3 | mRNA | Type II Interferon Signaling; Type I Interferon Signaling; Transcriptional Regulation; TLR Signaling; NLR signaling; Innate Immune System; Host-pathogen Interaction; Hemostasis; Cytokine Signaling |
| IRF7 | interferon regulatory factor 7 | mRNA | Type II Interferon Signaling; Type I Interferon Signaling; Transcriptional Regulation; TLR Signaling; NLR signaling; Innate Immune System; Host-pathogen Interaction; Hemostasis; Cytokine Signaling |
| STAT1 | signal transducer and activator of transcription 1, 91 kDa | mRNA | Type II Interferon Signaling; Type I Interferon Signaling; Transcriptional Regulation; TLR Signaling; Th1 Differentiation; NLR signaling; Host-pathogen Interaction; Cytokine Signaling; Chemokine Signaling |
| JAK1 | Janus kinase 1 | mRNA | Type II Interferon Signaling; Type I Interferon Signaling; Treg Differentiation; Th17 Differentiation; Th1 |

SUPPLEMENTARY TABLE 3-continued

Summary of Nanostring Array RNA Biomarkers

| Abbreviation | Name | Type | Relevance |
|---|---|---|---|
| | | | Differentiation; NLR signaling; Host-pathogen Interaction; Hemostasis; Cytokine Signaling |

The invention claimed is:

1. A composition comprising a combination of a curcumin extract and a pomegranate extract, wherein said combination is a ratio of curcumin extract:pomegranate extract of 1:1 (w/w),
the curcumin extract containing 20-25% by weight *Curcuma longa* extract, 19-35% by weight maltodextrin, 10-20% by weight lecithin, 1-35% by weight stearic acid or salts thereof, 1-3% by weight ascorbyl palmitate, and optionally, 0.3-3% by weight silicon dioxide, the curcumin extract comprises solid lipid curcumin particles, the curcumin extract having a standardization of not less than about 20% total curcuminoids, and the pomegranate extract containing 100% by weight *Punica granatum* fruit extract, the pomegranate extract having a standardization of not less than about 10% punicalagins and 40% total polyphenols;
wherein radical scavenging activity measured by DPPH assay in micromole Trolox equivalents per gram (micromole TE/gram) is about 15% greater compared to a combination having a ratio of curcumin extract:pomegranate extract of 1:1.5 (w/w), and wherein levels of both inflammatory biomarkers IL-4 and IL-8 are increased relative to control when administered to a human subject.

2. The composition of claim 1, said combination comprising 20-30% by weight curcuminoids and 10-50% by weight punicalagins.

3. The composition of claim 2, said combination comprising not less than 20% w/w total curcuminoids, not less than 10% w/w punicalagins, and 40-50% w/w total pomegranate polyphenols.

4. A method of supporting and/or improving immune health in a subject, comprising the steps of
a. providing a composition of claim 1, and
b. administering an effective amount of the composition to a subject in need thereof to support and/or improve the immune system of the subject.

5. The method of claim 4, wherein said subject is a healthy subject and exercises regularly.

6. The method of claim 4, wherein said subject is a healthy subject and is sedentary.

7. The method of claim 4, where the subject is not a healthy subject.

8. The method of claim 4, wherein in step b, infection risk is reduced in the subject.

9. The method of claim 4, wherein in step b, gut health is improved in the subject.

10. A method of treating an immune-related disease or disorder in a subject, and a symptom thereof, comprising the steps of:
a. providing a composition of claim 1, and
b. administering an effective amount of the composition to the subject.

11. The method of claim 10, wherein said disease or disorder is caused by a viral infection.

12. The method of claim 11, wherein said disease or disorder is COVID 19.

13. The method of claim 10, wherein said disease or disorder is sepsis.

14. A method of immunomodulating the immune system of a subject, comprising the steps of
a. providing a composition of claim 1, and
b. administering an effective amount of the composition to the subject.

15. The composition of claim 1, said composition including 20-32% total pomegranate polyphenols, 3-5% bis and dimethoxy curcumin, 12-13% curcumin, 9-30% punicalagins, 10-16% stearic and palmitic acid, 1-2% ascorbyl palmitate, 10-16% dextrin, 15-20% polysaccharides, and 1-3% phosphatidylcholine.

16. The composition of claim 1, wherein said composition is a dietary supplement.

17. The composition of claim 1, wherein said composition is a powder.

18. The composition of claim 1, said composition comprising 500 mg of said combination.

19. The composition of claim 1, said composition comprising 1000 mg of said combination.

* * * * *